US009201072B2

(12) United States Patent  
Kim et al.

(10) Patent No.: US 9,201,072 B2
(45) Date of Patent: Dec. 1, 2015

(54) GUT FLORA-DERIVED EXTRACELLULAR VESICLES, AND METHOD FOR SEARCHING FOR A DISEASE MODEL, VACCINE, AND CANDIDATE DRUG AND FOR DIAGNOSIS USING THE SAME

(75) Inventors: Yoon Keun Kim, Pohang-si (KR); Yong Song Gho, Pohang-si (KR); Kyoung Su Park, Pohang-si (KR); Bok Sil Hong, Pohang-si (KR); Ji Hyun Kim, Pohang-si (KR); You Sun Kim, Pohang-si (KR); Won Hee Lee, Gyeongsangnam-do (KR); Jung Wook Kim, Seoul (KR); Dae-Kyum Kim, Gwangju (KR)

(73) Assignee: AEON MEDIX INC., Pohang-si, Gyeongsangbuk-do (KR)

( * ) Notice: Subject to any disclaimer, the term of this patent is extended or adjusted under 35 U.S.C. 154(b) by 0 days.

(21) Appl. No.: 13/393,808

(22) PCT Filed: Jul. 20, 2010

(86) PCT No.: PCT/KR2010/004747
§ 371 (c)(1),
(2), (4) Date: Mar. 1, 2012

(87) PCT Pub. No.: WO2011/027971
PCT Pub. Date: Mar. 10, 2011

(65) Prior Publication Data
US 2012/0222142 A1  Aug. 30, 2012

(30) Foreign Application Priority Data

Sep. 1, 2009  (KR) .................. 10-2009-0082220

(51) Int. Cl.
*A61K 39/00* (2006.01)
*G01N 33/569* (2006.01)
*C12Q 1/02* (2006.01)
*A01K 67/027* (2006.01)
*C12Q 1/37* (2006.01)

(52) U.S. Cl.
CPC ........ *G01N 33/56916* (2013.01); *A01K 67/027* (2013.01); *C12Q 1/025* (2013.01); *C12Q 1/37* (2013.01); *A01K 2207/20* (2013.01); *A01K 2217/075* (2013.01); *A01K 2227/105* (2013.01); *A01K 2267/035* (2013.01); *A01K 2267/0337* (2013.01)

(58) Field of Classification Search
None
See application file for complete search history.

(56) References Cited

U.S. PATENT DOCUMENTS

| 5,403,718 | A | 4/1995 | Dorward et al. |
| 7,384,645 | B2 | 6/2008 | Foster et al. |
| 2003/0059444 | A1* | 3/2003 | Zollinger et al. .......... 424/249.1 |
| 2005/0013831 | A1 | 1/2005 | Foster et al. |
| 2006/0166344 | A1 | 7/2006 | Pizza et al. |
| 2007/0087017 | A1 | 4/2007 | Olivieri et al. |
| 2007/0166333 | A1 | 7/2007 | Niebla Perez et al. |
| 2008/0233154 | A1 | 9/2008 | Berthet et al. |
| 2010/0143418 | A1 | 6/2010 | Contorni et al. |
| 2011/0251156 | A1 | 10/2011 | Shen et al. |
| 2011/0312510 | A1 | 12/2011 | Mak et al. |

FOREIGN PATENT DOCUMENTS

| CN | 1688334 A | 10/2005 |
| JP | 09-163896 | 6/1997 |
| JP | 2007-533729 A | 11/2007 |
| WO | 97/05899 A2 | 2/1997 |
| WO | 0109350 A2 | 2/2001 |
| WO | 2004/014417 A2 | 2/2004 |
| WO | 2005/004925 A1 | 1/2005 |
| WO | 2005/035733 A2 | 4/2005 |
| WO | 2007/144316 A2 | 12/2007 |
| WO | 2009/030093 A1 | 3/2009 |
| WO | 2011/127302 A2 | 10/2011 |

OTHER PUBLICATIONS

Hellman et al, The Journal of Biological Chemistry, 2002, 277:14274-14280.*
Lolis and Bucala, Nature Reviews—Drug Discovery, 2003, 2:635-645.*
Buras et al, Nature Reviews, 2005, 4:854-865.*
Munford, Annu Rev Pathol Mech Dis, 2006, 1:467-496.*
Lee et al, Mass Spectrometry Reviews, 2008, 27:535-555.*
Alaniz et al, The Journal of Immunology, 2007, 179:7692-7701.*
Mashburn-Warren and Whiteley, Molecular Microbiology, 2006, 61:839-846.*
Chaffer et al, Avian Pathology, 1997, 26:377-390.*

(Continued)

*Primary Examiner* — Gary Nickol
*Assistant Examiner* — Khatol Shahnan Shah
(74) *Attorney, Agent, or Firm* — Knobbe Martens Olson & Bear LLP

(57) ABSTRACT

The present application relates to a composition including gut flora-derived extracellular vesicles, and to an animal disease model using same. In addition, the present application relates to a method for using the gut flora-derived extracellular vesicles to efficiently search for a candidate drug which may prevent or treat diseases that occur due to gut flora-derived extracellular vesicles, and to a vaccine which can efficiently prevent or treat infections caused by gut flora or diseases that occur due to gut flora-derived extracellular vesicles. Further, the development of diagnostic technology to discover, using the gut flora-derived extracellular vesicles of the present application, the etiology of diseases that occur due to gut flora-derived extracellular vesicles, can be achieved.

5 Claims, 35 Drawing Sheets

(56) References Cited

OTHER PUBLICATIONS

Hoist et al, Vaccine, 2009, 27 Supp2:B3-B12.*
Annane et al, Lancet, 2005, 365:63-78.*
Yadav et al, Journal of Medical Microbiology, 2005, 54:375-379.*
Lepper et al, Intensive Care Med, 2002, 28:824-833.*
Muller et al, Applied and Environmental Microbiology, 2007, 73:3380-3390.*
Lee, Eun-Young, "Proteomics in Enterotoxigenic *Staphylococcus aureus* Membrane Vesicles", KHUPO 9th Annual International Preteomics Conference, P-4, p. 88 (May 25, 2009).
International Search Report dated Jun. 3, 2011 of PCT/KR2010/004747 which is the parent application—6 pages.
Lee, et al, Proteomics in gram-negative bacterial outer membrane vesicles. Mass. Spectrom. Rev. 2008;27 (6):535-555.
Namork, et al, "Fatal meningococcal septicaemia with "blebbing" meningococcus", The Lancet. Nov. 30, 2002, vol. 360, (9347), p. 1741.
Mirlashari, et al, "Outer membrane vesicles from Neisseria meningitidis: effects on cytokine production in human whole blood", Cytokine, Jan. 21, 2001, vol. 13, No. 2, pp. 91-97.
Bjerre et al., "Complement activation induced by purified Neisseria meningitidis lipopolysaccharide (LPS), outer membrane vesicles, whole bacteria, and an LPS-free mutant", The Journal of Infectious Disease, 2002, vol. 185, No. 2, pp. 220-228.
Levy, et al., "2001 SCCM/ESICM/ACCP/ATS/SIS International Sepsis Definitions Conference", Crit. Care. Med. 2003, vol. 31, No. 4, pp. 1250-1256.
Lolis, et al., "Therapeutic approaches to innate immunity: severe sepsis and septic shock", Nature Reviews, Drug Discovery, 2003, vol. 2 No. 8, pp. 635-645.
Munford, "Severe sepsis and septic shock: the role of gram-negative bacteremia" Annu. Rev.Pathol. 2006;1:467-496.
Opal, "The host response to endotoxin, antilipopolysaccharide strategies, and the management of severe sepsis", Int. J. Med. Microbiol. 2007, 297(5) pp. 365-377.
Hellman, "Bacterial peptidoglycan-associated lipoprotein is released into the bloodstream in gram-negative sepsis and causes inflammation and death in mice", J. Biol. Chem. 2002; 19;277(1 6), pp. 14274-14280.
Buras et al., "Animal models of sepsis: setting the stage", Nat. Rev. Drug. Discov. 2005;4(10), pp. 854-865.
Girard et al., "A review of vaccine research and development: meningococcal disease", Vaccine. 2006;24(22), pp. 4692-4700.
Alaniz et al., "Membrane vesicles are immunogenic facsimiles of *Salmonella typhimurium* that potently activate dendritic cells, prime B and T cell responses, and stimulate protective immunity in Vivo", J Immunol. 2007;179(11), pp. 7692-7701.
Mashburn-Warren, et al., "Special delivery: vesicle trafficking in prokaryotes", Molecular Microbiology, 2006, vol. 61, No. 4, pp. 839-846.
Extended European Search Report dated Apr. 10, 2014 of the corresponding European Patent Application No. 108138801—20 pages.
Rolhion et al., "Strong decrease in invasive ability and outer membrane vesicle release in Crohn's disease-associated adherent-invasive *Escherichia coli* strain LF82 with the yfgL gene deleted", Journal of Bacteriology, 2005, vol. 187, No. 7, pp. 2286-2296.
Leduc et al., "Outer Membrane-associated Deoxyribonuclease Activity of Porphyromonas gingivalis", Anaerobe, 1995, vol. 1, No. 2, pp. 129-134.
Patrick et al, "A comparison of the haemagglutinating and enzymic activities of Bacteroides fragilis whole cells and outer membrane vesicles.", Microbial Pathogenesis, 1996, vol. 20, No. 4, pp. 196-202.
Kim et al, "Engineered Bacterial Outer Membrane Vesicles with Enhanced Functionality", Journal of Molecular Biology, 2008, vol. 308, No. 1, pp. 51-66.
Lee et al, "Global proteomic profiling of native outer membrane vesicles derived from *Escherichia coli*" Proteomics, 2007, vol. 7, No. 17, pp. 3143-3153.
Henry et al, "Improved methods for producing outer membrane vesicles in Gram-negative bacteria", Research in Microbiology, 2004, vol. 155, No. 6, pp. 437-446.
Kesty et al, "Enterotoxigenic *Escherichia coli* vesicles target toxin delivery into mammalian cells", The EMBO Journal, 2004, vol. 23, No. 23, pp. 4538-4549.
Schild et al, "Immunization with Vibrio 1-4 cholerae Outer Membrane Vesicles Induces Protective Immunity in Mice", Infection and Immunity, 2008, vol. 76, No. 10, pp. 4554-4563.
Schild et al, "Characterization of Vibrio cholera Outer Membrane Vesicles as a Candidate Vaccine for Cholera", Infection and Immunity, 2008, vol. 77, No. 1, pp. 472-484.
Alaniz et al, "Membrane vesicles are immunogenic facsimiles of *Salmonella typhimurium* that potently activate dendritic cells, prime B and T cell responses, and stimulate protective immunity in vivo", Journal of Immunology, 2007, vol. 179, No. 11, pp. 7692-7701.
Eckburg et al, "Diversity of the Human Intestinal Microbial Flora", Science, 2005, vol. 308, No. 5278, pp. 1635-1638.
Park et al, "Outer Membrane Vesicles Derived from *Escherichia coli* Induce Systemic Inflammatory Response Syndrome", PLOS ONE, 2010, vol. 5, No. 6.
Lee et al, "Gram-positive bacteria produce membrane vesicles: Proteomics-based characterization of *Staphylococcus aureus*-derived membrane vesicles", Proteomics, 2009, vol. 9, No. 24, pp. 5425-5436.
Shen et al, "Outer Membrane Vesicles of a Human Commensal Mediate Immune Regulation and Disease Protection", Cell Host & Microbe, 2012, vol. 12, No. 4, pp. 509-520.
Kang et al, "Extracellular Vesicles Derived from Gut Microbiota, Especially Akkermasia muciniphila, Protect the Progression of Dextran Sulfate Sodium-Induced Colitis", PLOS ONE, 2013, vol. 8, No. 10.
Kim et al, "Outer Membrane Vesicles Derived from *Escherichia coli* Up-Regulate Expression of Endothelial Cell Adhesion Molecules in Vitro and in Vivo", PLOS ONE, 2013, vol. 8, No. 3.
Schmolz, "Autospecificity in *Escherichia coli* autovaccines: Effects on the human immune system in vitro", Old Herborn University Seminar Monograph, 2002, vol. 15, pp. 159-173.
Soderblom, et al, "Effects of the *Escherichia coli* toxin cytolysin A on mucosal immunostimulation via epithelial Ca2+ signaling and Toll-like receptor 4", Cell Microbiol., 2005, vol. 7, No. 6, pp. 779-788.
Yan, et al, "The Study for the immune-protection of *E. coli* 0157:H7 outer membrane protein in rats", Zhonghua Yixue Zazhi, 2004, vol. 84, No. 1, pp. 58-62. English Abstract enclosed.
Yang, et al., "Effects of endotoxin derived from *Escherichia coli* lipopolysaccharide on the pharmacokinetics of drugs," Arch Pharm Res., 2008, vol. 31, No. 9, pp. 1073-1086.
Heo, et al., "LPS induces inflammatory responses in human aortic vascular smooth muscle cells via Toll-like receptor 4 expression and nitric oxide production," Immunology Letters., 2008, vol. 120, No. 1-2, pp. 57-64.
Blanque, et al., "Increases in osteocalcin after ovariectomy are amplified by LPS injection: strain differences in bone remodeling," Gen Pharmacol, 1998, vol. 30, No. 1, pp. 51-56.
Neilsen, et al, "*Escherichia coli* Braun lipoprotein induces a lipopolysaccharide-like endotoxic response from primary human endothelial cells," J Immunol., 2001, vol. 167, No. 9, pp. 5231-5239.
Japanese Office Action dated Oct. 2, 2013 of the corresponding Japanese Patent Application No. 2012-527808.
Chin J Clini Hepatol, Oct. 2008, vol. 24, No. 5, pp. 388-391.
Chinese Office Action dated Feb. 14, 2014 of corresponding Chinese Patent Application No. 201080038540.9—8 pages.
Serushago et al., "Role of Antibodies against Outer-membrane Proteins in Murine Resistance to Infection with Encapsulated Klebsiella pneumoniae", Journal of General Microbiology, 1989, vol. 135, pp. 2259-2268, 1989.
Yadav et al., "Lipopolysaccharide-Mediated Protection against Klebsiella pneumoniae-Induced Lobar Pneumonia: Intranasal vs. Intramuscular Route of Immunization", Folia Microbiol, 2004, vol. 50 (1), pp. 83-86.

(56) References Cited

OTHER PUBLICATIONS

Japanese Office Action dated Aug. 15, 2014 for corresponding JP Application No. 2012-527808.
Dorward, et al., "DNA is Packaged within Membrane-Derived Vesicles of Gram-Negative but not Gram-Positive Bacteria", Applied and Environmental Microbiology, Jun. 1990, vol. 56. No. 6, pp. 1960-1962.
Eda, et al., "Extracellular membranous structures in a stable L-form of *Staphylococcus aureus*", Journal of General Microbiology, 1977, vol. 103, No. 1, pp. 189-191.
International Search Report issued on Jun. 10, 2011 for International Application No. PCT/KR2010/005721—5 pages.
Japanese Office Action dated Feb. 4, 2014 of the corresponding Japanese Patent Application No. 2012-527815.4 pages.
Kim, et al., "Extracellular Membrane Vesicles from Tumor Cells Promote Angiogenesis via Sphingomyelin", Cancer Research, 2002, vol. 62, No. 21, pp. 6312-6317.
Kuehn, et al., "Bacterial outer membrane vesicles and the host-pathogen interaction", Genes & Development, 2005, vol. 19, No. 22, pp. 2645-2655.
Supplementary European Search Report dated Oct. 10, 2013 of the corresponding European Patent Application No. 10 813 899.1.
Rodrigues, et al., "Extracellular Vesicles Produced by Cryptococus neoformans Contain Protein Components Associated with Virulence", Eukaryotic Cell, Jan. 2008, vol. 7, No. 1, pp. 58-67.

* cited by examiner

FIG. 1

| DB | Species | Gram staining | Growth condition | Proteins |
|---|---|---|---|---|
| Mouse | Mus musculus | | | 73 |
| Bacteria (10 species) | Bacteroides thetaiotaomicron | Gram(-) | Obligative anaerobe | 53 |
| | Escherichia coli K-12 | Gram(-) | Facultative anaerobe | 9 |
| | Klebsiella pneumoniae | Gram(-) | Facultative anaerobe | 15 |
| | Bifidobacterium longnum | Gram(+) | Obligative anaerobe | 18 |
| | Clostridium perfringens | Gram(+) | Obligative anaerobe | 25 |
| | Enterococcus faecalis | Gram(+) | Facultative anaerobe | 19 |
| | Eubacterium rectale | Gram(+) | Obligative anaerobe | 19 |
| | Lactobacillus reuteri | Gram(+) | Facultative anaerobe | 25 |
| | Propiobacterium acnes | Gram(+) | Aerotolerant | 11 |
| | Streptococcus agalactiae | Gram(+) | Facultative anaerobe | 28 |
| Sum | Gram(-) | 77 | Total | 295 |
| | Gram(+) | 145 | | |

FIG. 2

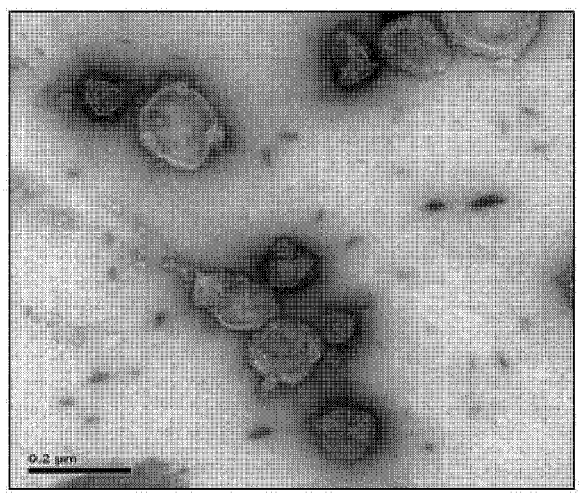

Scale bar = 0.2 µm

16S rRNA sequence of extracted E. coli in gut

Scale bar = 500 nm    Scale bar = 500 nm

Scale bar = 100 nm    Scale bar = 25 nm

Scale bar = 100 nm

Blue: PBS, Green: EC_EV(10ug), Pink: EC_EV(20ug)

FIG. 34
Normal (PBS)
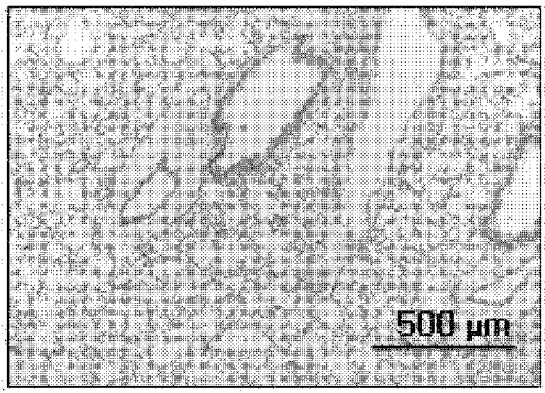
Scale bar = 500 um
Normal (EC_EV_6h)
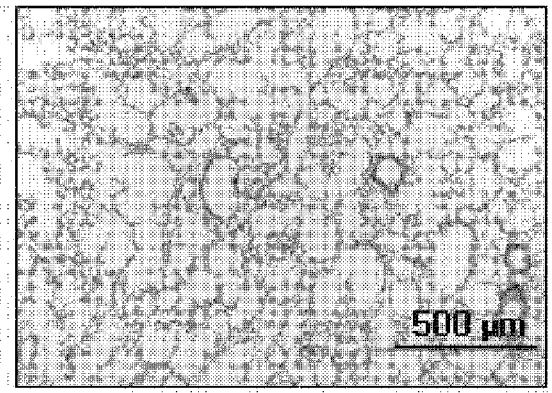
Scale bar = 500 um
IL-6$^{-/-}$(PBS)
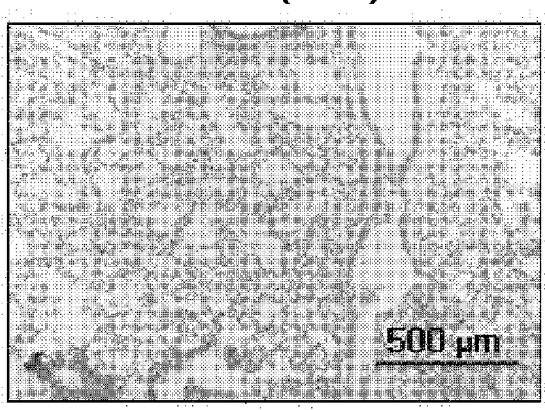
Scale bar = 500 um
IL-6$^{-/-}$(EC_EV_6h)
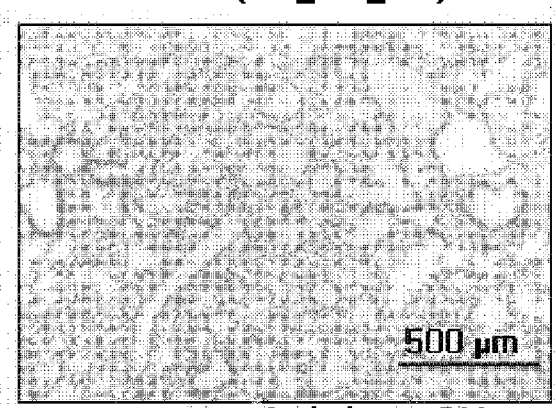
Scale bar = 500 um

SEQUENCE LISTING

```
<160> NUMBER OF SEQ ID NOS: 5

<210> SEQ ID NO 1
<211> LENGTH: 1381
<212> TYPE: DNA
<213> ORGANISM: Artificial sequence
<220> FEATURE:
<223> OTHER INFORMATION: 16S rRNA sequence of extracted E.coli gut

<400> SEQUENCE: 1
```

```
ttgcttctttt gctgacgagt ggcggacggg tgagtaatgt ctgggaaact gcctgatgga    60
gggggataac tactggaaac ggtagctaat accgcataac gtcgcaagac caaagagggg   120
gaccttcggg cctcttgcca tcggatgtgc ccagatggga ttagctagta ggtgggtaa    180 cggctcacct aggcgacgat ccctagctgg tctgagagga tgaccagcca cactggaact   240
gagacacggt ccagactcct acgggaggca gcagtgggga atattgcaca atgggcgcaa   300
gcctgatgca gccatgccgc gtgtatgaag aaggccttcg ggttgtaaag tactttcagc   360
ggggaggaag ggagtaaagt taatacccttt gctcattgac gttacccgca gaagaagcac   420
cggctaactc cgtgccagca gccgcggtaa tacgagaggt gcaagcgtta tcggaatta    480 ctgggcgtaa agcgcacgca ggcggtttgt taagtcagat gtgaaatccc cgggctcaac   540
ctgggaactg catctgatac tggcaagctt gagtctcgta gagggggta gaattccagg   600 tgtagcggtg aaatgcgtag agatctggag gaataccggt ggcgaaggcg ccccctgga   660 cgaagactga cgctcaggtg cgaaagcgtg gggagcaaac aggattagat accctggtag   720
tccacgccgt aaacgatgtc gacttggagg ttgtgcccctt gaggcgtggc ttccggagct   780
aacgcgttaa gtcgaccgcc tggggagtac ggccgcaagg ttaaaactca aatgaattga   840
cgggggcccg cacaagcggt ggagcatgtg gtttaattcg atgcaacgcg aagaaccta   900 cctggtcttg acatccacag aacttttccag agatggatag gtgccttcgg gaactgtgag   960
acaggtgctg catggctgtc gtcagctcgt gttgtgaaat gttgggttaa gtcccgcaac  1020
gagcgcaacc cttatccttt gttgccagcg gtccggccgg gaactcaaag gagactgcca  1080
gtgataaact ggaggaaggt ggggatgacg tcaagtcatc atggccctta cgaccagggc  1140
tacacacgtg ctacaatggc gcatacaaag agaagcgacc tcgcgagagc aagcggacct  1200
cataaagtgc gtcgtagtcc ggattggagt ctgcaactcg actccatgaa gtcggaatcg  1260
ctagtaatcg tggatcagaa tgccacggtg aatacgttcc cgggccttgt acacaccgcc  1320
cgtcacacca tgggagtggg ttgcaaaaga agtaggtagc ttaaccttcg ggagggcgct  1380
a                                                                  1381
```

<210> SEQ ID NO 2
<211> LENGTH: 325
<212> TYPE: DNA
<213> ORGANISM: Artificial sequence
<220> FEATURE:
<223> OTHER INFORMATION: Genetic substance from C57BL/6 mouse feces
<220> FEATURE:
<221> NAME/KEY: MISC_FEATURE
<222> LOCATION: (1), (2), (7), (9), (10), (15), (153), (156), (162),
      (177), (191), (236), (290), (291), (301), (313), (325)
<223> OTHER INFORMATION: n= a, t, g, or c

<400> SEQUENCE: 2

```
nnggagngnn gtccnctgga ctgagacacg gtccagactc ctacgggagg cagcagtggg    60
gaatattgga caatgggcgc aagcctgatc cagccatrcc gcgtgggtga agaaggcctt   120
cggrttgtaa agcccttttg ttgggaaaga anccngctg gntaataccc ggttggnatg    180
acggtaccca nagaataagc accggctaac ttcgtgccag cagccgcggt aatacnaagg   240
gtgcaagcgt tactcggaat tactgggcgt aaagcgtgcg taggtggtcn nttaagtccg   300
ntgtgaaatc ccnggggctc aaaan                                         325
```

<210> SEQ ID NO 3
<211> LENGTH: 322

```
<212> TYPE: DNA
<213> ORGANISM: Artificial sequence
<220> FEATURE:
<223> OTHER INFORMATION: Genetic substance from BALB/c mouse feces
<220> FEATURE:
<221> NAME/KEY: MISC_FEATURE
<222> LOCATION: (1)...(5), (7), (8), (10), (15), (156), (159), (170)
<223> OTHER INFORMATION: n= a, t, g, or c

<400> SEQUENCE: 3
nnnnngnntn gcccnctgga ctgagacacg gtccagactc ctacgggagg cagcagtggg      60
gaatattgga caatgggcgc aagcctgatc cagccatacc gcgtgggtga agaaggcctt     120
cgggttgtaa agccctttg ttgggaaaga aatccngcng gctaataccn ggttgggatg      180
acggtaccca aagaataagc accggctaac ttcgtgccag cagccgcggt aatacgaagg     240
gtgcaagcgt tactcggaat tactgggcgt aaagcgtgcg taggtggtcg tttaagtccg     300
ttgtgaaatc cccgggctca aa                                              322

<210> SEQ ID NO 4
<211> LENGTH: 20
<212> TYPE: DNA
<213> ORGANISM: Artificial sequence
<220> FEATURE:
<223> OTHER INFORMATION: bacterial universal forward primer

<400> SEQUENCE: 4
aaggcgacga tccctagctg                                                 20

<210> SEQ ID NO 5
<211> LENGTH: 20
<212> TYPE: DNA
<213> ORGANISM: Artificial sequence
<220> FEATURE:
<223> OTHER INFORMATION: bacterial universal reverse primer

<400> SEQUENCE: 5
ttgagcccgg ggatttcaca                                                 20
```

GUT FLORA-DERIVED EXTRACELLULAR VESICLES, AND METHOD FOR SEARCHING FOR A DISEASE MODEL, VACCINE, AND CANDIDATE DRUG AND FOR DIAGNOSIS USING THE SAME

TECHNICAL FIELD

The present invention relates to a composition comprising gut microbiota- or gut flora-derived extracellular vesicles from extracellular vesicles, a disease animal model established with the same, and a vaccine for the prevention and/or therapy of diseases caused by gut microbiota- or gut flora-derived vesicles.

BACKGROUND ART

Gut microbiota or flora consists of microorganisms that live in the digestive tracts of animals. The 10 trillion or so microbial cells living in the gut, exceed the number of human cells by 10 to 1.

In the 1960s, electron microscopy revealed that Gram-negative cells release extracellular vesicles (EV) or outer membrane vesicles (OMV). Extracellular vesicles are spherical with a size of 20-200 nm and consist of phospholipid bilayers. Gram-negative bacterial extracellular vesicles have various outer membrane proteins as well as LPS (E. Y. Lee et al., Proteomics in gram-negative bacterial outer membrane vesicles. Mass. Spectrom. Rev. 2008; 27(6):535-555). There are reports on the presence of meningococcal vesicles in the blood of patients with fatal sepsis (E. Namork and P. Brandtzaeg, Fatal meningococcal sepsis with "blebbing" meningococcus. Lancet. 2002; 360(9347):1741), and the ex vivo secretion of an inflammatory mediator from meningococcal extracellular vesicles (M. R. Mirlashari et al., Outer membrane vesicles from *Neisseria meningitidis*: effects on cytokine production in human whole blood. Cytokine. 2001; 13(2):91-97; A. Bjerre et al., Complement activation induced by purified *Neisseria meningitidis* lipopolysaccharide (LPS), outer membrane vesicles, whole bacteria, and an LPS-free mutant. J. Infect. Dis. 2002; 185(2):220-228). However, nowhere have gut flora-derived extracellular vesicles been reported to cause local diseases characterized by mucosal inflammation such as in gastritis, peptic ulcer, stomach cancer, inflammatory enterocolitis, colorectal cancer, etc., and systemic inflammatory diseases such as sepsis, arteriosclerosis, diabetes, etc. in previous literature.

Recently, the prevalence rate of sepsis has increased around the world because of people's defense systems against bacterial infection being weakened with an increase in the aged population and the use of immunosuppressants and anticancer agents. Sepsis is a potentially deadly disease that is characterized by a systemic inflammatory state resulting as a complication from the local bacterial or fungal infection (M. M. Levi et al. 2001 SCCM/ESICM/ACCP/ATS/SIS International Sepsis Definitions Conference. Crit. Care. Med. 2003; 31(4):1250-1256). In sepsis, the substance that is introduced into the blood after being secreted by pathogens upon local infection and which is secreted by pathogens introduced into blood vessels activates intravascular inflammatory cells to induce systemic inflammatory response syndrome and simultaneously activates endothelial cells to cause disseminated intravascular coagulation and thrombosis. In addition, the substances secreted from the pathogens are assigned to the major organs such as the lung to provoke inflammation and corresponding tissue injury, with a mortality rate of 30% (E. Lolis and R. Bucala, Therapeutic approaches to innate immunity: severe sepsis and septic shock. Nat. Rev. Drug. Discov. 2003; 2(8):635-645).

Sepsis is defined as systemic inflammatory response syndrome in response to a pathogenic process. However, in over half the cases of sepsis no specific pathogen is identified (R. S. Munford, Severe sepsis and septic shock: the role of gram-negative bacteremia. Annu. Rev. Pathol. 2006; 1:467-496). This indicates that the direct introduction of pathogens into the blood is not essential for the onset of sepsis, suggesting that pathogen-derived substances introduced into the blood might be a cause of sepsis. For example, on the basis of the finding that when introduced into the blood, lipopolysaccharide (LPS), a Gram-negative bacterial endotoxin, causes sepsis, research has widely been conducted to develop sepsis therapeutics (S. M. Opal, The host response to endotoxin, antilipopolysaccharide strategies, and the management of severe sepsis. Int. J. Med. Microbiol. 2007; 297(5):365-377). However, no therapeutics targeting LPS have been successfully developed thus far (J. Hellman, Bacterial peptidoglycan-associated lipoprotein is released into the bloodstream in gram-negative sepsis and causes inflammation and death in mice. J. Biol. Chem. 2002; 19; 277(16): 14274-14280).

It is very important to construct proper animal models mimicking human diseases in developing technologies for diagnosis, prophylaxis and therapy of human diseases. To establish sepsis animal models, the following three methods have been employed so far (J. A. Buras et al., Animal models of sepsis: setting the stage. Nat. Rev. Drug. Discov. 2005; 4(10):854-865): intraperitoneal injection of LPS; intraperitoneal injection of pathogens; and cecal ligation and puncture (CLP). However, these sepsis animal models suffer from the drawback of being low in reproducibility and great in error rate between operators and lacking the ability to properly express the phenotype of sepsis. Hence, an animal model that is highly reproducible and able to sufficiently express the phenotype of human sepsis, with a low error guaranteed between operators is required for the development of techniques for the diagnosis, prevention and treatment of sepsis.

An increase in blood inflammatory cytokine (particularly, IL-6) level is the hallmark of sepsis. There is known a method for evaluating the effect of therapeutic candidates on bacterial infection by measuring the level of the inflammatory factors induced by bacteria (PCT International Patent Publication No. WO2009/030093 Functions and uses of human protein phosphatase 1 inhibitor-2). However, little is known about any method for ex vivo screening candidate drugs capable of regulating inflammatory mediators by applying gut flora-derived extracellular vesicles to cells or for in vivo screening candidate drugs capable of regulating inflammatory mediators by applying the candidate drugs to a sepsis animal model established with gut flora-derived extracellular vesicles.

From decades ago, vaccines based on bacterial exotoxin proteins have been developed and used. Vaccines against Gram-positive bacteria have been developed on the basis of capsular polysaccharides, but suffer from the disadvantage of inducing the formation of antibodies independent of T cells. Developed to avoid this problem were vaccines in which a protein is conjugated with a capsular polysaccharide. These types of vaccines, however, work only on a sub-type of specific bacteria. So far, no clinical cases of using vaccines against Gram-negative bacteria have been reported. Recently, a vaccine against the Gram-negative bacterium meningococcus was developed from the artificial vesicles that were produced by treating the bacteria with a detergent (M. P. Girard et al., A review of vaccine research and development: meningococcal disease. Vaccine. 2006; 24(22):4692-4700). U.S.

Pat. No. 7,384,645 "Outer membrane vesicles from Gram negative bacteria and use as a vaccine" discloses the use of the vesicles derived from meningococcus as a vaccine. U.S. Pat. Publication No. US 2007/0166333 "Method of antigen incorporation into *neisseria* bacterial outer membrane vesicles and resulting vaccine formulations" addresses a method for the incorporation of a protein antigen into meningococcal vesicles whereby the resulting vesicles maintain the immunogenicity and immunostimulatory properties of the vesicles and generate a superior immune response and thus can be used as a vaccine for the prophylaxis and therapy of meningococcal infection. In addition, with regard to the production and use of meningococcal vaccines, a process of making novel engineered meningococcal strain which is suitable for the production of meningococcal vaccines is disclosed (PCT International Patent Publication Nos. WO 2007/144316 and WO 2004/014417). Further, *salmonella*-derived vesicles were evaluated as a vaccine for activating congenital and acquired immune responses of hosts (R. C. Alaniz et al., Membrane vesicles are immunogenic facsimiles of *Salmonella typhimurium* that potently activate dendritic cells, prime B and T cell responses, and stimulate protective immunity in vivo. J. Immunol. 2007; 179(11):7692-701). No reports have thus far been suggested on the use of extracellular vesicles as a vaccine for the prophylaxis and therapy of diseases caused by gut flora-derived extracellular vesicles and infection by gut flora.

DISCLOSURE

Technical Problem

Primarily, the present invention aims to provide a composition comprising gut flora-derived extracellular vesicles and a disease animal model using the same.

Also, the present invention aims to provide a method for effectively screening drug candidates preventive or therapeutic of diseases caused by gut flora-derived extracellular vesicles.

Also, the present invention aims to provide a vaccine preventive or therapeutic of diseases caused by gut flora-derived extracellular vesicles.

Also, the present invention aims to provide a vaccine preventive or therapeutic against the infection of gut flora.

Also, the present invention aims to provide a method for preventing or treating diseases caused by gut flora-derived extracellular vesicles and/or infection by gut flora using the vaccine.

Also, the present invention aims to provide a method for diagnosing a pathogenic factor of diseases caused by gut flora-derived extracellular vesicles.

The objects of the present invention are not limited to those mentioned above, and other objects, advantages and features of the present invention will be clearly understood to those skilled in the art from the following description.

Technical Solution

In accordance with an aspect thereof, the present invention provides a composition comprising gut flora-derived extracellular vesicles.

In one embodiment of this aspect, the gut flora may be Gram-negative bacteria, but is not limited thereto.

In another embodiment, the Gram-negative gut bacteria may be selected from the group consisting of, but not limited to, *Escherichia coli, Klebsiella pneumoniae, Pseudomonas* spp. and *Bacteroides* spp.

In another embodiment, the extracellular vesicles may be isolated from a gut microbiota culture, but is not limited thereto.

According to another embodiment, the extracellular vesicles are ones that are spontaneously or artificially formed.

In another embodiment, the extracellular vesicles may be ones that are separated from feces, intestines, gastric fluid, intestinal fluid or oral fluid, but are not limited thereto.

In accordance with another aspect thereof, the present invention provides a disease model established by administering gut flora-derived extracellular vesicles to an animal.

The gut flora and the extracellular vesicles are as described above.

In one embodiment of this aspect, the animal may be a mouse, but is not limited thereto.

The administration includes intraperitoneal, intravenous, oral, intrarectal, intranasal, and intratracheal administration.

The disease includes sepsis, arteriosclerosis, acute coronary syndrome, stroke, emphysema, acute respiratory distress syndrome, osteoporosis, hypertension, obesity, diabetes, arthritis, and cerebral diseases.

According to another embodiment, the disease includes mouth ulcer, oral cancer, esophagitis, esophageal cancer, gastritis, duodenal ulcer, stomach cancer, inflammatory bowel disease, irritable bowel syndrome, colorectal cancer, cholangitis, cholecystitis, pancreatitis, cholangiocarcinoma, and pancreatic cancer.

In accordance with a further aspect thereof, the present invention provides a method for screening candidate drugs for the prophylasis or therapy of diseases using gut flora-derived extracellular vesicles.

In this context, the gut flora, the extracellular vesicles, and the diseases are as mentioned above.

According to one embodiment of this aspect, the screening method may comprise treating cells with gut flora-derived extracellular vesicles. The cells include inflammatory cells, epithelial cells, vascular endothelial cells, and stem cells. The inflammatory cells include monocytes, neutrophils, eosinophils, basophils, and cells differentiated from monocytes in tissues. The stem cells may be derived from, but not limited to, the bone marrow or adipose tissues.

In another embodiment, the screening method may comprise administering a candidate, together with gut flora-derived extracellular vesicles, and determining the level of an inflammation-related mediator. The inflammation-related mediator includes interleukin-6 (IL-6).

In another embodiment, the screening method may comprise administering a candidate, together with gut flora-derived extracellular vesicles, and evaluating an inflammation-related signaling pathway.

In accordance with still a further aspect thereof, the present invention provides a vaccine for the prophylaxis or therapy of a disease caused by gut flora-derived extracellular vesicles, comprising gut flora-derived extracellular vesicles. In this context, the gut flora, the extracellular vesicles, and the disease are as described above, respectively.

According to one embodiment of this aspect, the vaccine may be modified to enhance medicinal efficacy or alleviate side effects. The modification may be achieved by the use of transformed bacteria or by the treatment of bacteria with a compound. This compound may include a drug.

In another embodiment, the extracellular vesicles may be modified by treatment with a compound so as to enhance medicinal efficacy or alleviate side effects, said compound including a drug.

In a further embodiment, the vaccine may be used in combination with a drug or an immunopotentiator to enhance medicinal efficacy or alleviate side effects, but the present invention is not limited by this.

In accordance with still another aspect thereof, the present invention provides a vaccine preventive or therapeutic against gut flora infection, comprising gut flora-derived extracellular vesicles.

According to one embodiment of this aspect, the gut flora infection may include, but not limited to, peritonitis, sepsis, pneumonia, urinary tract infection, bone infection, and central nervous system infection.

The gut flora is as mentioned above.

According to another embodiment, the vaccine may be modified to enhance medicinal efficacy or alleviate side effects. The modification may be achieved by the use of transformed bacteria or by the treatment of bacteria with a compound. This compound may include a drug.

In another embodiment, the extracellular vesicles may be modified by treatment with a compound so as to enhance medicinal efficacy or alleviate side effects, said compound including a drug.

In a further embodiment, the vaccine may be used in combination with a drug or an immunopotentiator to enhance medicinal efficacy or alleviate side effects, but the present invention is not limited by this.

Contemplated in accordance with yet another aspect of the present invention is a method for preventing or treating a disease which comprises administering gut flora-derived extracellular vesicles at a sub-lethal dose to a mammal.

In this context, the gut flora and the extracellular vesicles are as described above.

According to one embodiment of this aspect, the disease includes a disease which is caused or aggravated by gut flora-derived extracellular vesicles.

In another embodiment, the disease may include, but is not limited to, sepsis, arteriosclerosis, acute coronary syndrome, stroke, emphysema, acute respiratory distress syndrome, osteoporosis, hypertension, obesity, diabetes, arthritis, and a cerebral disease.

In another embodiment, the disease may include, but is not limited to, mouth ulcer, oral cancer, esophagitis, esophageal cancer, gastritis, duodenal ulcer, stomach cancer, inflammatory bowel disease, irritable bowel syndrome, colorectal cancer, cholangitis, cholecystitis, pancreatitis, cholangiocarcinoma, and pancreatic cancer.

According to another embodiment, the disease may include, but is not limited to, peritonitis, sepsis, pneumonia, urinary tract infection, bone infection and central nervous system infection.

In another embodiment, the administration includes subcutaneous injection, intravenous injection, intranasal administration, sublingual administration, intratracheal inhalation, oral administration, intrarectal administration, transdermal administration, and mucosal administration.

In another embodiment, the extracellular vesicles may be modified to enhance medicinal efficacy or alleviate side effects. The modification may be achieved by the use of transformed bacteria or the treatment of bacteria or extracellular vesicles with a compound. This compound may include a drug.

In a further embodiment, the extracellular vesicles may be used in combination with a drug or an immunopotentiator to enhance medicinal efficacy or alleviate side effects, but the present invention is not limited by this.

In accordance with yet a further aspect thereof, the present invention provides a pharmaceutical composition for the prophylaxis or therapy of a disease, comprising a substance selected by the screening method using gut flora-derived extracellular vesicles according to the present invention.

According to one embodiment of this aspect, the substance may be a kinase inhibitor. Examples of the kinase inhibitor include Damnacanthal (3-hydroxy-1-methoxy-9,10-dioxoanthracene-2-carbaldehyde), H-7 (5-(2-methylpiperazin-1-yl)sulfonylisoquinoline dihydrochloride), LY294002 (2-morpholin-4-yl-8-phenylchromen-4-one), GF109203X (3-[1-[3-(dimethylamino)propyl]indol-3-yl]-4-(1H-indol-3-yl)pyrrole-2,5-dione), ML-7 (1-(5-iodonaphthalen-1-yl)sulfonyl-1,4-diazepane hydrochloride), ML-9 (1-(5-chloronaphthalen-1-yl)sulfonyl-1,4-diazepane hydrochloride), ZM449829 (1-(2-Naphthalenyl)-2-propen-1-one), DRB ((2S,3S,4R,5R)-2-(5,6-dichlorobenzimidazol-1-yl)-5-(hydroxymethyl)oxolane-3,4-diol), Indirubin-3'-monoxime (3-[3-(hydroxyamino)-1H-indol-2-yl]indol-2-one), Kenpaullone (9-bromo-7,12-dihydro-5H-indolo[3,2-d][1]benzazepin-6-one), BML-259 (N-(5-Isopropylthiazol-2-yl)phenylacetamide), and Apigenin (5,7-dihydroxy-2-(4-hydroxyphenyl)chromen-4-one).

In another embodiment, the substance may be a phosphatase inhibitor. This phosphatase inhibitor may include PD-144795 (5-methoxy-3-(1-methylethoxy)benzo(b)thiophene-2-carboxamide-1-oxide).

According to a further embodiment, the substance may be a prodrug. Examples of the prodrug include Amitriptyline, Cyclobenzaprine, Desipramine, Doxepin, Fluphenazine dichloride, Haloperidol, Imipramine, Maprotiline, Orphenadrine, Terfenadine, Tolfenamic acid, Trazodone HCl, Trichlormethiazide, and Verapamil.

In another embodiment, the disease includes a disease that is caused or aggravated by gut flora-derived extracellular vesicles.

In another embodiment, the disease may include, but is not limited to, sepsis, arteriosclerosis, acute coronary syndrome, stroke, emphysema, acute respiratory distress syndrome, osteoporosis, hypertension, obesity, diabetes, arthritis, and a cerebral disease.

In another embodiment, the disease may include, but is not limited to, mouth ulcer, oral cancer, esophagitis, esophageal cancer, gastritis, duodenal ulcer, stomach cancer, inflammatory bowel disease, irritable bowel syndrome, colorectal cancer, cholangitis, cholecystitis, pancreatitis, cholangiocarcinoma, and pancreatic cancer.

Contemplated in accordance with yet still another aspect of the present invention is a method for diagnosing a factor causative of a disease through the application of gut flora-derived extracellular vesicles.

In this context, the gut flora is as described above.

In another embodiment, the disease may include, but is not limited to, sepsis, arteriosclerosis, acute coronary syndrome, stroke, emphysema, acute respiratory distress syndrome, osteoporosis, hypertension, obesity, diabetes, arthritis, and a cerebral disease.

In another embodiment, the disease may include, but is not limited to, mouth ulcer, oral cancer, esophagitis, esophageal cancer, gastritis, duodenal ulcer, stomach cancer, inflammatory bowel disease, irritable bowel syndrome, colorectal cancer, cholangitis, cholecystitis, pancreatitis, cholangiocarcinoma, and pancreatic cancer.

According to another embodiment, the application may comprise analyzing the base sequences of a genetic material contained in the gut flora-derived extracellular vesicles. The genetic material may be 16S rRNA, but is not limited thereto.

According to another embodiment, the application may include the determination of the level of proteins in the gut flora-derived extracellular vesicles or the determination of an immune response to the gut flora-derived extracellular vesicles, but is not limited thereto. The determination of immune responses may include the quantitative determination of antibodies to the gut flora-derived extracellular vesicles, but is not limited thereto.

In another embodiment, the diagnosis may be determined with a sample selected from the group consisting of, not limited to, blood, feces, urine, cerebrospinal fluid, synovial fluid, pleural fluid, and ascites.

Advantageous Effects

Based on the finding that extracellular vesicles derived from intestinal bacteria that colonize the digestive tract cause local diseases characterized by mucosal inflammation and systemic disease, such as sepsis, characterized by systemic inflammatory responses upon introduction into blood, the present invention utilizes gut flora-derived extracellular vesicles in establishing a disease model, a method for screening candidate drugs preventive or therapeutic of diseases, and a vaccine for the prophylaxis or therapy of diseases.

In the present invention, it was found that gut flora-derived extracellular vesicles induced the secretion of an inflammatory factor from cells when applied to the cells, and caused mucosal inflammation when administered topically, and systemic diseases including sepsis, intravascular blood coagulation, emphysema, hypertension and osteoporosis when intraperitoneally injected. Thus, the present invention utilized the finding to construct a disease animal model and a method for effectively screening a candidate drug. In addition, the screening method using gut flora-derived extracellular vesicles allows the effective excavation of drugs preventive or therapeutic of diseases caused by the gut flora-derived extracellular vesicles. Further, the gut flora-derived extracellular vesicles or their modifications can be applied to the development of a vaccine preventive or therapeutic of the infection of gut flora or a disease caused by the gut flora-derived extracellular vesicles because they can induce controlled immune responses when they are administered. Moreover, gut flora-derived extracellular vesicles are also utilized to develop a technology of diagnosing a pathogenic factor of the diseases caused by the gut flora-derived extracellular vesicles.

DESCRIPTION OF DRAWINGS

FIG. 1 summarizes gut flora bacteria identified by the mass analysis of the proteins of extracellular vesicles from mouse feces.

FIG. 2 is a TEM photograph of the extracellular vesicles isolated from the small intestinal fluid of a normal mouse.

*coli*-derived extracellular vesicles(EC_EV) (10, 20 μg) are stained with DiO and intraperitoneally injected.

Figure 28:
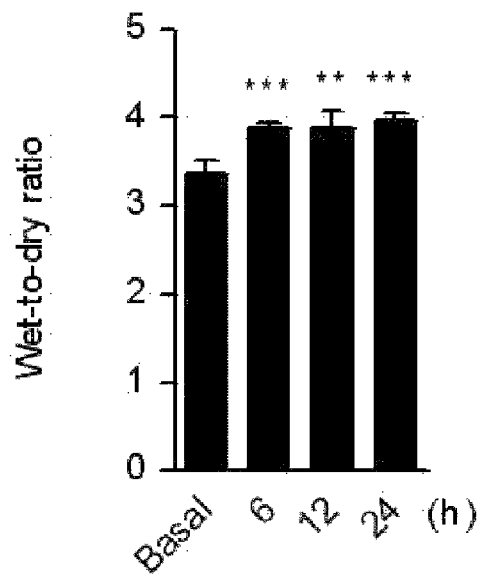

FIG. 28 is a graph showing the penetration of blood from vessels to the pulmonary tissue (wet-to-dry ratio) measured 6, 12 and 24 hours after three injections of 5 μg of *E. coli*-derived extracellular vesicles (EC_EV) at regular intervals of 12 hours.

Figure 29:
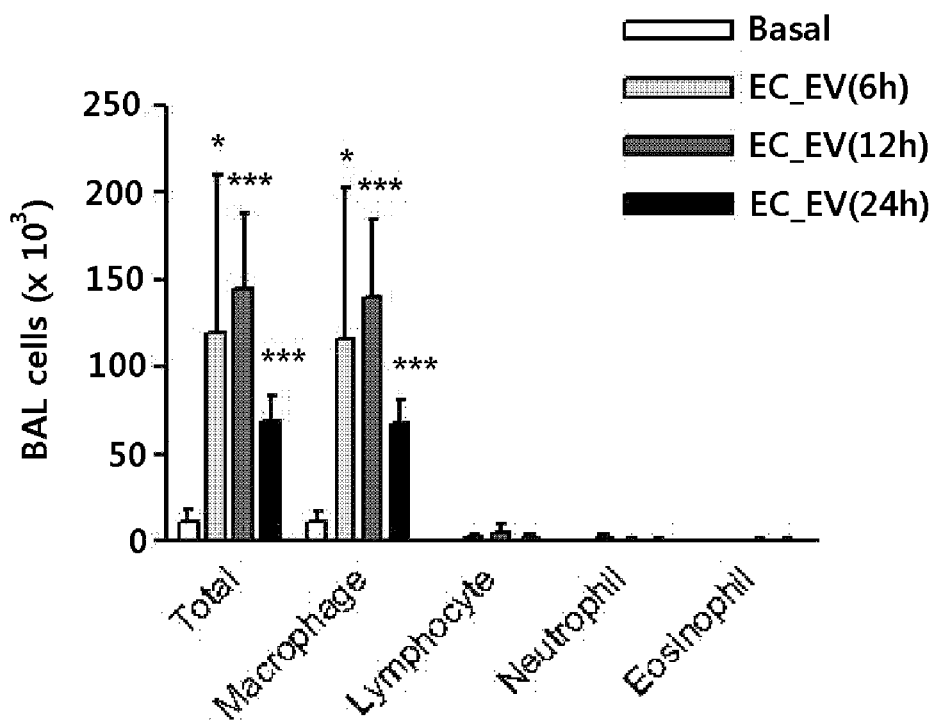

FIG. 29 is a graph showing inflammatory cell counts in BAL fluid measured 6, 12 and 24 hours after three injections of 5 μg of *E. coli*-derived extracellular vesicles (EC_EV) at regular intervals of 12 hours.

Figure 30:
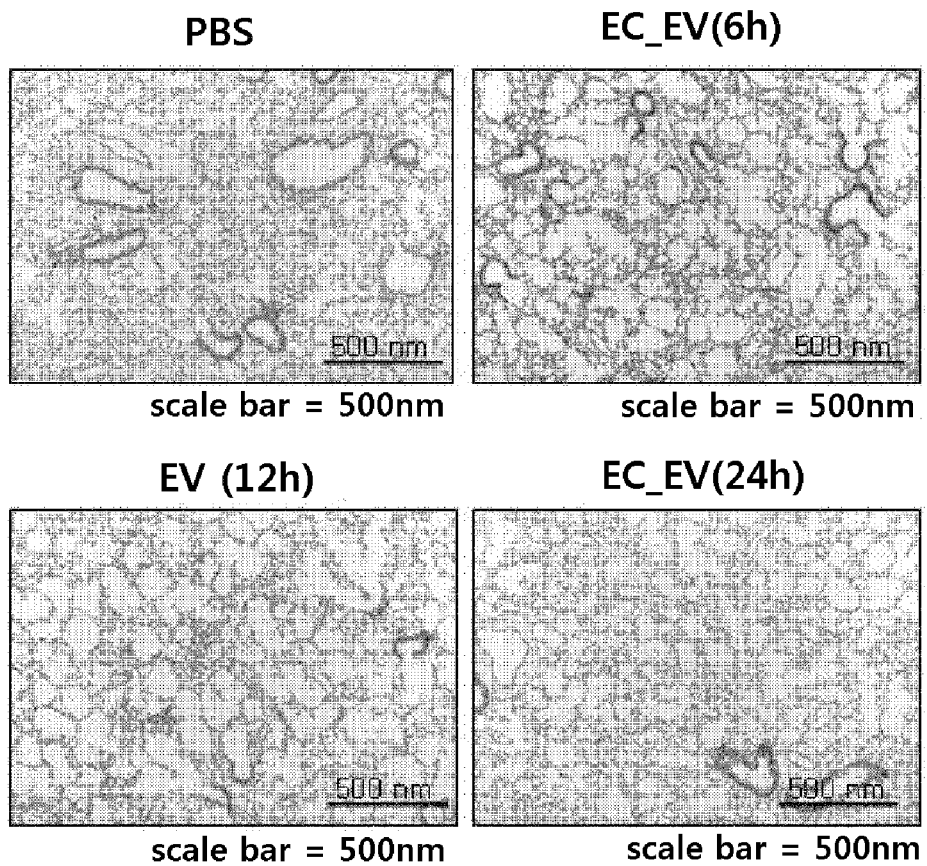

FIG. 30 shows optical images of pulmonary tissues prepared by excising the lungs 6, 12 and 24 hours after three injections of *E. coli*-derived extracellular vesicles (EC_EV) (5 μg) at regular intervals of 12 hours, fixing the lungs in 4% formaldehyde, slicing the lungs and staining the slices with hematoxylin-eosin.

Figure 31:
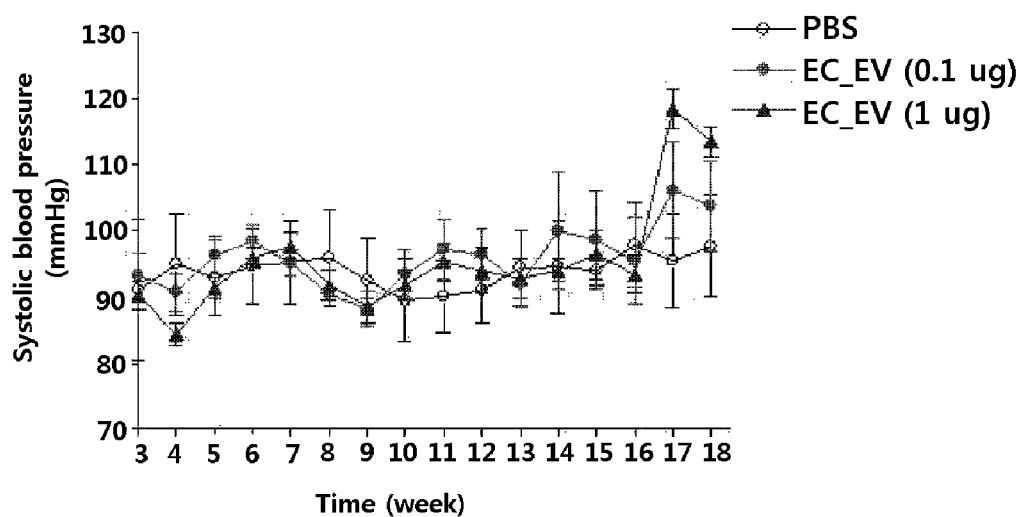

FIG. 31 is a graph showing changes in blood pressure upon repeated exposure twice a week for 18 weeks to 0.1 and 1 μg of *E. coli*-derived extracellular vesicles (EC_EV).

Figure 32:
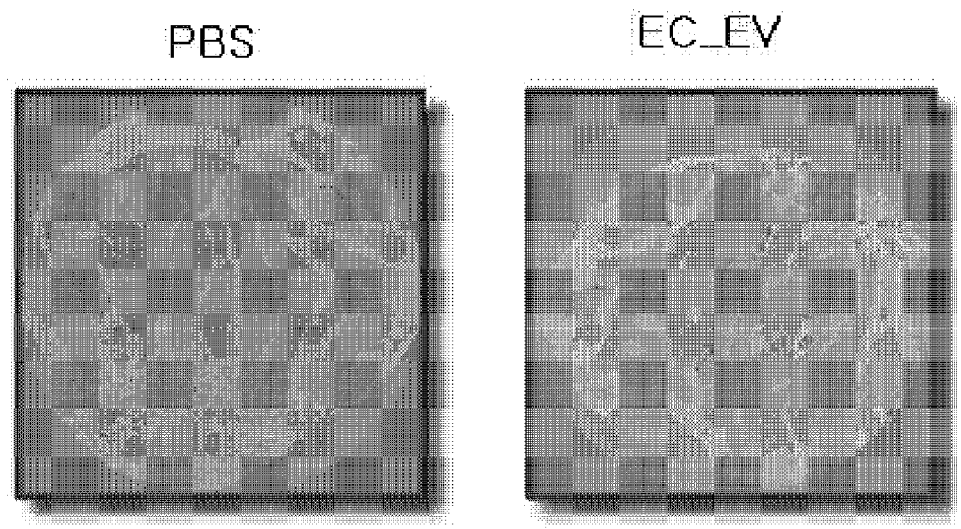

FIG. 32 shows long bones observed by X-ray technology after 1 μg of *E. coli*-derived extracellular vesicles (EC_EV) are injected twice a week for 18 weeks.

Figure 33:
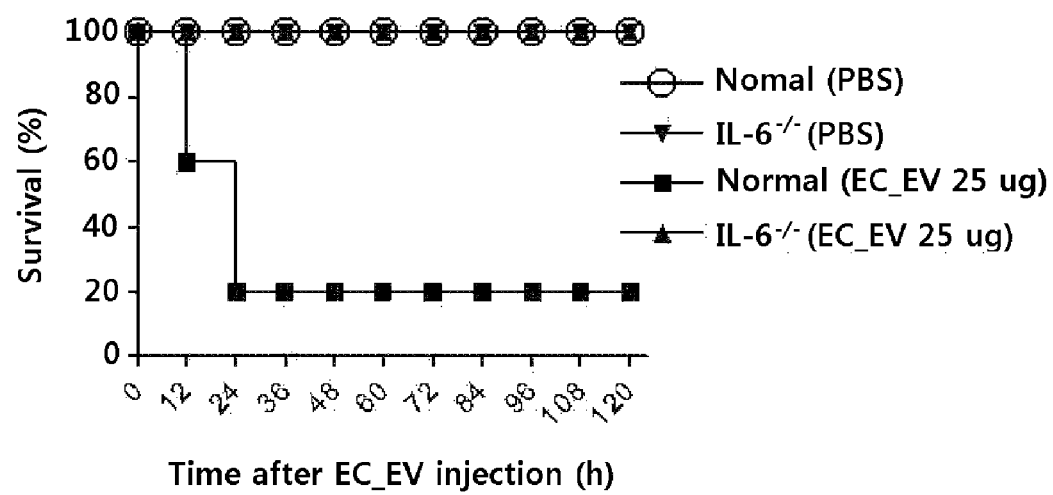

FIG. 33 shows survival rates of normal mice (C57BL/6, male, six weeks) and IL-6-knockout mice (C57BL/6, male, 6 weeks old) measured every 12 hours after they are intraperitoneally injected with 25 μg of *E. coli*-derived extracellular vesicles (EC_EV).

FIG. 34 shows optical photographs of lung slices, prepared by excising the lungs 6, 12 and 24 hours after three injections of *E. coli*-derived extracellular vesicles (EC_EV) (5 μg) at regular intervals of 12 hours to normal mice (C57BL/6, male, 6 weeks) and IL-6-knockout mice (C57BL/6, male, 6 weeks), fixing the lungs in 4% formaldehyde, slicing the lungs and staining the slices with hematoxylin-eosin.

Figure 35:
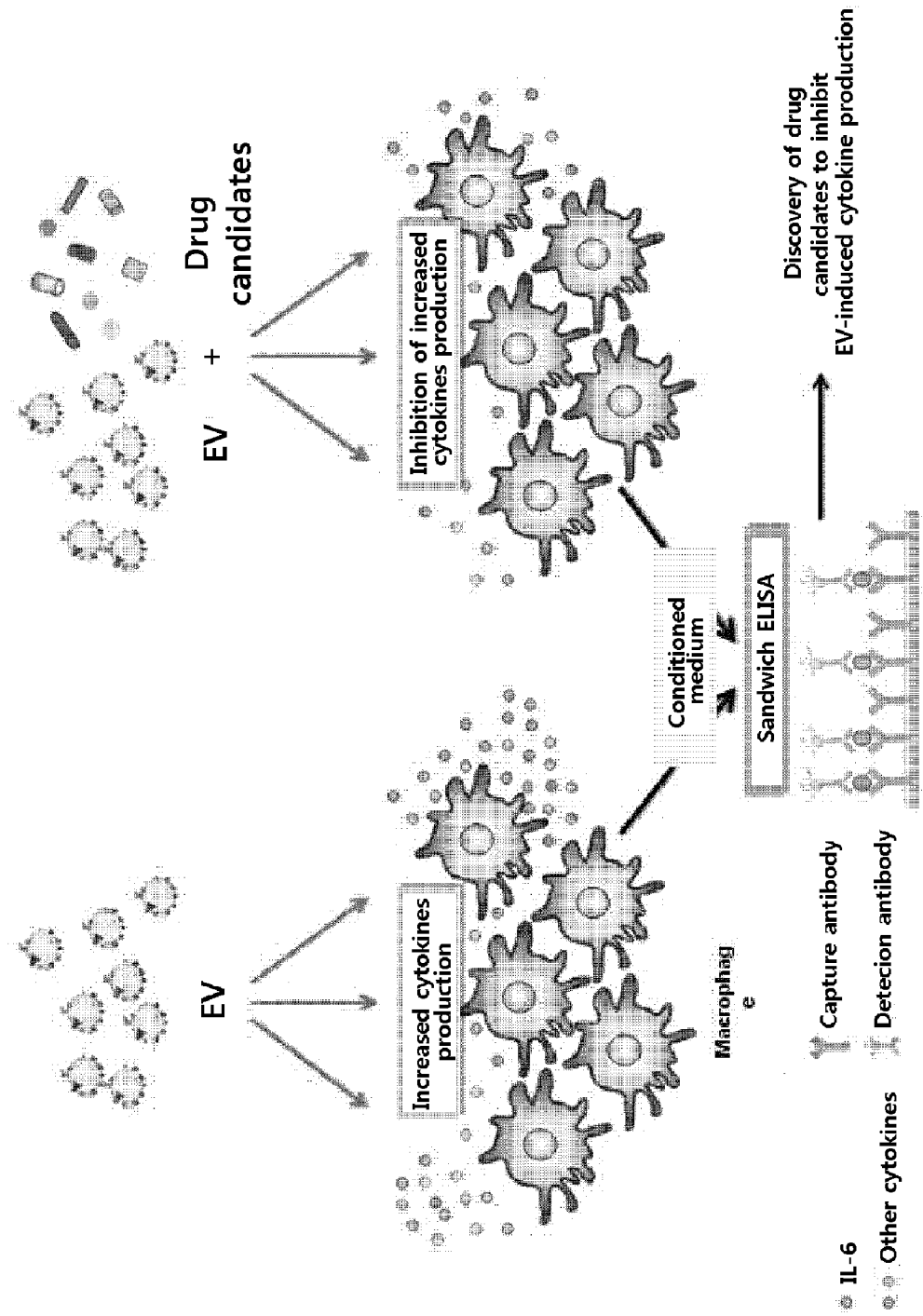

FIG. 35 is a schematic diagram showing the discovery of drug candidates using the gut flora-derived extracellular vesicles (EV).

Figure 36:
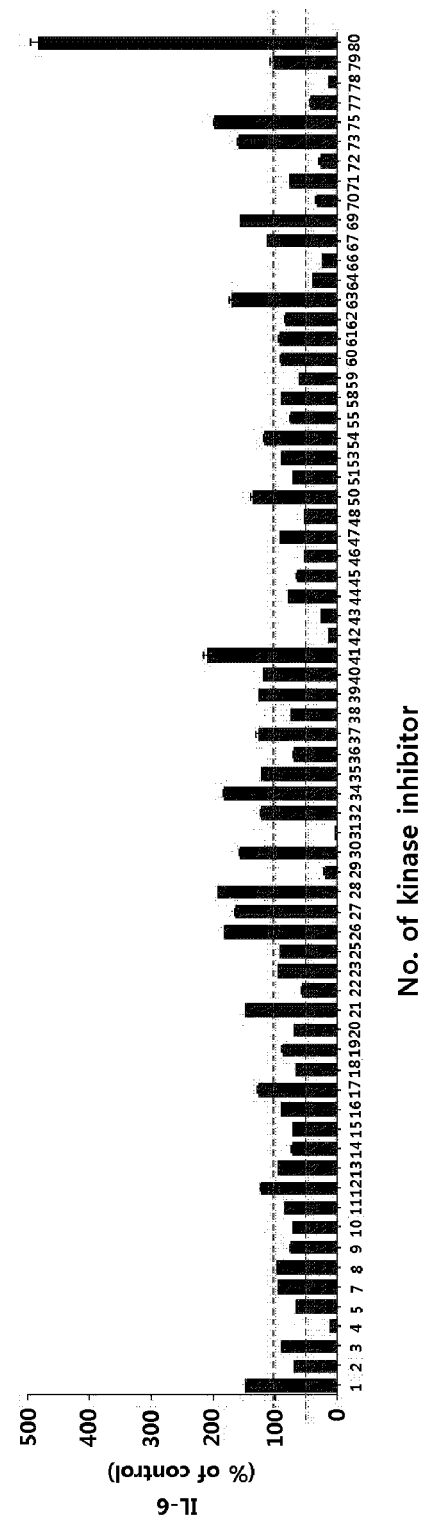

FIG. 36 is a graph showing the levels of IL-6 upon treatment with each of the kinase inhibitors in the presence of *E. coli*-derived extracellular vesicles (100 ng/ml), as percentages of that of the positive control treated with the extracellular vesicles alone.

Figure 37:
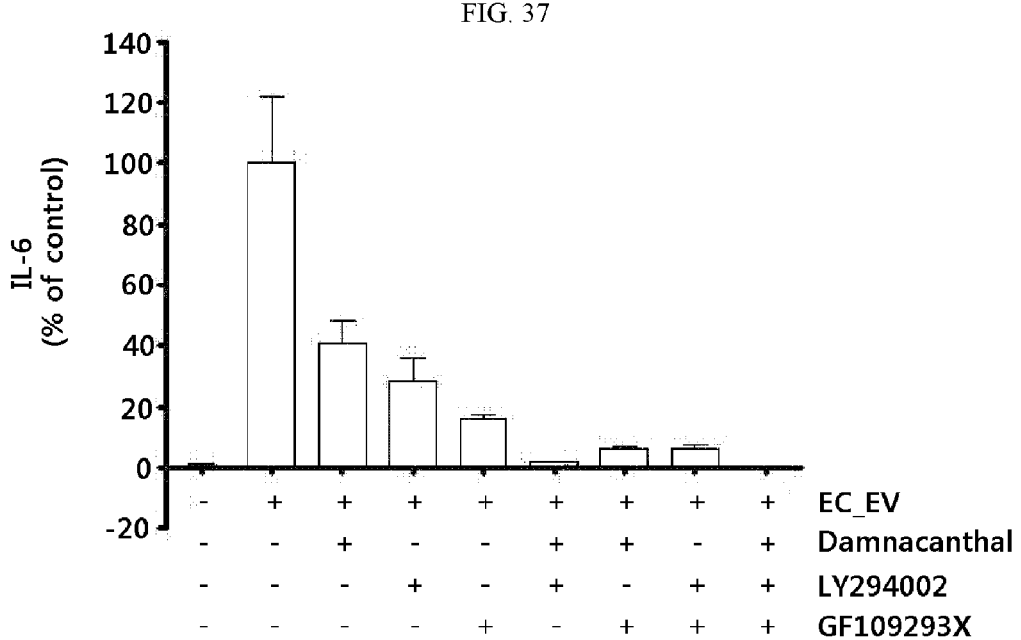

FIG. 37 is a graph of IL-6 levels in mouse macrophage cultures treated with one or more of the kinase inhibitors in the presence of *E. coli*-derived extracellular vesicles (EC_EV), as percentages of the positive control.

Figure 38:
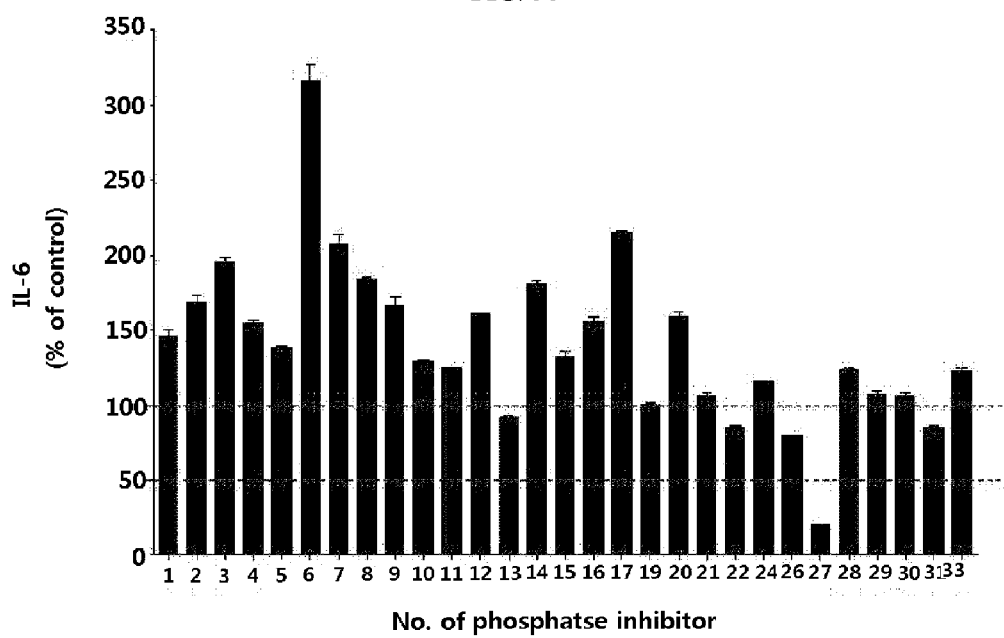

FIG. 38 is a graph showing IL-6 levels of the cell cultures as percentages of those of the positive control when the cell cultures were treated with phosphatase inhibitors (10 μM, 1; Cantharidic acid, 2; Cantharidin. 3; Endothall, 4; Benzylphosphonic acid, 5; L-p-Bromotetramisole oxalate, 6; RK-682, 7; RWJ-60475, 8; RWJ-60475 (AM)3, 9; Levamisole HCl, 10; Tetramisole HCl, 11; Cypermethrin, 12; Deltamethrin, 13; Fenvalerate, 14; Tyrphostin 8, 15; CinnGEL, 16; CinnGEL 2 Me, 17; BN-82002, 19; NSC-663284, 20; Cyclosporin A, 21; Pentamidine, 22; BVT-948, 24; BML-268, 26; BML-260, 27; PD-144795, 28; BML-267, 29; BML-267 Ester, 30; OBA, 31; OBA Ester, 33; Alendronate) in the presence of *E. coli*-derived extracellular vesicles (100 ng/ml)

Figure 39:
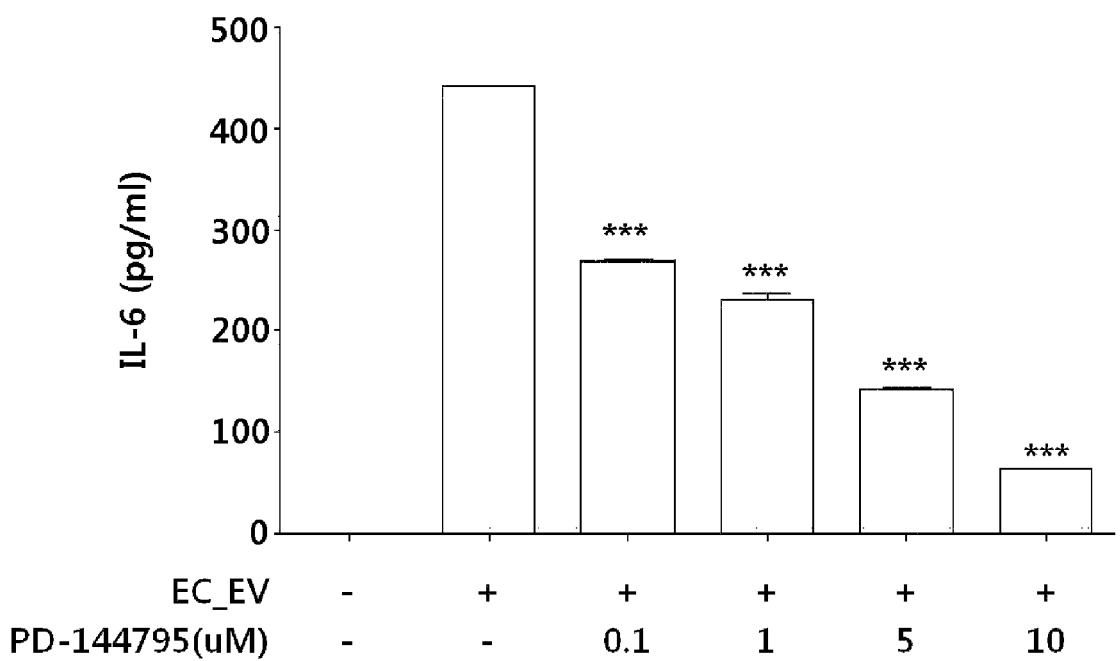

FIG. 39 is a graph of IL-6 levels in mouse macrophage cultures that were treated with 0.1, 1, 5, and 10 μM PD-144795 in the presence of *E. coli*-derived extracellular vesicles (EC gV).

Figure 40:
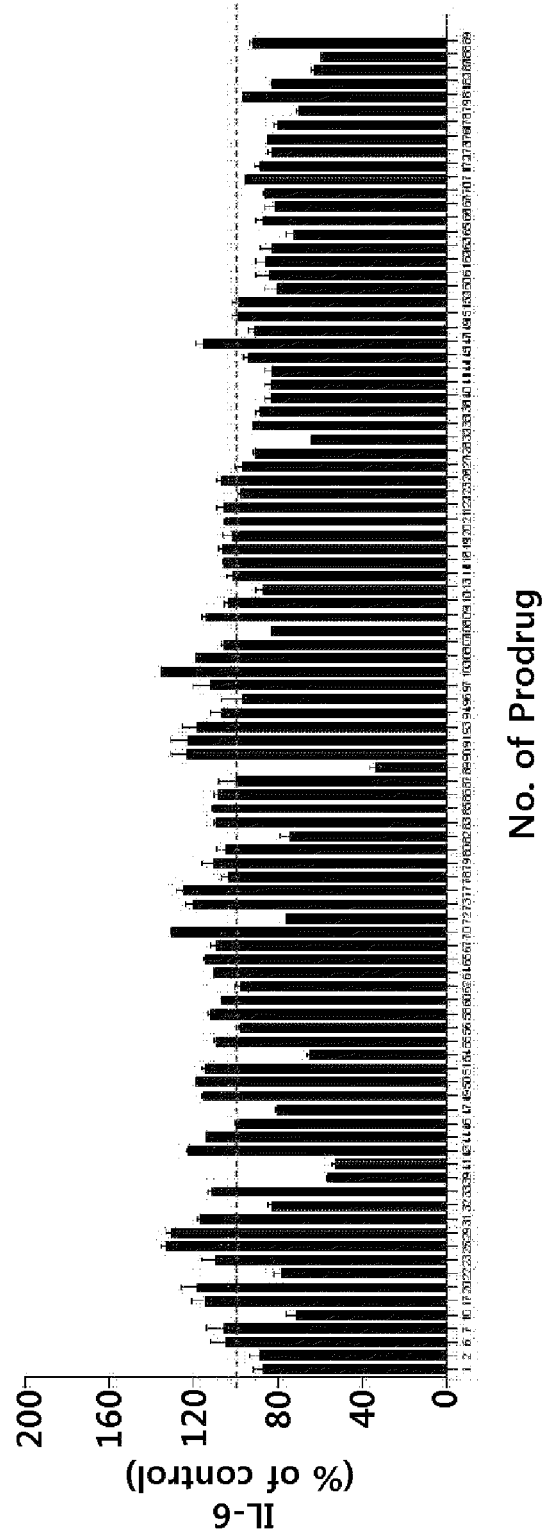

FIG. 40 is a graph showing IL-6 levels of the cell cultures as percentages of those of the positive control when the cell cultures were treated with prodrugs in the presence of *E. coli*-derived extracellular vesicles (100 ng/ml).

Figure 41:
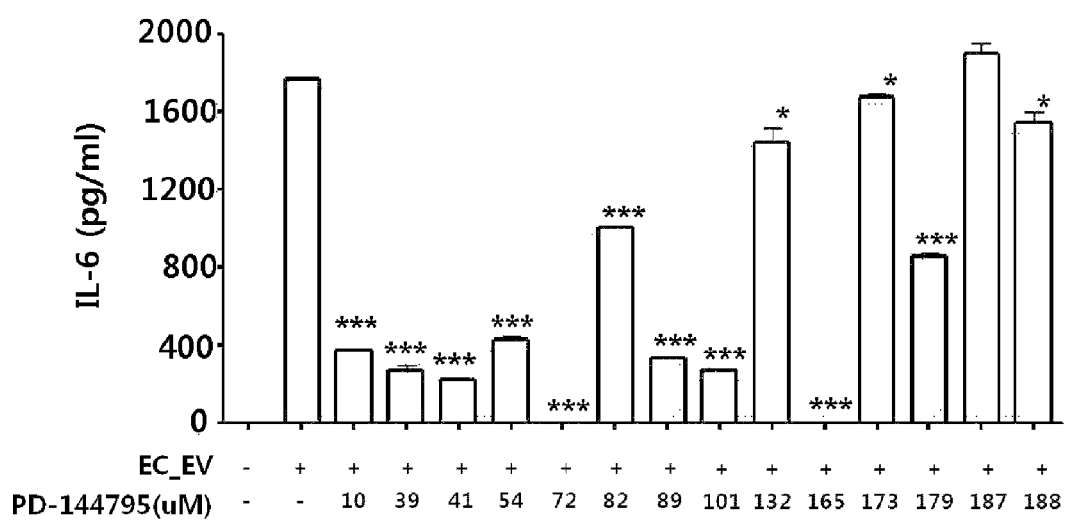

FIG. 41 is a graph showing IL-6 levels obtained by treating mouse peritoneal macrophages with 10 μM prodrugs in the presence of *E. coli*-derived extracellular vesicles(EC_EV)

Figure 42:
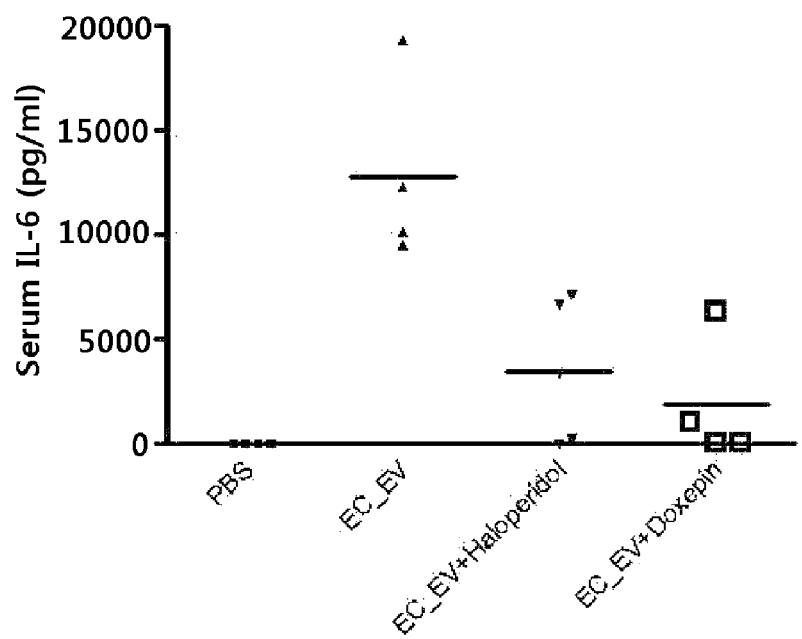

FIG. 42 is a graph showing serum IL-6 levels measured after the mice systemically immunized by intraperitoneally injecting 5 μg of *E. coli*-derived extracellular vesicles(EC_EV) were administered with 10 mg/kg of the prodrug haloperitol or doxepin by intraperitoneal injection.

Figure 43:
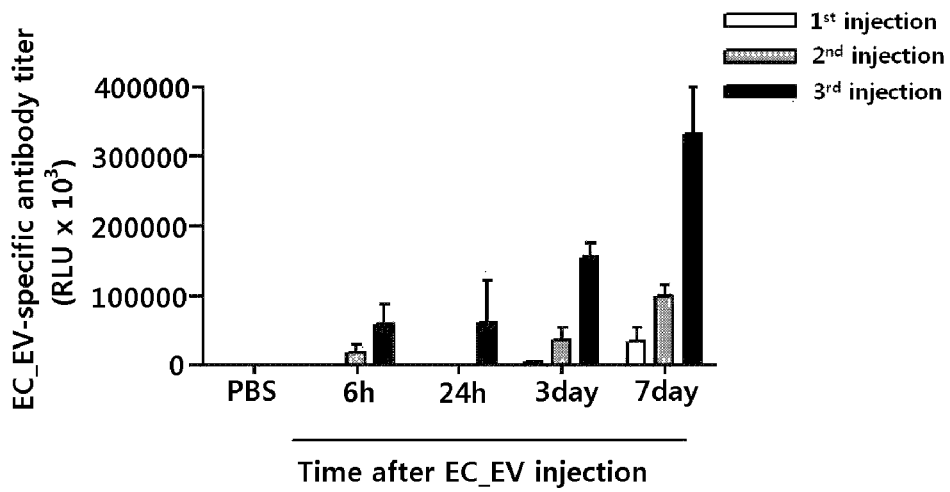

FIG. 43 is a graph showing the levels of vesicle-specific antibodies measured in the course of three intraperitoneal injections of 1 μg of *E. coli*-derived extracellular vesicles (EC_EV) at regular intervals of one week.

Figure 44:
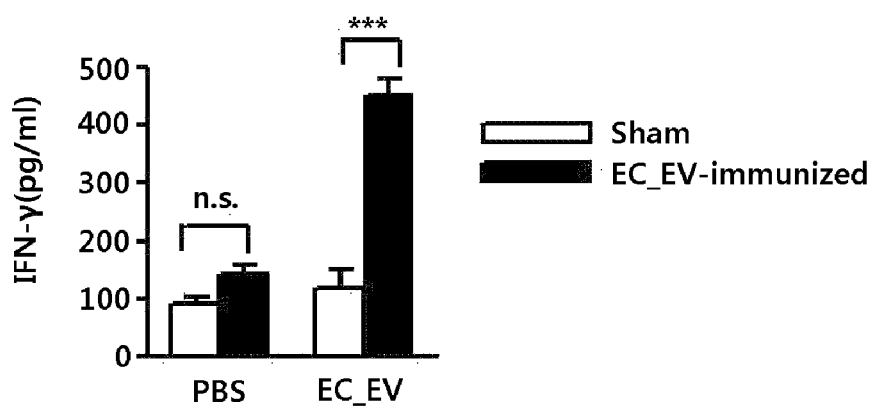

FIG. 44 shows the levels of IFN-γ secreted from mouse splenocytes upon ex vivo treatment with *E. coli*-derived extracellular vesicles after the mice were immunized with the *E. coli*-derived extracellular vesicle (EC_EV) vaccine.

Figure 45:
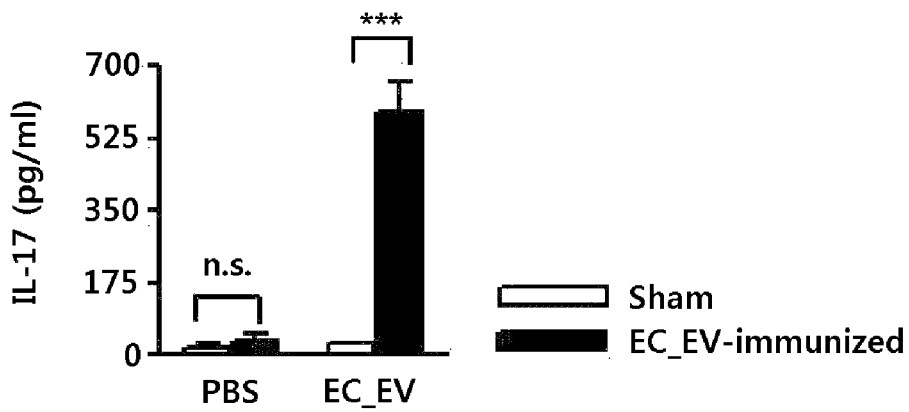

FIG. 45 shows the levels of IL-17 secreted from mouse splenocytes upon ex vivo treatment with *E. coli*-derived extracellular vesicles after the mice were immunized with the *E. coli*-derived extracellular vesicle (EC_EV) vaccine.

Figure 46:
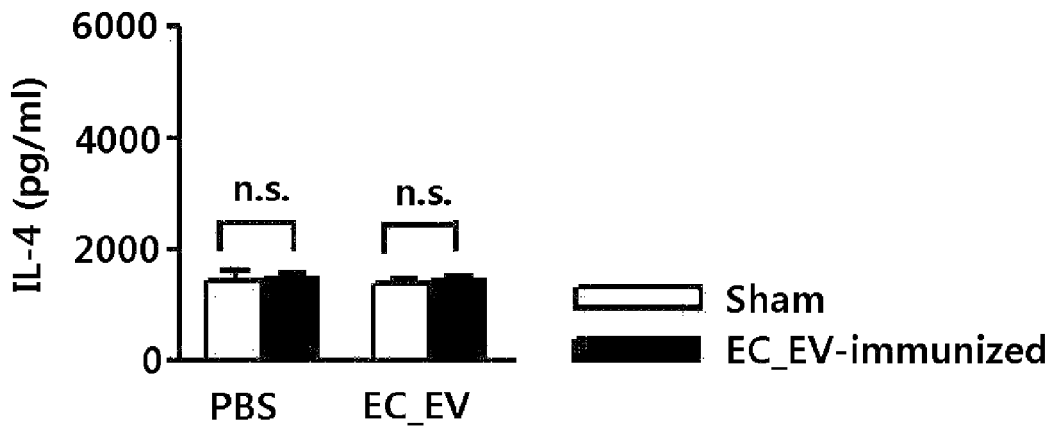

FIG. 46 shows the levels of IL-4 secreted from mouse splenocytes upon ex vivo treatment with *E. coli*-derived extracellular vesicles after the mice were immunized with the *E. coli*-derived extracellular vesicle (EC_EV) vaccine.

Figure 47:
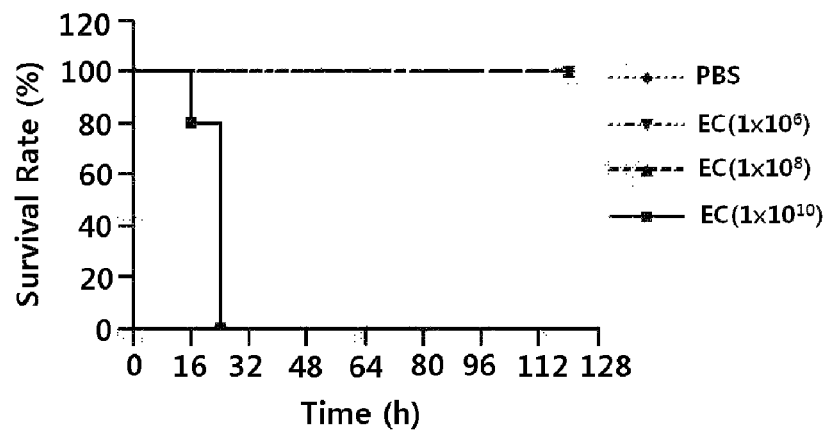

FIG. 47 shows survival rates of the mice in which sepsis was induced by the intraperitoneal injection of *E. coli* (EC).

Figure 48:
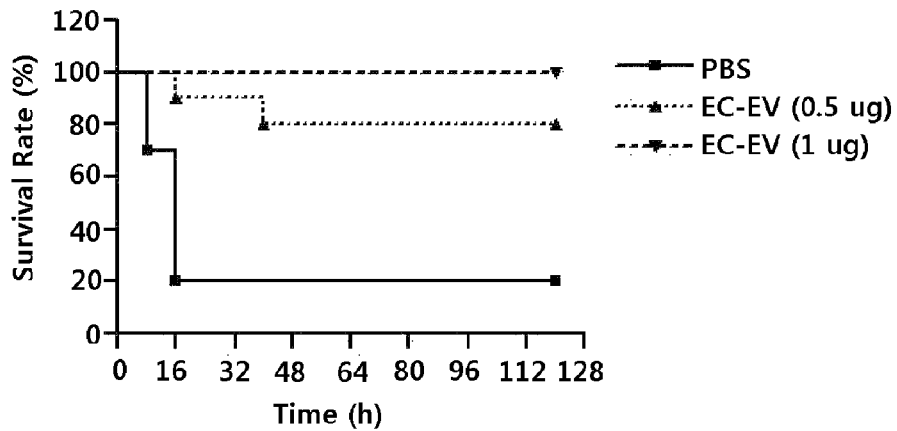

FIG. 48 shows the efficacy of the *E. coli*-derived extracellular vesicle (EC_EV) vaccines against the *E. coli* (EC) infection-induced sepsis.

Figure 49:
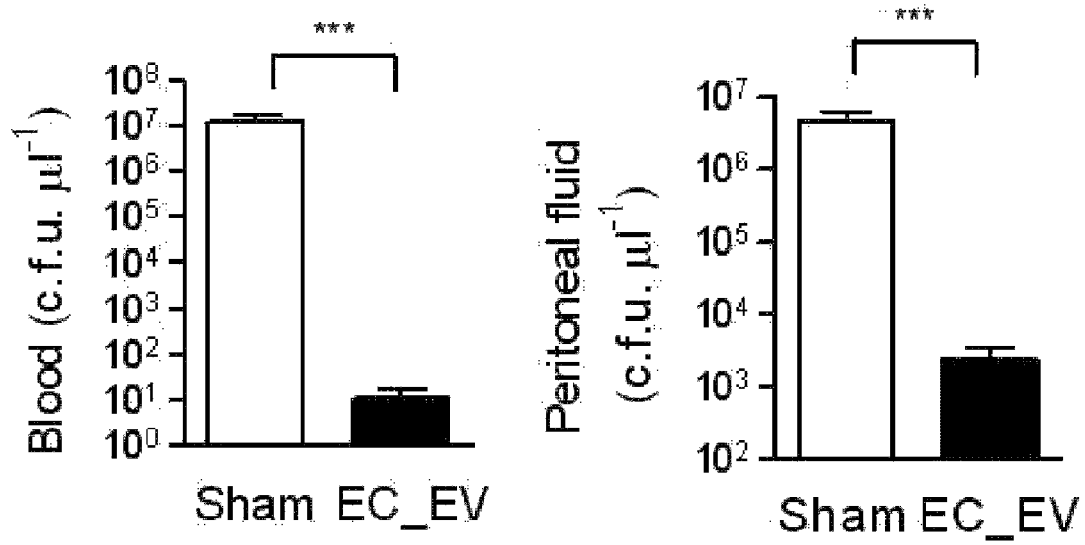

FIG. 49 shows *E. coli* CFU in mice immunized with and without *E. coli*-derived extracellular vesicles (EC_EV) upon the intraperitoneal injection of *E. coli* (EC).

Figure 50:
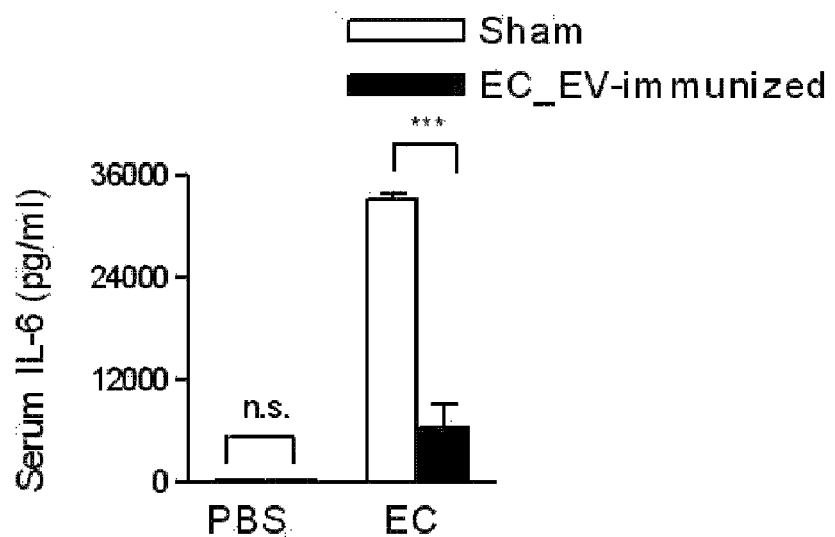

FIG. 50 shows blood IL-6 levels of mice immunized with or without *E. coli*-derived extracellular vesicles (EC_EV) as measured 6 hours after intraperitoneal infection with *E. coli* (EC).

Figure 51:
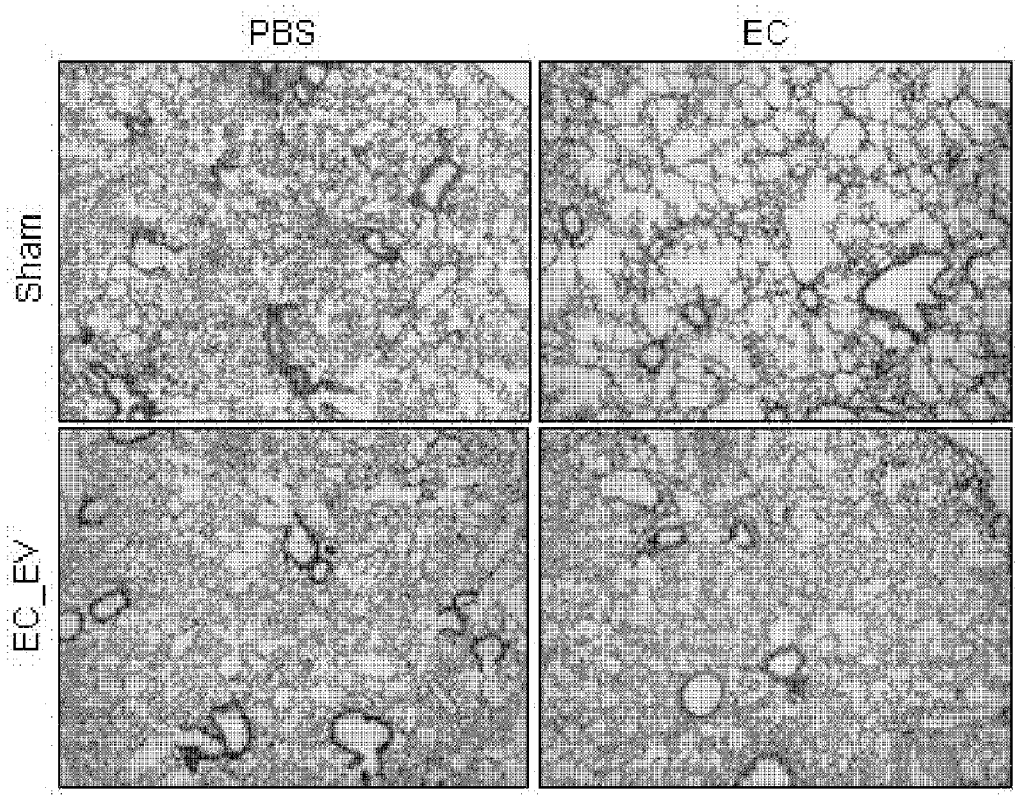

FIG. 51 shows images of the lung tissues excised 6 hours after *E. coli* (EC) was intraperitoneally infected into mice that has been immunized with or without *E. coli*-derived extracellular vesicles(EC_EV).

Figure 52:
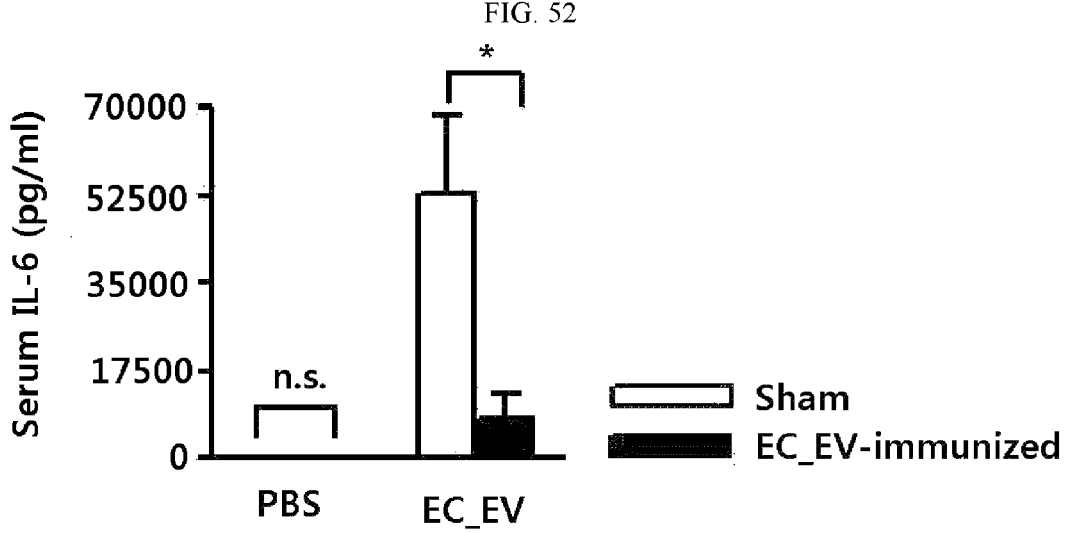

FIG. 52 shows blood IL-6 levels measured 6 hours after three introperitoneal injections of *E. coli*-derived extracellular vesicles (5 μg) into mice immunized with or without (EC_EV).

Figure 53:
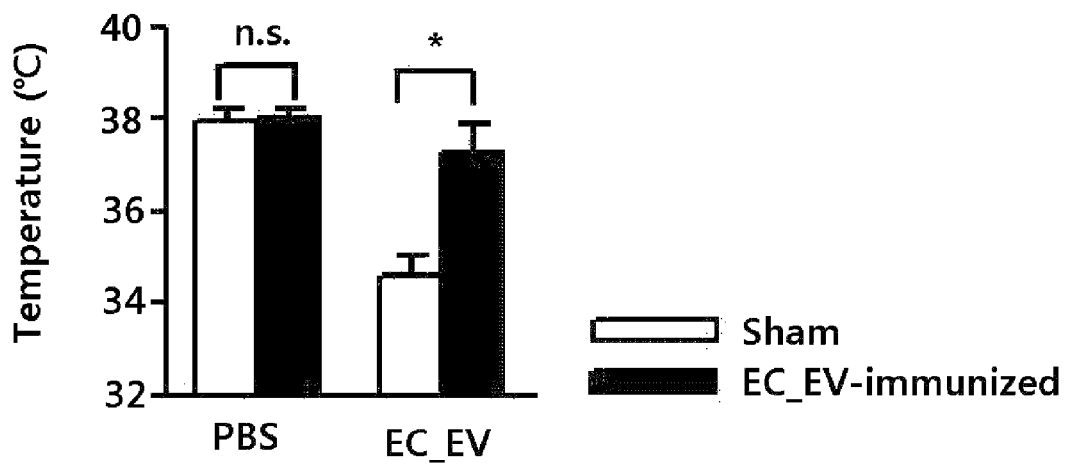

FIG. 53 shows a change in the systemic inflammation index body temperature measured 6 hours after three introperitoneal injections of *E. coli*-derived extracellular vesicles (5 μg) into mice immunized with or without (EC_EV).

Figure 54:
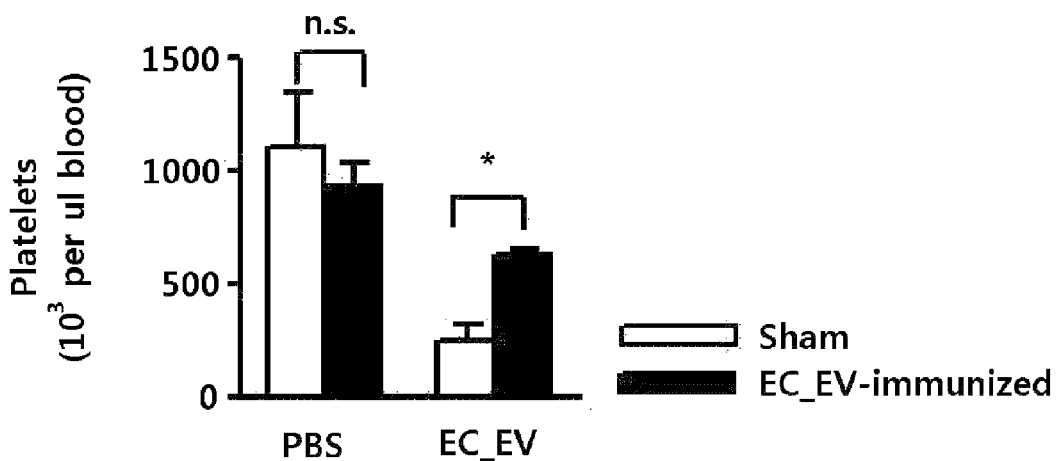

FIG. 54 shows thrombocytopenia, an index for disseminated intravascular coagulation, measured (DIC), measured 6 hours after three introperitoneal injections of *E. coli*-derived extracellular vesicles (5 μg) into mice immunized with or without (EC_EV).

Figure 55:
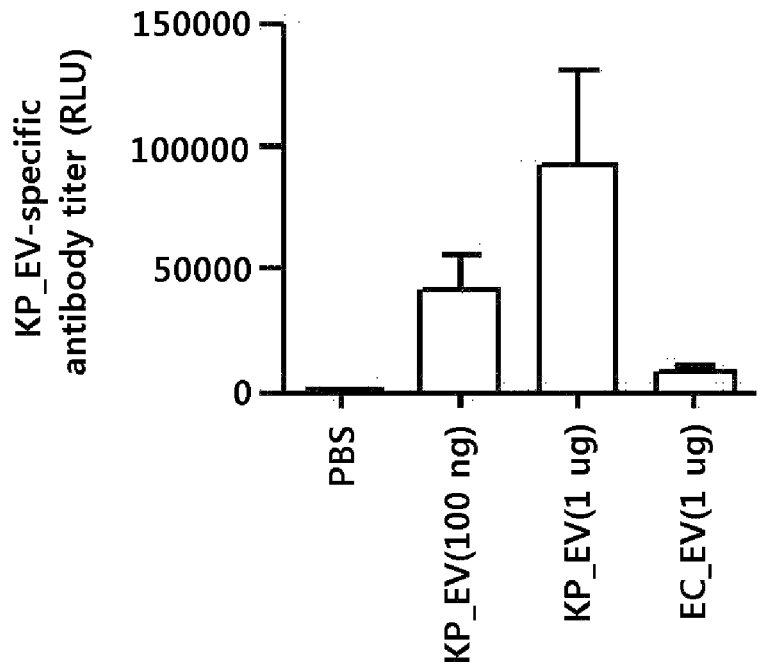

FIG. 55 is a graph showing the production of *Klebsiella*-derived extracellular vesicle-specific antibodies in the blood taken from mice immunized with *Klebsiella*-derived extracellular vesicles (KP_EV).

Figure 56:
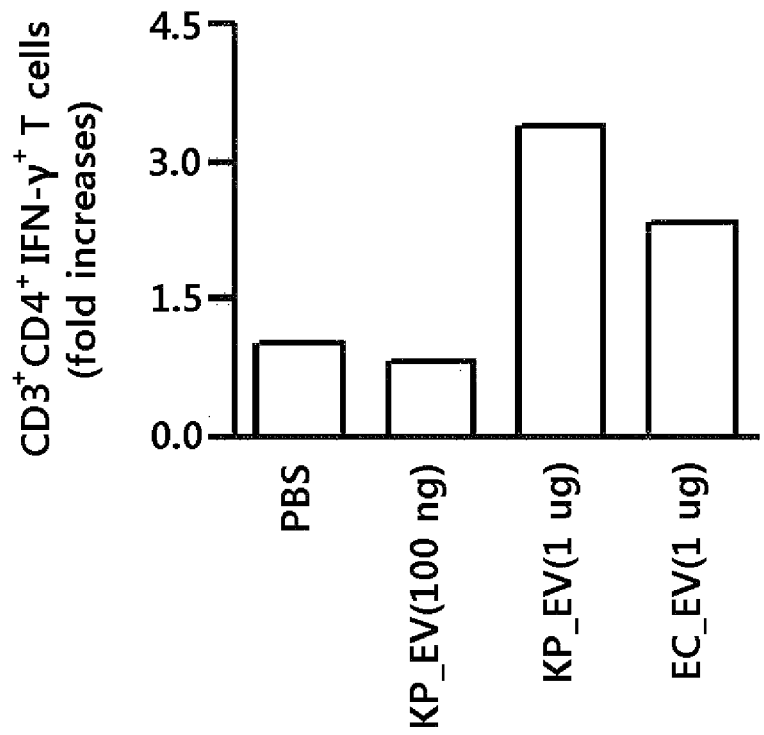

FIG. 56 is a graph showing a change in the population of CD3$^+$CD4$^+$IFN-γ$^+$ T cells out of spleen T cells of *Klebsiella*-derived extracellular vesicle (KP_EV)-immunized mice upon ex vivo treatment with *Klebsiella*-derived extracellular vesicles (KP_EV).

Figure 57:
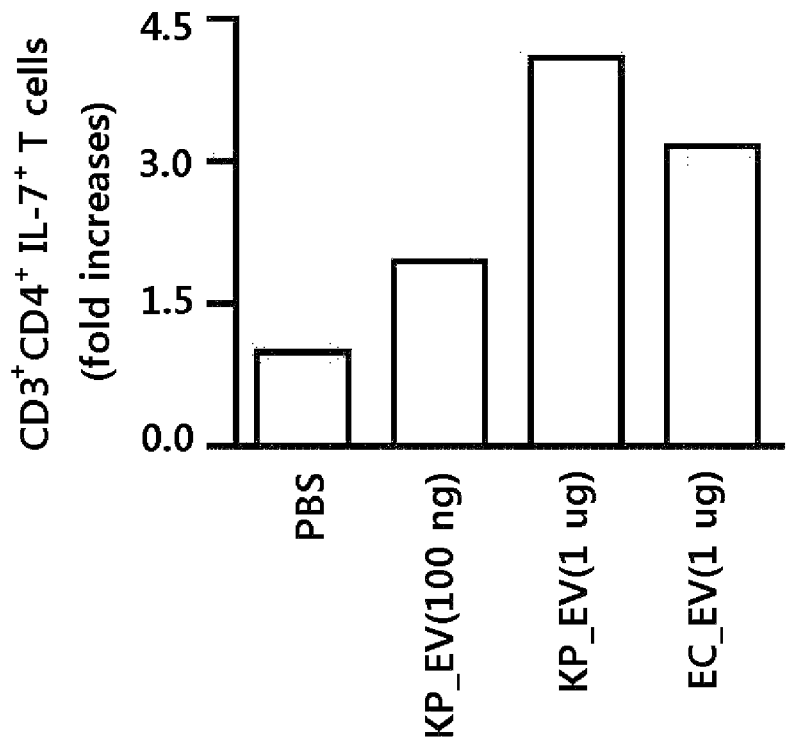

FIG. 57 is a graph showing a change in the population of CD3$^+$CD4$^+$IL17$^+$ T cells out of spleen T cells of *Klebsiella*- derived extracellular vesicle (KP_EV)-immunized mice after treatment with *Klebsiella*-derived extracellular vesicles (KP_EV).

Figure 58:
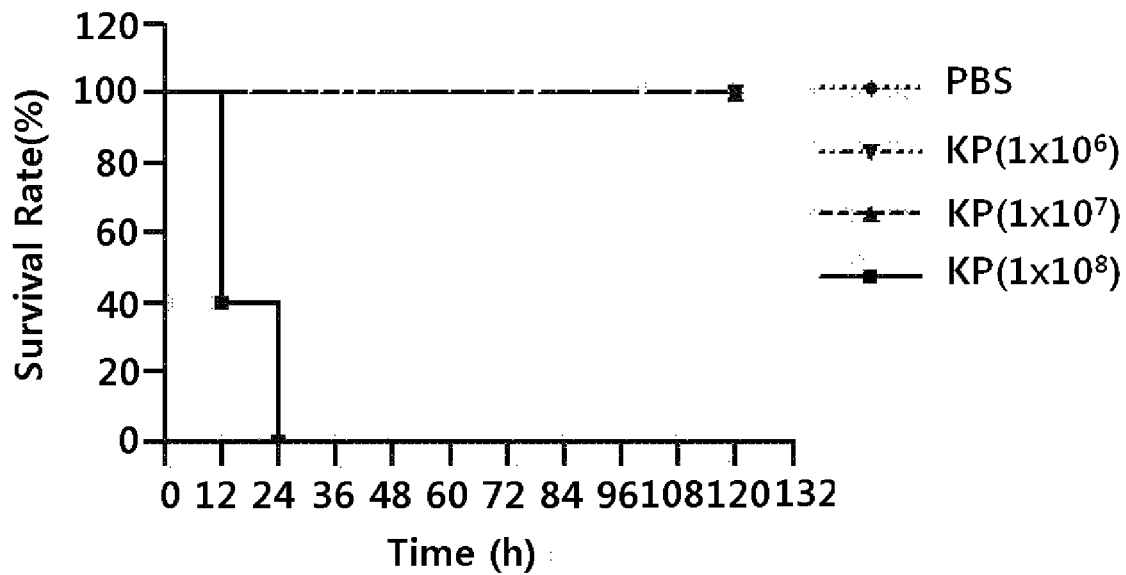

FIG. 58 shows survival rates of the mice in which sepsie was induced by intraperitoneal injection of *Klebsiella* (KP).

Figure 59:
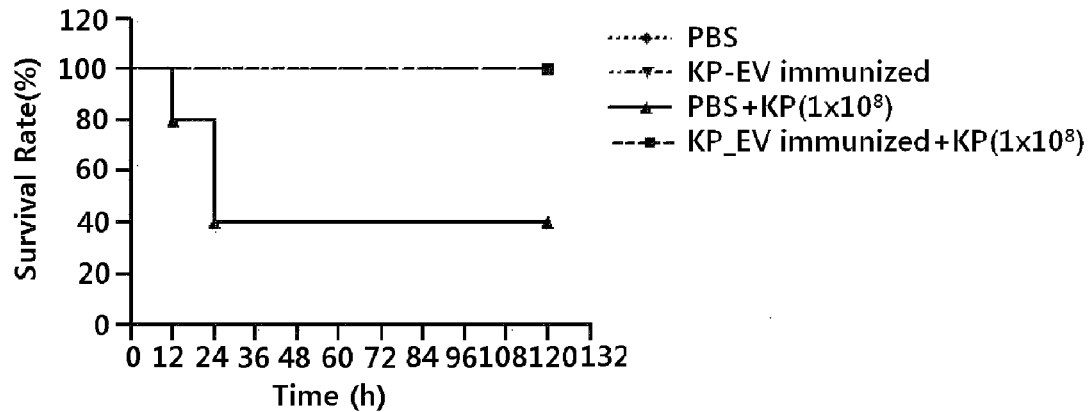

FIG. 59 shows the efficacy of the *Klebsiella*-derived extracellular vesicle (KP_EV) vaccines against the sepsis that was induced by three intraperitoneal injections of *Klebsiella* (KP).

Figure 60:
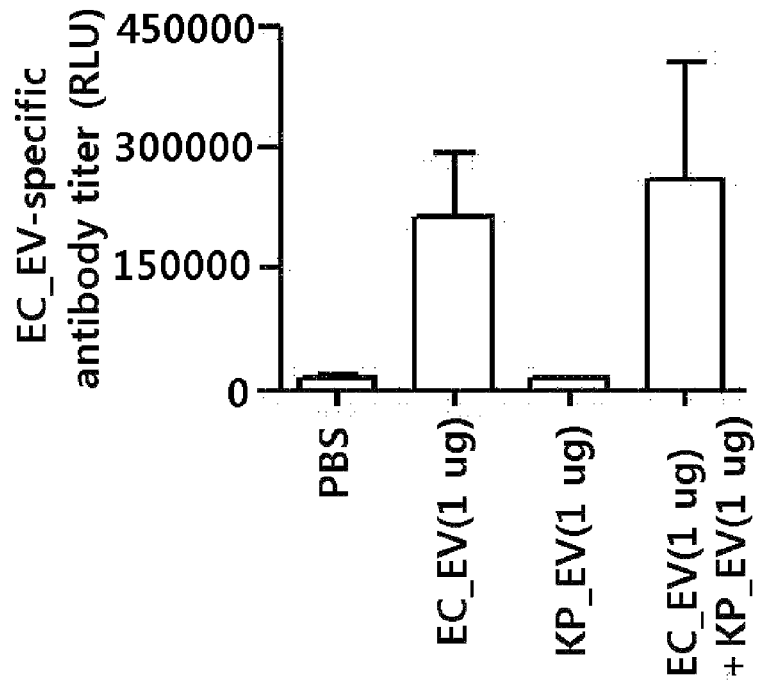
Figure 61:
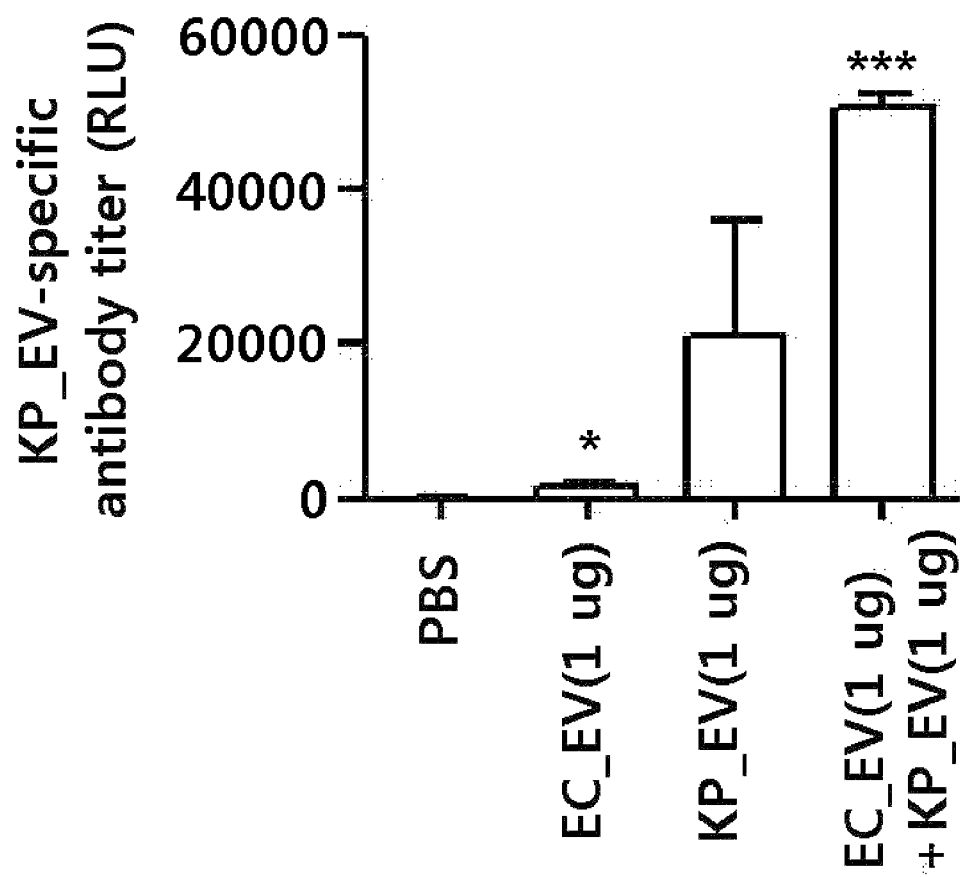

FIG. 60 is a graph showing the production of *E. coli*-derived extracellular vesicle-specific antibodies in the mice immunized with a combination of *E. coli*- and *Klebsiella*-derived extracellular vesicles (EC_EV, KP_EV) vaccines FIG. 61 is a graph showing the production of *Klebsiella*-derived extracellular vesicle-specific antibodies in the mice immunized with a combination of *E. coli*- and *Klebsiella*-derived extracellular vesicles (EC_EV, KP_EV) vaccines.

Figure 62:
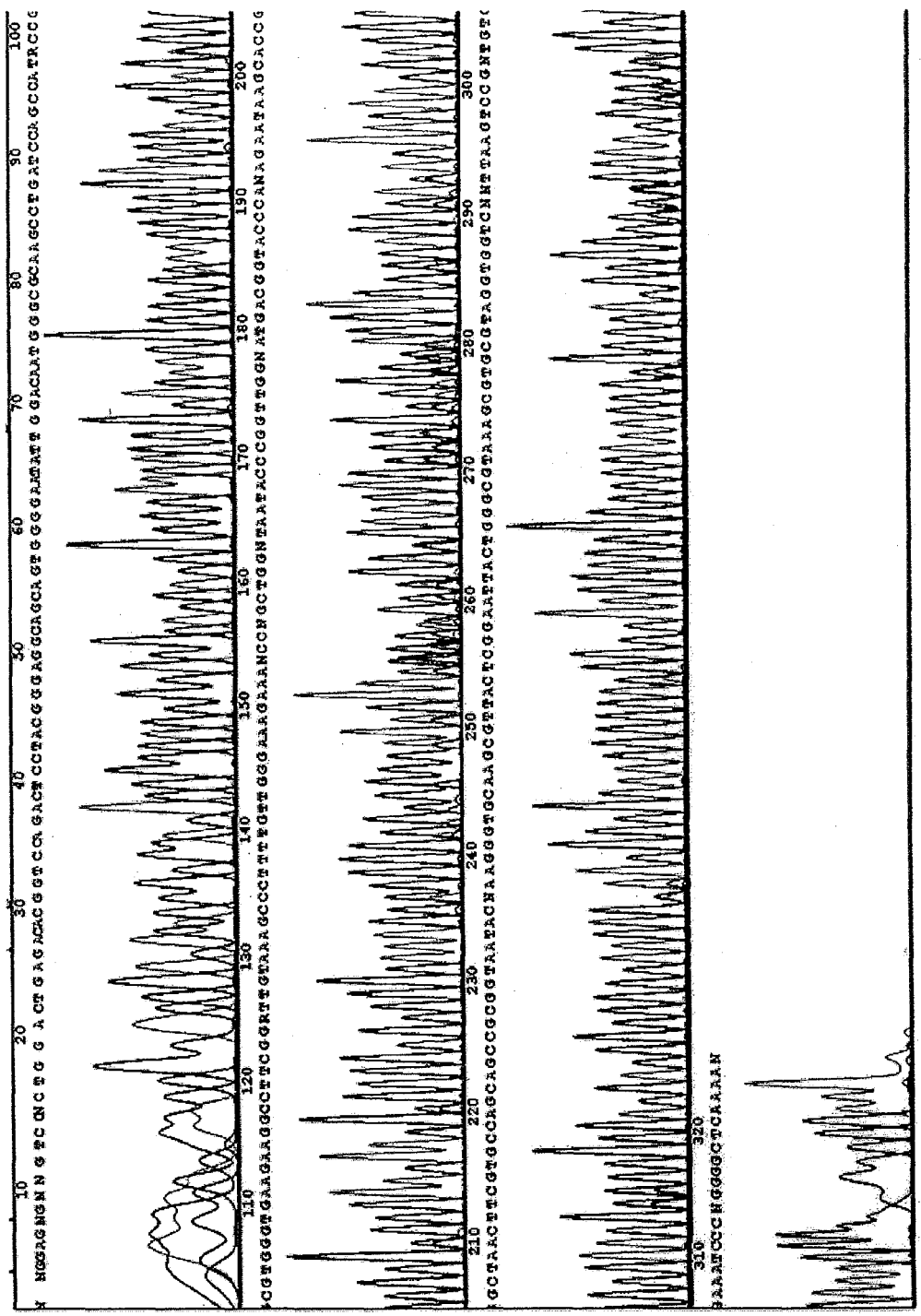

FIG. 62 is a base sequence analysis result of a genetic substance of the extracellular vesicles from C57BL/6 mouse feces (SEQ ID NO. 2).

Figure 63:
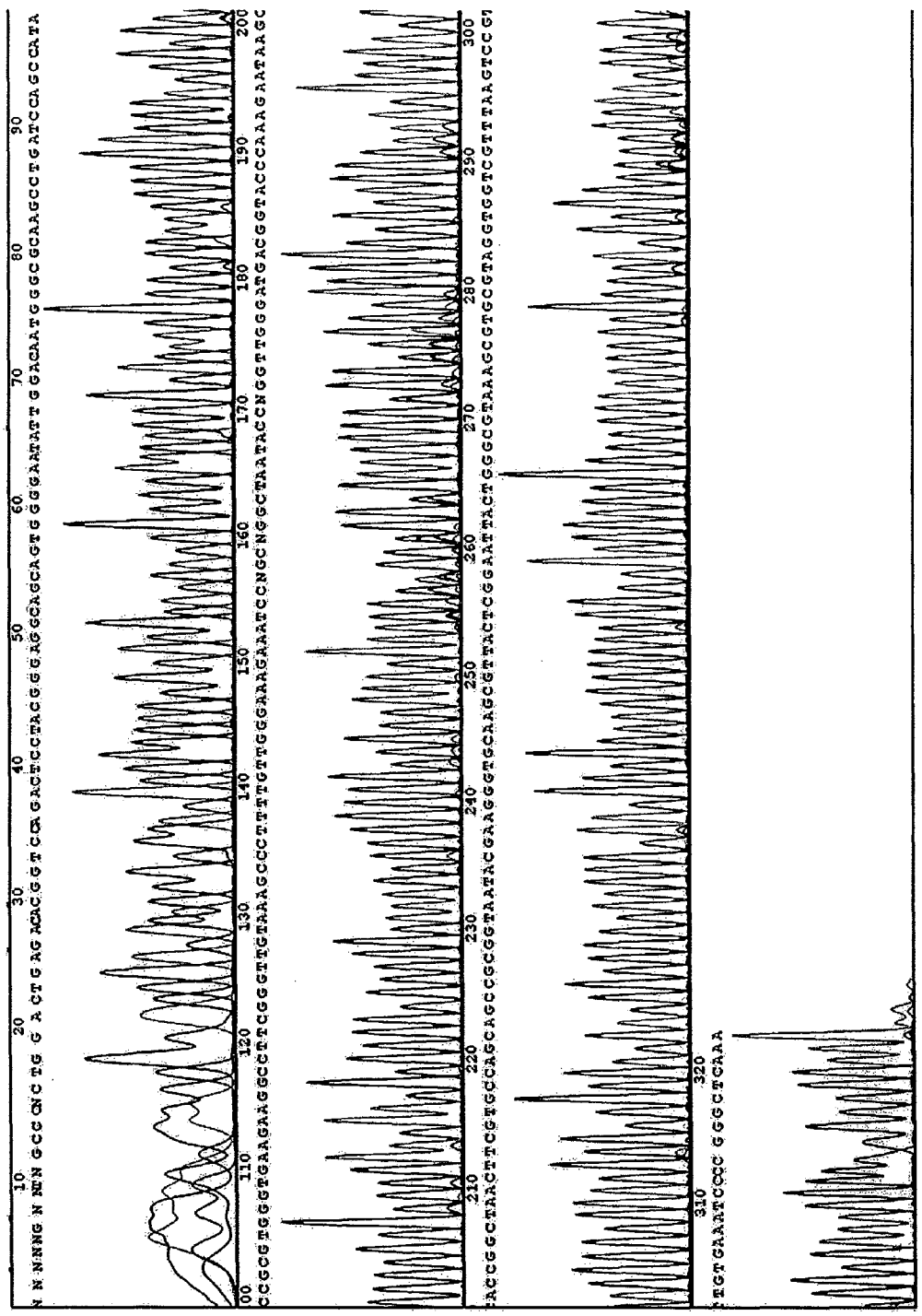

FIG. 63 is a base sequence analysis result of a genetic substance of the extracellular vesicles from BALB/c mouse feces (SEQ ID NO. 3).

Figure 64:
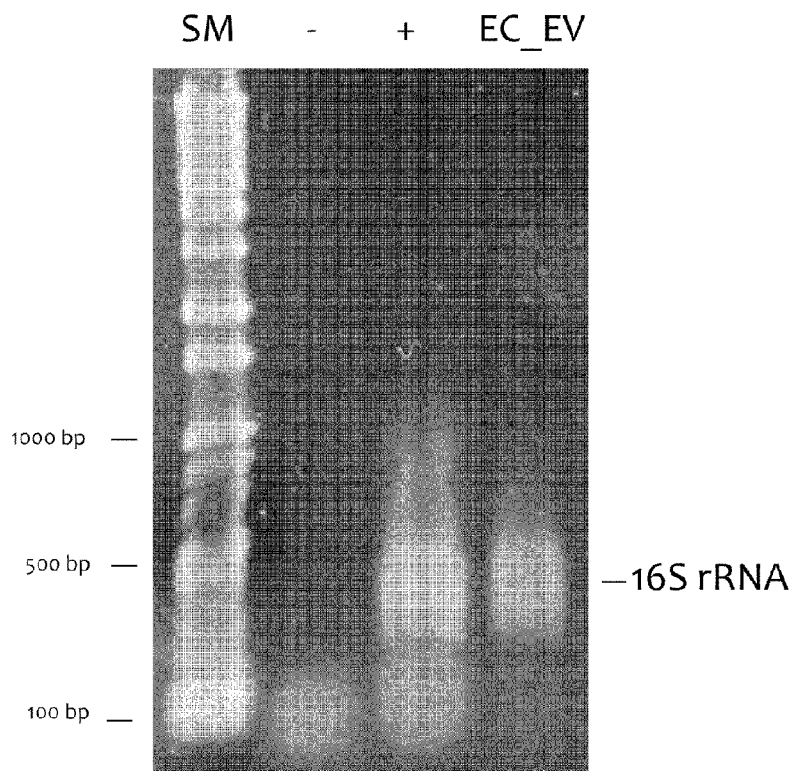

FIG. 64 shows the presence of a 16S rRNA gene or its RNA transcription in *E. coli*-derived extracellular vesicles (EC_EV) as analyzed by RT-PCR using a bacteria-universal primer.

Figure 65:
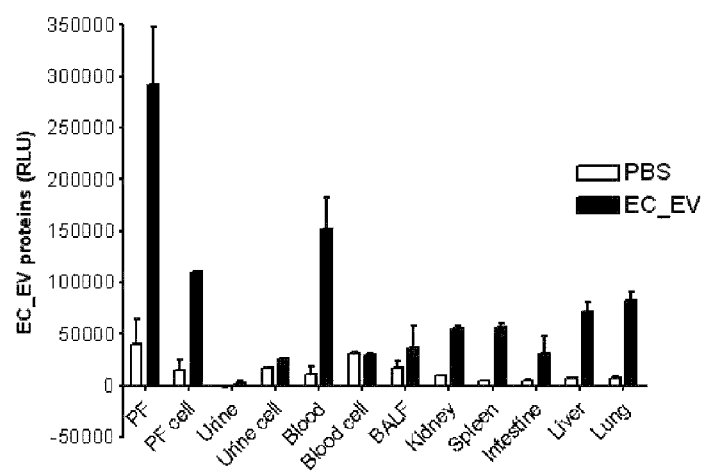

FIG. 65 shows the presence of intraperitoneally injected extracellular vesicles in various organs and body fluids taken from mouse groups intraperitoneally injected with 25 µg of *E. coli*-derived extracellular vesicles (EC_EV) or PBS.

BEST MODE

The present invention contemplates gut flora-derived extracellular vesicles, and the uses thereof in establishing a disease model, a vaccine, a screening method for candidate drugs, and a diagnostic method.

As used herein, the term "gut" is intended to encompass the lining and epithelial layer surface of the mammal digestive tracts. For example, linings and epithelial layer surfaces of the mouth, the esophagus, the stomach, the small intestine, the large intestine, the rectum, the anus, the bile duct, the cystic duct, and the pancreatic duct fall within the scope of the gut, but the present invention is not limited to these.

As used herein, the term "gut microbiota" or "gut flora" refers to the collective bacteria that inhabit the cavities or linings of mammal digestive tracts. In a normal state, they do not cause diseases, but in a low immune state or when they depart from the routine tracts, the bacteria may cause diseases. The human flora known to those skilled in the art is among the gut flora of the present invention, but is an illustrative, non-limiting example.

The term "gut flora-derived extracellular vesicles," as used herein, is intended to encompass vesicles secreted from gut flora, whether present in the linings or within tissues. Typically, vesicles are smaller in size than their source cells, but this does not limit the scope of the present invention in any way.

Gut flora has been out of the subject of interest as pathogens. In connection with bacterial intestinal infection, attention has been paid mostly into acute infectious diseases, most of which are generated upon the intake of pathogen-contaminated foods. Recently, the *helicobacter* bacteria found living in the lining of the upper gastrointestinal tract have attracted strong attention with regard to the onset of gastritis, duodenal ulcer, and stomach cancer. In addition, bacteria which live in the large intestine are suspected to be involved in the onset of inflammatory bowel disease and colorectal cancer. However, gut flora-derived extracellular vesicles have not yet been pointed out as a cause of the above-mentioned gastrointestinal diseases.

The present inventors first revealed that gut flora-derived extracellular vesicles induce mucosal inflammation and particularly provoke the Th17 immune response characterized by neutrophilic inflammation, which plays an important role in the etiology of cancer, and on the basis of this revelation, locally injected the gut flora-derived extracellular vesicles to construct an animal model for the localized disease.

With regard to the etiology of sepsis, characterized by systemic inflammation, it is known that a substance derived from bacteria is absorbed into blood to cause the disease, but the actual entity has remained elusive. Also, the present first discovered that when introduced into blood vessels, gut flora-derived extracellular vesicles induce the release of an inflammatory mediator, resulting in the onset of sepsis, characterized by systemic inflammation, intravascular blood coagulation, and emphysema. This discovery led to the conclusion that gut flora-derived extracellular vesicles play an important role in causing the onset of vascular diseases characterized by intravascular blood coagulation-induced thrombus, such as acute coronary syndrome and stroke, as well as sepsis, and pulmonary diseases such as emphysema, acute respiratory distress syndrome, etc. Thus, the present inventors developed an animal model for systemic diseases by the systemic injection of the gut flora-derived extracellular vesicles.

It is well known that bacterial intestinal infection is followed by arthritis. Recently, increasing attention has been drawn to the correlation between metabolic diseases, such as obesity, diabetes, etc., and gut flora. It was first found by the present inventors that when gut flora-derived extracellular vesicles had been systemically administered at a low dose for a long period of time, such diseases as hypertension and osteoporosis were generated. That is, gut flora-derived extracellular vesicles act as a causative factor of such chronic diseases which have remained unclear about etiology. Thus, models for the chronic diseases can be established with gut flora-derived extracellular vesicles.

It is very important to clarify the exact causative factors of a disease to develop drugs for the prevention or treatment thereof. For example, candidate drugs can be screened for pharmaceutical efficacy either in the course of the ex vivo treatment of cells with the causative factor or when administered to the animal model. In the present invention, a method for screening candidate drugs was established with gut flora-derived extracellular vesicles, and using the method, drugs useful for preventing or treating gut flora-derived extracellular vesicle-caused diseases were developed. For instance, of 80 different kinase inhibitors, 11 candidate drugs capable of suppressing the secretion of inflammatory mediators were screened by the method. Also, one of 30 different phosphatase inhibitors and 14 of 100 different prodrugs were selected as candidate drugs that could be evaluated for pharmaceutical efficacy in vivo by injection into the established disease animal model. That is, the screening method of the present invention can be effectively used to excavate drugs preventive or therapeutic of the diseases caused by gut flora-derived extracellular vesicles.

Understanding of an exact factor causative of a disease is essential for the development of a vaccine against the disease. In the case of viral infections, pathogenic agents in attenuated forms, when administered in vivo, induces immune responses to the viruses and thus can be used as a vaccine. In practice, vaccines are used to prevent many viral infections. It is also revealed by the present inventors that injection with gut flora-derived extracellular vesicles provokes immune responses to the vesicles and thus can prevent the onset of gut flora-derived extracellular vesicles-induced diseases. This indicates that gut flora-derived extracellular vesicles in their intact form or in a modified form for enhancing pharmaceutical efficacy or reducing side effects can be used, optionally in combination with an effective drug, as a vaccine against systemic diseases such as sepsis, arteriosclerosis, acute coronary syndrome, stroke, emphysema, acute respiratory distress syndrome, osteoporosis, hypertension, obesity, diabetes, arthritis, and cerebral disease and localized diseases such as mouth ulcer, oral cancer, esophagitis, esophageal cancer, gastritis, duodenal ulcer, stomach cancer, inflammatory bowel disease, irritable bowel syndrome, colorectal cancer, cholangitis, cholecystitis, pancreatitis, cholangiocarcinoma, and pancreatic cancer, in which gut flora-derived extracellular vesicles act as a pathogenic agent.

For several decades, vaccines based on bacterial exotoxin proteins have been developed against diseases caused by the bacterial exotoxins. However, effective vaccines against bacteria themselves are not yet developed. Vaccines against Gram-positive bacteria themselves were developed taking advantage of capsular polysaccharides, but are functionally low because the antibodies evoked by the vaccines are formed independently of T-cells and work against only a specific sub-type of bacteria. In order to develop the production of T-cell-dependent antibodies, protein-conjugated vaccines were developed. However, these vaccines are expensive and still cannot overcome the problem of targeting only specific sub-types of bacteria. In contrast, bacterial vesicles can be used for constructing a vaccine that overcomes the narrow spectrum of the antibacterial activity of conventional bacteria vaccines because the vesicles retain many kinds of bacterial proteins. In addition to the production of antibodies against bacteria, bacterial vesicles, if used as a vaccine, enjoy the advantage of effectively inducing immune responses because of their immunopotentiators provoking T cell responses. In the present invention, it was found that gut flora-derived extracellular vesicles, when administered, effectively induce Th1 and Th17 immune responses, T cell responses important for defense against bacteria, as well as the production of antibodies against bacterial proteins, thereby preventing gut flora infection. This indicates that gut flora-derived extracellular vesicles can be applied to the prevention or treatment of gut flora-caused diseases. In this context, gut flora-derived extracellular vesicles can be used themselves as a vaccine against peritonitis, sepsis, pneumonia, urinary tract infection, bone infection and central nervous system infection. In order to augment their pharmaceutical effects or reduce side effects, gut flora-derived extracellular vesicles may be modified or used in combination with a drug.

The fact that gut flora-derived extracellular vesicles are a pathogenic agent of systemic diseases including sepsis, arteriosclerosis, acute coronary syndrome, stroke, emphysema, acute respiratory distress syndrome, osteoporosis, hypertension, obesity, diabetes, arthritis, and cerebral diseases and localized diseases including gastritis, duodenal ulcer, stomach cancer, inflammatory bowel disease, and irritable bowel syndrome, colorectal cancer is very important for exactly diagnosing the diseases the cause of which has remained elusive. In the present invention, genetic agents of gut flora-derived extracellular vesicles were base sequenced and the corresponding proteins were identified. In addition, the production of specific antibodies against gut flora-derived extracellular vesicles was induced. With these data, the present inventors succeeded in the development of a method for exactly diagnosing a pathogenic factor of the diseases.

In the present invention, extracellular vesicles isolated from mouse feces were subjected to proteomic assay to identify a total of 295 proteins. Of them, 77 were from Gram-negative bacteria, 145 from Gram-positive bacteria and the remaining 73 from mouse host cells. The proteomic assay also allowed the identification of the bacteria from which the extracellular vesicles were secreted. Representative among the Gram-negative bacteria are *Bacteroides thetaiotaomicron, Escherichia coli*, and *Klebsiella pneumoniae*. The Gram-positive bacteria detected included *Bifidobacterium longum, Clostridium perfringens, Enterococcus faeacalis, Eubacterim rectale, Lactobacillus reuteri, Propiobacterium acnes*, and *Streptococcus agalactiae*.

Inflammatory bowel disease is a group of inflammation conditions of the large intestine and keen attention has recently been paid to Th17-mediated inflammatory responses with regard to inflammatory bowel disease. Particularly, while patients of inflammatory bowel disease do have an increased risk of colorectal cancer, animal tests showed that Th17 immune responses accounted for the onset of colorectal cancer. The oral administration of dextran sodium sulfate (DSS) is typically known as a method of establishing inflammatory bowel disease animal models. In the present invention, the oral administration of 1% DDS was done for six days. On day seven, extracellular vesicles were separated from the small intestinal fluid of the animal models thus established. In an ex vivo test, mouse macrophages (RAW 264.7) were not induced to secrete interleukin-6 (IL-6) by the extracellular vesicles from the small intestinal fluid of normal mice. In contrast, the extracellular vesicles from the small intestinal of diseased mice were found to induce the secretion of IL-6 from the mouse macrophages. Considering the fact that IL-6 plays an important role in inducing Th17 immune responses, the extracellular vesicles from the small intestinal fluid of diseased animals are thought to induce Th17 immune responses. Further, when the extracellular vesicles from the small intestinal fluid of diseased animals were administered together with polymyxin B, an inhibitor of LPD, a component of the outer membrane of Gram-negative bacteria, IL-6 was not released, which implies that the extracellular vesicles derived from the Gram-negative bacteria of gut flora play a critical role in inflammatory bowel disease.

Cecal ligation and puncture (CLP) is a widely used experimental model of sepsis. In this invention, after CLP, gut flora associated with sepsis was separated by the irrigation of abdominal cavity. Base sequence analysis of 16S rRNA identified the separate bacteria as *E. coli*, and spherical extracellular vesicles with a size of from 20-40 nm were found bud off from the bacteria as observed by electron microscopy.

In the present invention, extracellular vesicles which were physiologically secreted from gut flora in the absence of separate physicochemical stimuli were also separated. For example, after *E. coli* is cultured in broth for a predetermined period of time, a supernatant is obtained and filtered through a filter which allows the passage of extracellular vesicles, but does not for cells. The filtrate is then ultra-centrifuged to separate extracellular vesicles. The *E. coli*-derived extracellular vesicles contain LPS and outer membrane proteins, both inducing inflammatory responses. The extracellular vesicles spontaneously secreted to media of *E. coli* contained inner and outer membrane proteins and LPS in an amount of 75% based on the total weight thereof.

In addition to spontaneously secreted extracellular vesicles, gut flora-derived extracellular vesicles can be formed using various mechanical, electrical and chemical methods. For example, extracellular vesicles may be formed and separated by osmotic cell lysis, electroporation, sonication, homogenization, detergent treatment, freeze-thaw, extrusion, and/or mechanical degradation. Unless otherwise stated, the extracellular vesicles of the present invention refer to those secreted spontaneously from a culture of bacteria.

To examine whether the *E. coli-extracellular* vesicles induce the secretion of inflammatory mediators, mouse macrophages (RAW 264.7) were treated with extracellular vesicles. As a result, the macrophages were observed to secrete inflammatory mediators such as TNF-α and IL-6 in a dose-dependent manner.

Because innumerable bacteria live in the gut, germ-free mice are employed to evaluate the etiology of a specific microorganism. The airways are an optimal environment in which the etiology of a specific bacterium can be investigated because they are free of germs compared to the gastrointestinal tracts. In the present invention, *E. coli*-derived extracellular vesicles were locally administered into the airways to evaluate if they induced mucosal inflammation. The count of inflammatory cells in bronchoalveolar lavage (BAL) fluid was observed to increase in proportion to the concentration of the extracellular vesicles. Further, as for IL, which is associated with Th17 immune responses and oncogenesis, its secretion was increased with an increase in the dose of the vesicles. These results indicate that extracellular vesicles derived from the Gram-negative bacteria of gut flora act locally on mucous membranes to induce Th17-mediated inflammation.

To examine whether *E. coli-extracellular* vesicles induce systemic inflammatory responses when they are systemically introduced, extracellular vesicles were intraperitoneally administered. As a result, the mortality of the mice increased with increasing of the dose of the extracellular vesicles.

Together with local bacterial infection, sepsis is characterized by systemic inflammatory response syndrome (SIRS). Criteria for SIRS include high respiratory rate, elevated or lowered body temperature, elevated heart rate, and abnormal white blood cell count. Sepsis can be diagnosed when two or more of the criteria are present. In the present invention, when *E. coli-extracellular* vesicles were intraperitoneally injected at a sub-lethal dose, the levels of the inflammatory cytokines, TNF-α, IL-6, IL-12, and IL-17, in blood were increased with the concomitant induction of high respiratory rate, lowered body temperature, and reduced leukocyte count, demonstrating that *E. coli*-derived extracellular vesicles are absorbed into blood vessels to induce the secretion of inflammatory cytokines and to cause sepsis.

Sepsis is clinically important for its high mortality. When developed into severe sepsis, the patient is at high risk of death. In the present invention, the intraperitoneal injection of extracellular vesicles induced hypotension, an indicator of severe sepsis. This indicates that bacterial extracellular vesicles play an important role in the development of sepsis to severe sepsis.

Blood coagulation within vessels blocks the vessels, evoking sudden death. Particularly, when brain blood vessels and coronary artery are blocked due to the thrombosis formed by blood coagulation, stroke and acute coronary syndrome are respectively induced, which frequently lead to death.

To examine whether gut flora-derived extracellular vesicles, when introduced into blood vessels, induce blood coagulation, *E. coli*-derived extracellular vesicles were intraperitoneally injected. As a result, a reduced level of platelets and an increased level of D-dimer, which are both diagnostic criteria for disseminated intravascular coagulation (DIC), were detected in the group administered with extracellular vesicles. This observation implies that when introduced into blood vessels, gut flora-derived extracellular vesicles induce intravascular coagulation and may be a risk factor of stroke and acute coronary syndrome if they act in brain blood vessels and the coronary artery, respectively.

An examination was made to see whether gut flora-derived extracellular vesicles act on and activate vascular endothelial cells to cause blood coagulation. For this, HUVEC cells were treated with gut flora-derived extracellular vesicles. An elevated level of ICAM-1 was measured as in various disease states including inflammatory responses and coronary artery diseases, indicating that gut flora-derived extracellular vesicles activate vascular endothelial cells and cause blood coagulation to generate thromobosis or embolism, which leads to ischemic vascular diseases.

Another problem generated upon the introduction of gut flora-derived extracellular vesicles into blood vessels is the assignment of the vesicles to various organs. In fact, the intraperitoneal injection of *E. coli*-derived extracellular vesicles resulted in the distribution thereof over the whole body, and particularly in the infiltration thereof into pulmonary tissues. An examination was made to see whether the extracellular vesicles infiltrated into pulmonary tissues induce pneumonia. The wet-dry ratio, an index for pneumonia, was significantly increased after the administration of extracellular vesicles. The count of inflammatory cells in BAL fluid was also detected at an elevated value. Further, tissue injury by inflammation was evaluated. In the group administered with extracellular vesicles, emphysema, characterized by the destruction of alveoli, took place. Based on this observation, it can be inferred that when introduced into blood vessels, gut flora-derived extracellular vesicles may be distributed over various organs including the brain, the bone joint, the kidney, etc. and induce inflammation and tissue injury on the organs, causing various diseases.

Gut flora continuously secretes extracellular vesicles which are in turn introduced into blood vessels to cause various problems. In the present invention, *E. coli*-derived extracellular vesicles were administered at a low dose for a long period of time while a change in the body, if occurred, was monitored. As a result, hypertension and osteoporosis were generated after the administration of extracellular vesicles. This suggests that gut flora-derived extracellular vesicles may act as an important factor responsible for the onset of chronic inflammatory diseases whose causes have remained elusive thus far.

IL-6 is involved in inflammation and oncogenesis through various processes. With regard to oncogenesis, IL-6 is known to induce the expression of genes associated with cell proliferation, angiogenesis, invasion and immune evasion through SAT3-mediated signal transduction. Also, IL-6 is induces Th17-mediated neutrophilic inflammation, which may be responsible for the onset of cancer. Further, blood IL-6 levels are closely correlated with the prognosis of arteriosclerosis and chronic obstructive pulmonary disease including emphysema with regard to the death of the patients. Particularly, IL-6 secreted from inflammatory cells in blood is involved in blood coagulation as it acts on vascular endothelial cells to increase the expression of coagulation-related factors. The etiological role of IL-6 was examined in the sepsis animal models established with *E. coli*-derived extracellular vesicles. In this regard, *E. coli*-derived extracellular vesicles were intraperitoneally injected into wild-type and IL-6-knockout mice. Over 80% of the wild-type mice were dead due to the *E. coli-extracellular* vesicles whereas all of the IL-6-knockout mice survived the vesicle administration. Also, the intraperitoneal injection of E. coli-derived extracellular vesicles evoked the onset of emphysema in the wild-type mice, but not in the IL-6-knockout mice. This data shows that IL-6 the secretion of which is induced by gut flora-derived extracellular vesicles is an important biomarker of the etiology of the diseases caused by extracellular vesicles.

Based on the research results obtained above, the present inventors developed a method for screening candidate drugs preventive or therapeutic of diseases caused by gut flora-derived extracellular vesicles. To this end, *E. coli*-derived extracellular vesicles were used as a pathogenic agent while the secretion of IL-6 from mouse macrophages (RAW 264.7) was evaluated as an index for pharmaceutical efficacy. The macrophages were treated, in the presence of extracellular vesicles, with 80 different kinase inhibitors (kinase inhibitor library, BIOMOL No. 2832: PD-98059, U-0126, SB-203580, H-7, H-9, AG-494, AG-825, Lavendustin A, RG-14620, Tytphostin 23, Tytphostin 25, Tytphostin46, Tytphostin47, Tytphostin 51, Tytphostin 1, Tytphostin 9, Tytphostin AG 1288, Tytphostin AG 1478, Tytphostin AG 1295, HNMPA, Damnacanthal, Piceatannol, AG-490, AG-126, AG-370, AG-879, LY 294002, Wortmannin, GF 109203×, Hypericin, Sphingosine, H-89, H-8, HA-1004, HA-1077, HDBA, KN-62, KN-93, ML-7, ML-9,2-Aminopurine, N9-Isopropyl-olomoucine, Olomoucine, iso-olomoucine, Roscovitine, LFM-A13, SB-202190, ZM 336372, SU 4312, AG-1296, Rottlerin, Genistein, Daiazein, Erbstatin analog, Quercetin dehydrate, SU 1498, ZM 449829, DRB (5,6-Dichloro-1-b-D-ribofuranosylbenzimidazole), HBDDE (2,2',3,3',4,4'-Hexahydroxy-1,1'-biphenyl-6,6'-dimethanol dimethyl ether), Indirubin, Indirubin-3'-monoxime, Y-27632, Kenpaullone, Terreic acid, BML-257, BML-259, Apigenin, BML-265 (Erlotinib analog), Rapamycin), 30 different phosphatase inhibitors (phosphatase inhibitor library, BIOMOL No. 2834: Cantharidic acid, Cantharidin. Endothall, Benzylphosphonic acid, L-p-Bromotetramisole oxalate, RK-682, RWJ-60475, RWJ-60475 (AM)3, Levamisole HCl, Tetramisole HCl, Cypermethrin, Deltamethrin, Fenvalerate, Tyrphostin 8, CinnGEL, CinnGEL 2 Me, BN-82002, Shikonin, NSC-663284, Cyclosporin A, Pentamidine, BVT-948, B4-Rhodanine, BML-268, Dioxophenanthrene, BML-260, PD-144795, BML-267, BML-267 Ester, OBA, OBA Ester, Gossypol, Alendronate), and 100 different prodrugs (acetaminophen, acetylcysteine, allopurinol, alprenolol HCl, amitriptyline HCl, atropine, bretylium tosylate, bromopheniramine, budesonide, buspirone HCl, cefuroxime, chloral hydrate, chlorpromazine HCl, cimetidine, clomipramine HCl, clotrimazole, cyclobenzaprine, desipramine HCl, diclofenac, diflunisal, diltiazem, diphenhydramine HCl, disopyramine, disulfuram, D-mannitol, doxepin, doxycycline hydrate, doxylamine succinate, edrophonium chloride, enalapril maleate, famotidine, fenbufen, fenofibrate, fenoprofen calcium salt hydrate, flunarizine dihydrochloride, fluphenazine dichloride, flurbiprofen, furosemide, gemfibrozil, gliclazide, glipizide, haloperidol, hydrochlorothiazide, hydroflumethiazide, hydroxyzine HCl, ibuprofen, imipramine HCl, indapamide, indole-2-carboxylic acid, indomethacin, ipratropium, ketoprofen, ketorolac tris salt, maprotiline HCl, meclofenamic acid, melatonin, metformin, methapyrilene HCl, methimazole, methocarbamol, metoclopramide HCl, metronidazole, nabumetone, naproxen, neostigmine Br, niacin, nicardipine HCl, nifedipine, nitrofurantoin, nizatidine, norethindrone, nortriptyline, orphenadrine HCl, oxybutynin, phenformin HCl, phenylbutazone, phenyloin, piroxicam, prednisone, probenecid, propranolol HCl, pyridostigmine Br, ranitidine HCl, spironolactone, sulfameth, sulpiride, tenoxicam, terfenadine, theophylline, ticlopidine HCl, tolazamide, tolazoline, tolbutamide, tolfenamic acid, tramadol HCl, tranylcypromine, trazodone HCl, triamterene, trichlormethiazide, tripelennamine HCl, verapamil, warfarin). The extracellular vesicle-induced IL-6 secretion was inhibited by 11 of the kinase inhibitors, one of the phosphatase inhibitors and 14 out of the prodrugs.

The pharmaceutical efficacy of the candidate drugs were evaluated in terms of inhibitory activity against IL-6 secretion in vivo. When intraperitoneally injected with the candidate drugs, model mice in which a systemic inflammatory response was induced by the intraperitoneal injection of 5 μg of *E. coli*-derived extracellular vesicles showed a reduction in blood IL-6 level which was increased by the extracellular vesicles. Hence, the method of the present invention is useful for screening candidate drugs therapeutic of inflammatory diseases.

Among the defense factors against bacterial infection are T cells involved in cell-mediated immune response and B cells involved in antibody production. Antibodies which are produced in response to bacterial infections may be largely divided into those to non-protein antigens such as LPS and those specific for protein antigens. T cells have no influence on the production of the former while the production of the latter is affected by T cells. T cell immune responses may be classified according to cytokine secretion: Th1 type response to secrete IFN-γ; Th17 type response to secrete IL-17; and Th2 type response to secrete IL-4/IL-5/IL-13. Of them, Th1 and Th2 are responsible for defense against bacteria. Extracellular vesicles derived from bacteria may be useful as vaccines because they retain various bacterial proteins as well as immunopotentiators which augment immune responses. In the present invention, an examination was made of the use of gut flora-derived extracellular vesicles as a vaccine to induce immune responses to bacteria. In this regard, extracellular vesicles derived from *Escherichia coli* (EC) and *Klebsiella pneumonia* (KP) were intraperitoneally injected once at regular interval of one week for three weeks while the immune responses were evaluated. As a result, levels of antibodies to bacteria-specific proteins were increased with the number of administration. The secretion of IFN-γ and IL-17 by T cells were significantly increased by the respective antigenic proteins present in the bacteria. This indicates that the administration of gut flora-derived extracellular vesicles induces not only the production of antibodies to the proteins of vesicle-secreting bacteria, but also protein-specific Th1 and Th17 immune responses, thereby effectively preventing or treating bacterial infections and extracellular vesicles-caused diseases.

An examination was made to see whether the vesicle vaccine induced immune responses which would prevent bacterial infections and extracellular vesicle-caused diseases. To this end, animal models were established by the intraperitoneal injection of *Escherichia coli* and *Klebsiella pneumonia*, both derived from gut flora. To test groups, *Escherichia coli*- and *Klebsiella pneumonia*-derived extracellular vesicles were respectively injected to induce immune responses in advance of the injection of the bacteria. The efficacy of the vesicle vaccines was evaluated as the mortality of the sepsis generated by the intraperitoneal injection of *Escherichia coli* and *Klebsiella pneumonia*. The *Escherichia coli*- and *Klebsiella pneumonia*-derived extracellular vesicle vaccines effectively reduced the mortality of sepsis caused by *Escherichia coli* and *Klebsiella pneumonia* infections. In addition, the injection of the *Escherichia coli*-derived vesicle vaccine significantly reduced the blood IL-6 level, which is increased when *E. coli*-derived extracellular vesicles are introduced into blood. These results demonstrate that the immune responses induced by the use of gut flora-derived extracellular vesicles as a vaccine is useful in the prevention of gut flora infections as well as diseases caused by bacterial extracellular vesicles.

As described above, a variety of diseases may be generated by gut flora-derived extracellular vesicles, indicating that gut flora-derived extracellular vesicles serve as an important pathogenic agent for the diseases which have remained unclear about their causes. To provide a method for the diagnosis of a pathogenic agent, gut flora-derived extracellular vesicles were examined to see whether they contain a genetic material. As a result, 16S rRNA was detected. In the case of extracellular vesicles separated from mouse feces, they contain the genetic materials of *Escherichia coli* and *Klebsiella pneumonia* out of 10 representative bacteria that live in the large intestine. In addition, after the intraperitoneal injection of gut flora-derived extracellular vesicles into mice, extracellular vesicle proteins were detected at various organs, urine and blood of the mice. Based on this observation, the examination of genetic materials and extracellular vesicle proteins in a sample such as urine, feces and blood, which can be easily taken, allows the pathogenic agent of a disease to be readily identified, thus enabling the disease to be diagnosed.

A better understanding of the present invention may be obtained through the following examples which are set forth to illustrate, but are not to be construed as limiting the present invention.

EXAMPLES

Example 1

Proteomic Assay of Extracellular Vesicles Separated from Normal Mice

Extracellular vesicles were separated from mouse feces. In this regard, first, 25 g of feces excreted from 5-week-old, male C57BL/6 mice was resuspended in 2 L of PBS (phosphate buffered saline) at 4° C. for 16 hours. After the centrifugation of the suspension at 4° C. and 10,000×g for 20 min, the supernatant was passed through a filter with a pore size of 0.45 nm. The filtrate thus free of bacteria was about 30-fold concentrated to 70 mL using QuixStand Benchtop System equipped with a membrane with 100 kDa cutoff. The concentrate was again centrifuged at 4° C. and 10,000×g for 20 min. This supernatant was added to 0.5 ml of 2.5 M sucrose solution (2.5 M sucrose/20 mM HEPES/150 mM NaCl, pH7.4) and 1 ml of 0.8 M sucrose solution (0.8 M sucrose/20 mM HEPES/150 mM NaCl, pH7.4) in an ultracentrifuge tube, followed by ultracentrifugation at 4° C. and 100,000×g for 4 hours. The layer containing extracellular vesicles between 2.5 M and 0.8 M sucrose solutions were taken. The layer was 10-fold diluted in PBS and added to 0.15 ml of 2.5 M sucrose solution and 0.35 ml of 0.8 M sucrose solution in an ultracentrifuge tube before ultracentrifugation at 4° C. and 200,000×g for 2 hours. The extracellular vesicle-containing layer between 2.5 M and 0.8 M sucrose solutions was 10-fold diluted in PBS and then centrifuged at 4° C. and 150,000×g for 3 hours to form a precipitate. This precipitate was suspended in 2.2 mL of 50% Optiprep solution. The suspension was placed in an ultracentrifuge tube, followed by the addition of 2 mL of a 40% Optiprep solution and 0.8 mL of a 10% Optiprep solution to the suspension in that order. Ultracentrifugation at 4° C. and 200,000×g for 2 hours formed a layer of extracellular vesicles between the 40% Optiprep solution and the 10% Optiprep solution.

For the proteome analysis of extracellular vesicles separated from mouse feces, in-solution tryptic digestion was utilized. In a solution (7 M urea, 2 M Thiourea, 100 mM $NH_4HCO_3$), 50 mg of the extracellular vesicles was dissolved, followed by reduction by 10 mM DTT at 60° C. for 45 min. Then, the sample was cooled to room temperature and incubated with 55 mM iodoacetamide at room temperature for 30 min in a dark condition to alkylate proteins. Ten μg of trypsin was added and activated by sonication before incubation at 37° C. for 12 hours. The peptides thus degraded were separated using the OFFGEL fractionators system (Agilent). To begin with, a 24 cm-long IPG strip (pH 3-10) was hydrated with IPG-rehydration. The degraded peptides were dissolved in 2.8 ml of off-gel buffer, and the solution was loaded in an amount of 150 p. 2 per lane. Electrophoresis at 50 mA, 8000 V for 40 hours separated the peptides according to isoelectric point (pI). The samples were desalted using a PepClean C18 spin column.

Mass analysis was done using Nano-LC-ESI-MS/MS. The degraded peptides of extracellular vesicles from mouse feces, prepared by the in-solution digestion, were loaded to a column (75 mm×12 cm) filled with 5 mm-sized C18 resins, and then separated as follows: 3-40% buffer B 70 min; flow rate 0.3 ml/min (buffer A composition: 0.1% formic acid in $H_2O$, buffer B composition: 0.1% formic acid in acetonitrile). The eluting peptides were introduced into LTQ-ion-trap mass spectrometer (Thermo Finnigan) with a 1.9 kV electrospray voltage under a normalized collision energy set to 35% for MS/MS.

All MS/MS spectra were acquired by data-dependent scans in which the five most abundant spectra from the full MS scan were selected for fragmentation. The repeat count for dynamic exclusion was set to 1, the repeat duration to 30 sec, and the dynamic exclusion duration to 180 sec, exclusion mass width to 1.5 Da, and the list size of dynamic exclusion to 50.

To analyze the proteins present in extracellular vesicles derived from intestinal cells of mice, the data base (Uniprot) in which murine amino acid sequences had been pooled were utilized. As for the proteins of the extracellular vesicles derived from intestinal bacteria, their analyses were also conducted with reference to the database (Uniprot) for 10 different bacterial species representative of the most abundant genus in the intestine. Data analyses were performed 11 times in total using each database. The MASCOT search engine version 2.2 was used to analyze all the spectra from the mass spectrometry (MS spectrum and MS/MS spectrum). The search results were validated by peptide prophet/protein prophet to select proteins with above 95%/99% confidence. As for the proteins for each of which only one peptide spectrum was obtained, their amino acid sequences were manually validated for spectral quality.

FIG. 1 summarizes results from the proteomic assay of extracellular vesicles separated from mouse feces, showing the identification of a total of 295 proteins 222 of which are counted for by bacterial proteins with 77 of Gram-negative bacterial proteins and 145 of Gram-positive bacterial proteins. Predominant in the Gram-negative bacterial proteins are those from *Bacteroides thetaiotaomicron*, *Escherichia coli* K-12, and *Klebsiella pneumonia*, while *Clostridium perfringens* and *Lactibacillus reuteri* dominate over other Gram-positive bacteria.

Example 2

Secretion of Inflammatory Mediators by Extracellular Vesicles Separated from Small Intestinal Fluid of Normal and Diseased Mice Extracellular vesicles were separated from small intestinal fluids of normal mice and DSS-induced mouse model of irritable bowel disease. To this end, mice were operated on to excise the small intestine. The peyer's patch and liquid were removed from the excised small intestine which was then cut at regular lengths of about 5 cm. The intestinal pieces were transversely cut and washed with physiological saline to remove impurities therefrom. They were again cut into pieces with dimensions of 1 cm×1 cm and vortexed five times for five sec per time in 30 mL of physiological saline. After the removal of intestinal tissues and impurities by centrifugation, the supernatant was ultra-centrifuged to separate extracellular vesicles.

FIG. 2 shows sizes and morphologies of the separated extracellular vesicles as observed by transmission electron microscopy (TEM). Spherical extracellular vesicles with a size of about 100 nm were detected.

Figure 3:
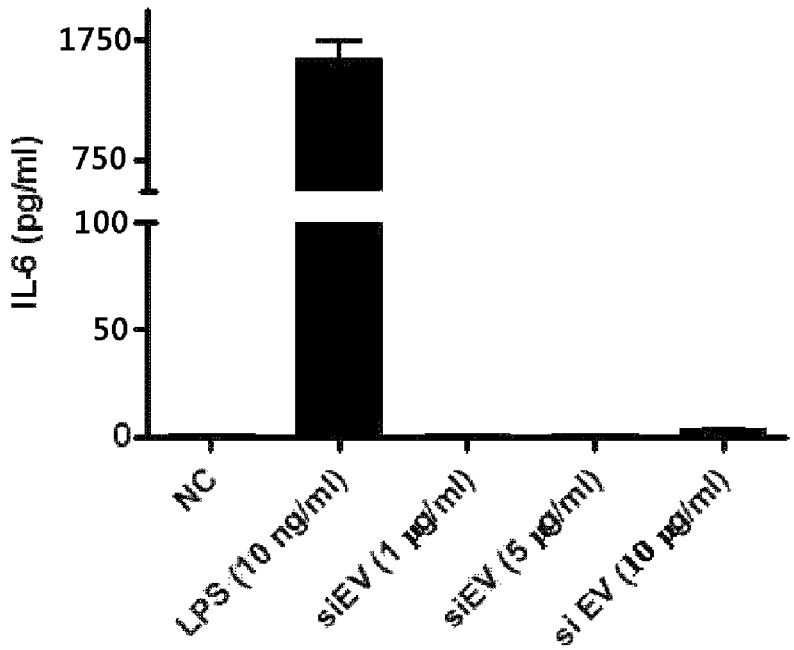
FIG. 3 is a graph showing the secretion of the inflammatory cytokine IL-6 in mouse macrophages (RAW 264.7) treated for 6 hours with various concentrations of the extracellular vesicles (siEV) separated from the small intestinal fluids of normal mice as measured by ELISA.
Figure 4:
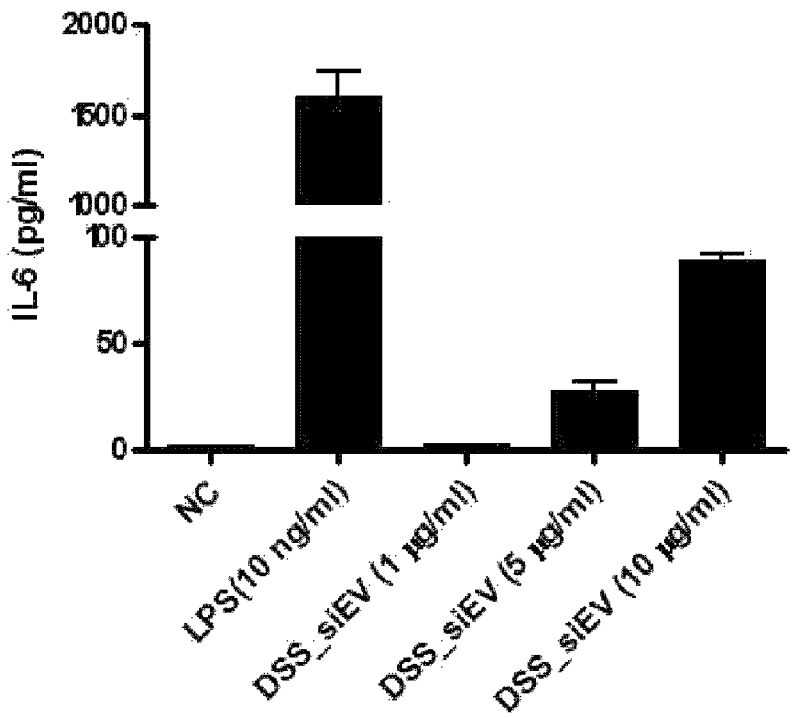
FIG. 4 is a graph showing the secretion of the inflammatory cytokine IL-6 in mouse macrophages (RAW 264.7) treated for 6 hours with various concentrations of the extracellular vesicles (DSS siEV) separated from the small intestinal fluids of DSS-induced mouse models of IBD, as measured by ELISA.

FIGS. 3 and 4 show the secretion of the inflammatory cytokine IL-6 in mouse macrophages (RAW 264.7) treated with various concentrations of the extracellular vesicles separated from the small intestinal fluids of normal mice and DSS-induced mouse models of IBD. As can be seen, the extracellular vesicles from normal extracellular vesicles did not induce the secretion of IL-6. In contrast, the extracellular vesicles from the DSS-induced mouse model of IBD were found to induce the expression of IL-6 in a dose dependent manner as measured by ELISA (enzyme linked immunosorbent assay).

Figures 5, 6:
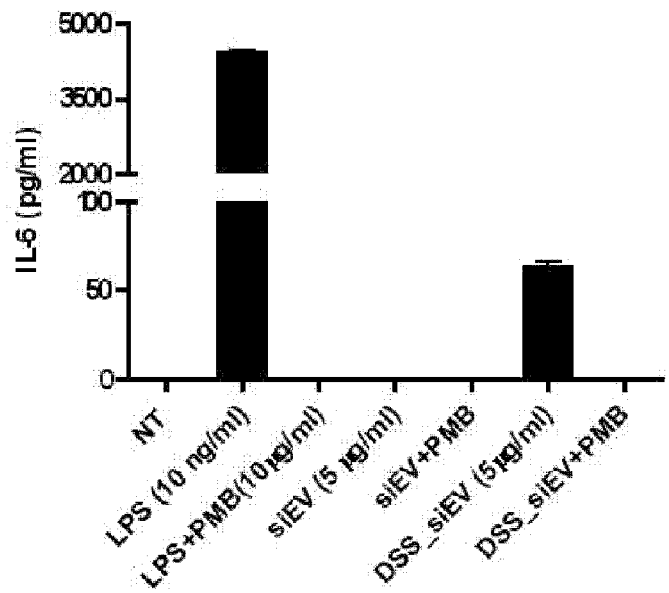
FIG. 5 is a graph showing the secretion of the inflammatory cytokine IL-6 in mouse macrophages (RAW 264.7) which were treated for 6 hours with the extracellular vesicles (siEV and DSS siEV) separated from the small intestinal fluids of normal mice and DSS-induced mouse models of IBD, in the presence of the LPS inhibitor polymyxin B (PMB), as measured by ELISA.
FIG. 6 is a base sequence of the 16s rRNA of $E.$ $coli$ separated from the mouse intestine SEQ ID NO. 1.

FIG. 5 provides the results after an experiment was done to see whether the extracellular vesicles from the DSS-induced mouse model of IBD contained those derived from Gram-negative bacteria. As can be seen in the graph, when mouse macrophages (RAW 264.7) were treated with the extracellular vesicles from the DSS-induced mouse model of IBD in combination with polymyxin B, which is an inhibitor of LPS, a component of the outer membrane of Gram-negative bacteria, the secretion of IL-6 was decreased in contrast to the observation that the secretion of IL-6 was induced when treated with the extracellular vesicles from the DSS-induced mouse model of IBD, alone.

Taken together, these results indicate that intestinal Gram-negative bacteria-derived extracellular vesicles play an important role in the onset of irritable bowel disease.

Example 3

Characterization of Extracellular Vesicles Isolated from *E. coli* of Gut Flora in Peritoneal Fluid of CLP-Induced Animal Model of Sepsis CLP (cecal ligation and puncture) was performed as previously reported. In brief, one C57BL/6 (male, 6 weeks old) mouse was anesthetized and a midline incision was made through the linea alba. The cecum was located, ligated with a sterile thread and perforated twice with 18-gauge needle. Forty hours later, 3 mL of PBS was intraperitoneally injected into the mouse using a 5 mL syringe and well-mixed therein, after which 1 mL of peritoneal fluid was recovered. A mixture of 10 µl of the recovered fluid and 90 µl of LB (Luria Bertani) was 10,000-fold diluted, spread over LB agar plates and incubated at 37° C. for 8 hours in an incubator. One of the colonies thus formed was inoculated into 5 mL LB in a test tube and incubated for 8 hours in a 37° C. incubator. A mixture of 10 µl of this culture and 90 µl of LB was 10,000-fold diluted, spread over LB agar plates, and incubated for 8 hours in a 37° C. incubator. The same colony picking procedure as above was repeated again to finally obtain one bacterial colony from which intestinal *E. coli* was isolated.

FIG. 6 provides a base sequence of 16S rRNA of the isolated intestinal *E. coli*, which is identified as *E. coli* C4, a bacterium species found in human feces.

Figure 7:
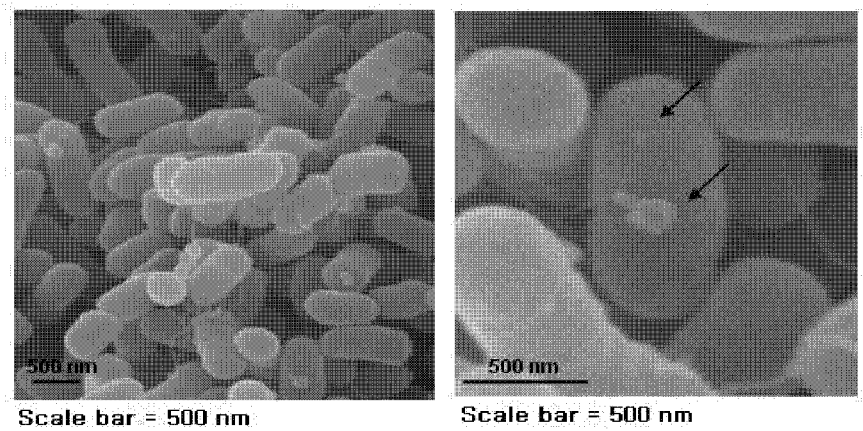
FIGS. 7 and 8 show murine intestinal bacteria as observed with SEM (scanning electron microscope, SEM) and TEM (transmission electron microscope), respectively.
Figure 8:
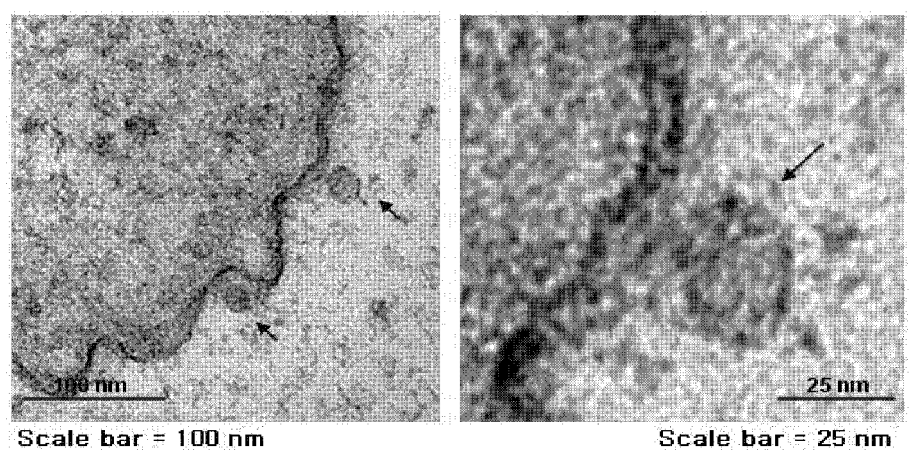

FIGS. 7 and 8 are respectively scanning electron microscope (SEM) and transmission electron microscope (TEM) photographs of the bacteria separated from the mouse intestine, showing extracellular vesicles with a size of 30 nm that are budding off from the bacteria.

The intestinal bacteria comprised seed cultured in 3 mL of LB at 37° C. for 4 hours and then scaled up in 8 2 L Erlenmeyer flasks each containing 500 mL of LB plus 10 µl of the seed culture by incubation at 37° C. for 4 hours. All the cultures were equally assigned to 12 350 mL-ultracentrifuge tubes and spun twice in succession at 4° C. and 5,000×g for 15 min per time. The supernatant, amounting to about 4 L, was allowed to pass once through a membrane filter with a pore size of 0.45 µm, and the filtrate was concentrated to a volume of 300 mL using the Quixstand system with 100 kDa cutoff. After one passage of the concentrate through a membrane filter with a pore size of 0.22 µm, the resulting filtrate was ultra-centrifuged at 4° C. and 150,000×g for 3 hours in 50 mL-ultracentrifuge tubes. The pellets thus formed were dissolved in PBS to separate extracellular vesicles derived from intestinal *E. coli*.

Figure 9:
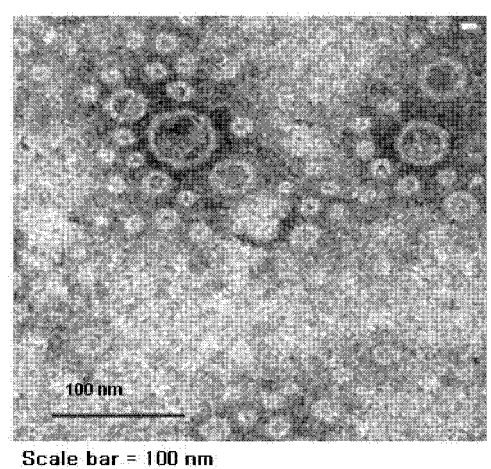
FIG. 9 is a TEM image showing the morphologies and sizes of the extracellular vesicles of intestinal $E.$ $coli$.

FIG. 9 shows the morphologies and sizes of the extracellular vesicles of intestinal *E. coli* as observed by a transmission electron microscope (TEM). As can be seen, the extracellular vesicles consist of a lipid bilayer and form spheres with a size ranging from 20 to 100 nm.

Figure 10:
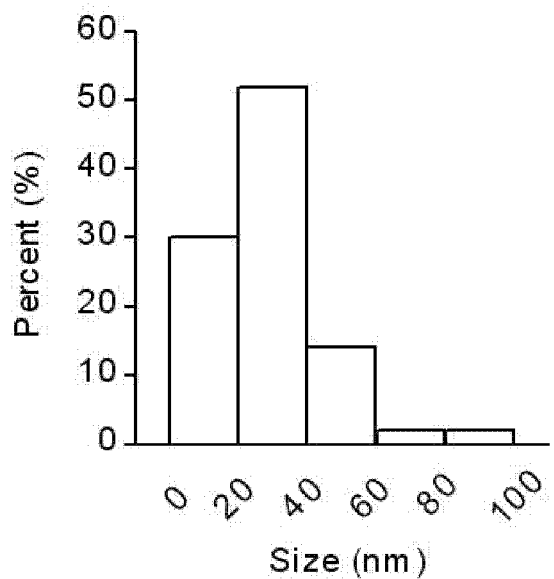
FIG. 10 is a graph showing a size distribution of the extracellular vesicles based on the data of 10 TEM photographs.

FIG. 10 shows a size distribution of the extracellular vesicles based on the data of 10 TEM photographs. The extracellular vesicles with a size of 20-40 nm constituted half of the total number.

Example 4

In vitro Secretion of Inflammatory Factor by *E. coli*-Derived Extracellular Vesicles Mouse macrophages (RAW 264.7) were seeded at a density of $1\times10^5$ cells/well into 24-well plates and cultured for 24 hours, after which the cells were incubated with extracellular vesicles (0.1, 1, 10, 100, 1000 ng/ml) or phenol-isolated bacterial LPS (100, 200, 500, 1000, 2000 ng/ml) in a 37° C. incubator for 15 hours. The medium was collected and centrifuged at 4° C., 500×g for 10 min and then at 4° C., 3000×g for 20 min. The cytokines of the supernatant were quantitatively analyzed using ELISA.

Figure 11:
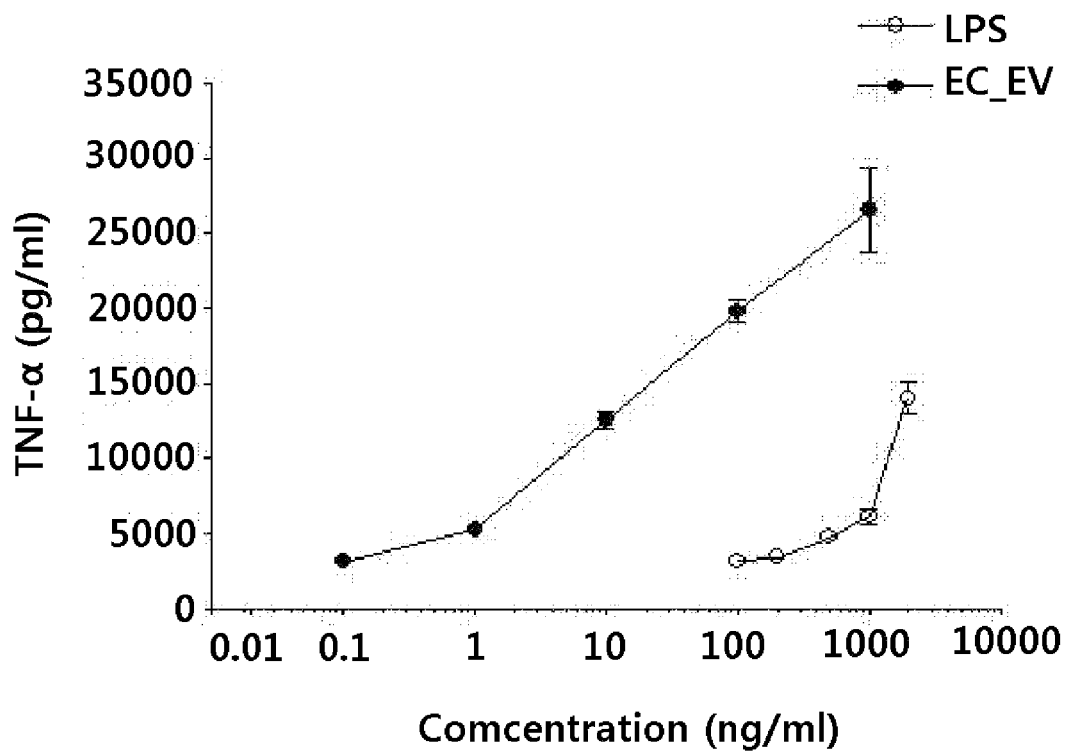
FIGS. 11 and 12 are graphs showing the levels of cytokines (TNF-$\alpha$ and IL-6) secreted from RAW 264.7 macrophages treated with various concentrations of $E.$ $coli$-derived extracellular vesicles (EC_EV) and bacterial LPS, as measured by ELISA.
Figure 12:
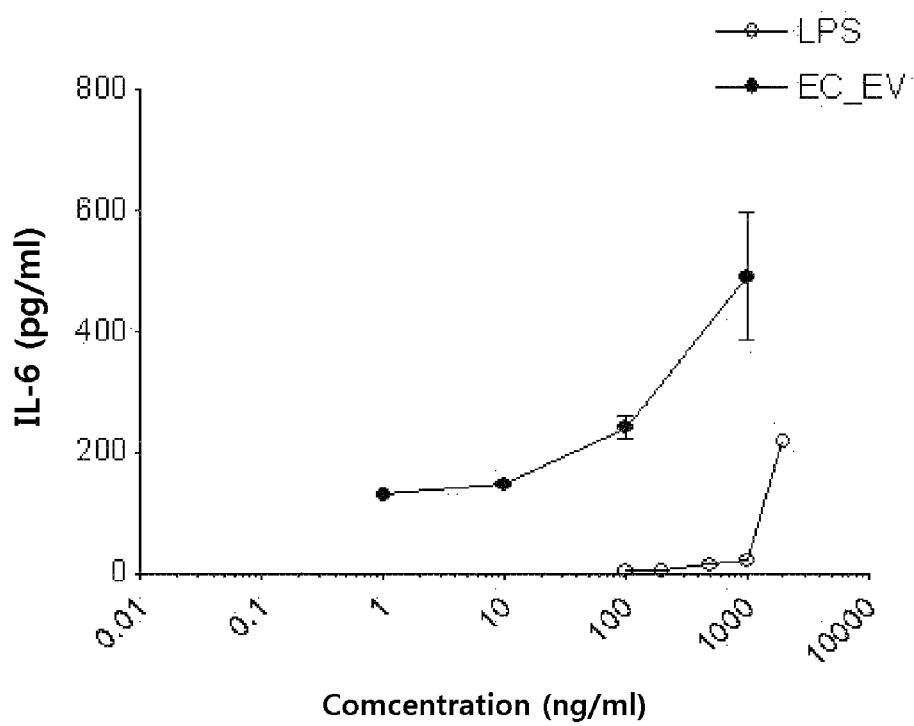

FIGS. 11 and 12 show cytokine levels as measured by ELISA. As can be seen, the secretion of the inflammatory cytokines INF-α (FIG. 11) and IL-6 (FIG. 12) were increased with an increase in the amount of the extracellular vesicles. The secretion of the inflammatory cytokines was triggered at a much lower dose of the extracellular vesicles, compared to LPS, alone. That is, gut flora-derived extracellular vesicles, even if at a very low concentration, act on inflammatory cells to induce the secretion of inflammatory cytokines.

Example 5

Mucosal Inflammation and IL-6 Secretion Induced by Local Administration of *E. coli*-Derived Extracellular Vesicles C57BL/6 mice (female, 6 weeks old) were divided into groups of five. The mice of a test group were intranasally administered with 1, 10, and 100 ng of extracellular vesicles.

Six and 24 hours after the intranasal administration, inflammation on the airway mucosa was examined. The mice were anesthetized by the intraperitoneal injection of a mixture of ketamine and xylazine. A vertical midline incision was made through which the trachea was opened so that a catheter was inserted into the airway, followed by ligation. The airway was washed twice with 1 mL of PBS. The bronchoalveolar lavage, (BAL) fluid thus obtained was centrifuged at 4° C. and 3,000 rpm for 10 min and the cell pellet was suspended in PBS. The cells were counted under an optical microscope. Further, IL-6, which is an inflammatory cytokine inducing a Th17 immune response, was quantitatively analyzed in the BAL fluid by ELISA.

Figure 13:
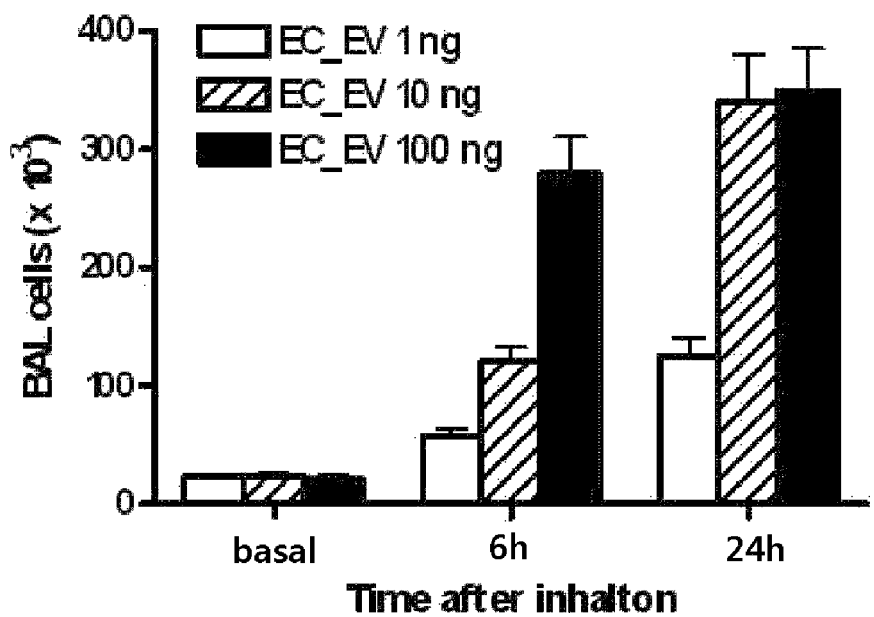
FIGS. 13 and 14 are graphs showing inflammatory cell counts and IL-6 levels in BAL fluid after the intranasal administration of $E.$ $coli$-derived extracellular vesicles at a dose of 1, 10 and 100 ng

FIG. 13 is a graph showing airway mucosal inflammation 6 and 24 hours after the intranasal administration of $E.$ $coli$-derived extracellular vesicles in terms of the counts of inflammatory cells in BAL fluid. The count of inflammatory cells in BAL fluid was significantly increased 6 and 24 hours after the administration of $E.$ $coli$-derived extracellular vesicles, compared to the count before the administration. The increase was at least in part dependent on the dose of the extracellular vesicles.

Figure 14:
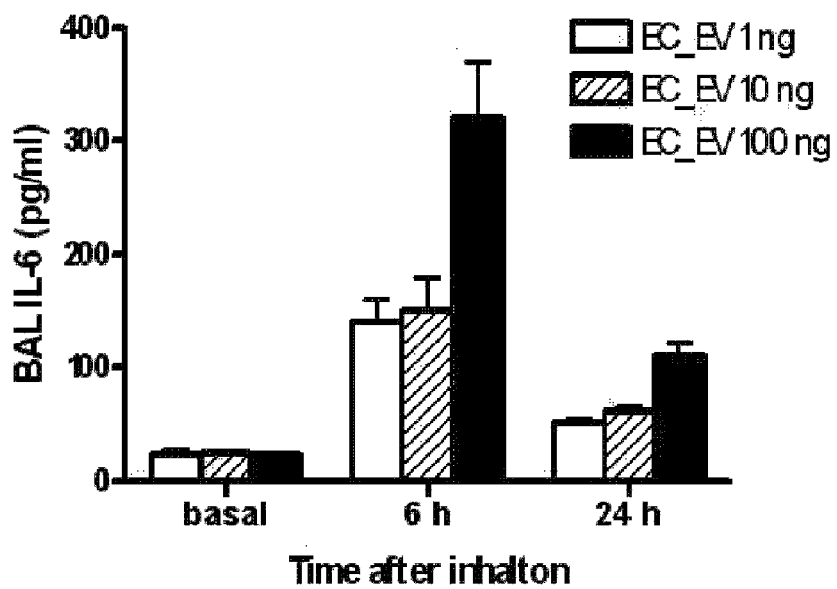

FIG. 14 is a graph showing the IL-6 levels of BAL fluid as measured by ELISA. The IL-6 level was remarkably increased in BAL fluid obtained 6 hours after the administration of $E.$ $coli$-derived extracellular vesicles, compared to that before the administration, and the increase was dose-dependent.

From the data, it can be inferred that gut flora-derived extracellular vesicles act locally to induce mucosal inflammation characterized by the Th17 immune response.

Example 6

Induction of Sepsis by Intraperitoneal Injection of High-Dose of $E.$ $coli$-Derived Extracellular Vesicles The extracellular vesicles isolated by the method of Example 3 were intraperitoneally injected once at a dose of 15, 25 or 50 µg into groups of 20 C57BL/6 (male, 6 weeks old) mice, and dead mice were counted every 12 hours.

Figure 15:
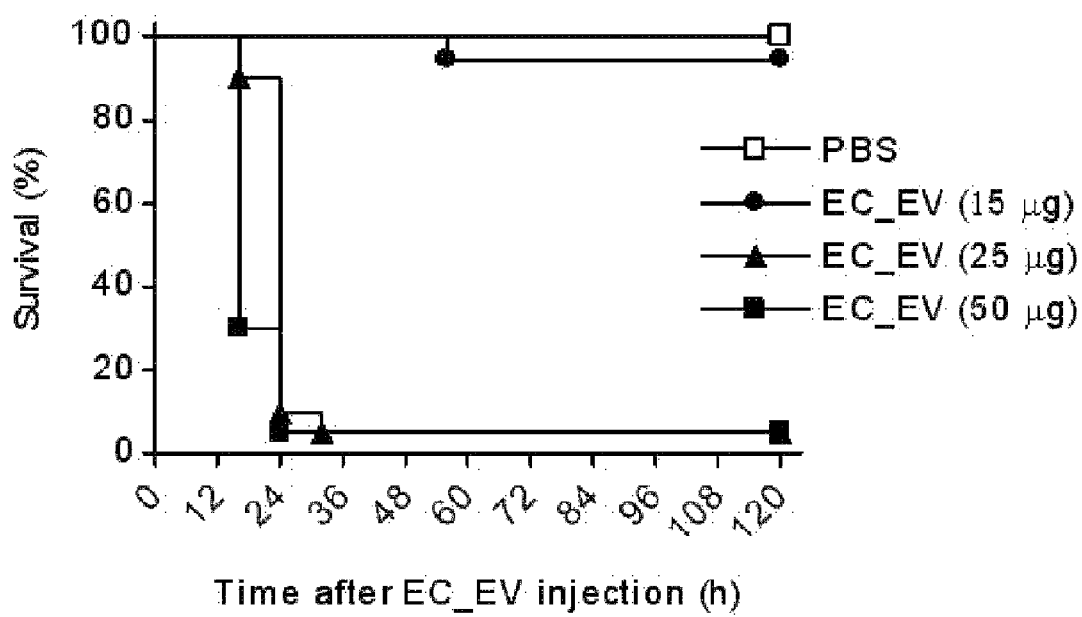
FIG. 15 is a survival curve of C57BL/6 mice (male, 6 weeks old) administered once with 15, 25 and 50 µg of $E.$ $coli$-derived extracellular vesicles (EC_EV), as monitored every 12 hours.

FIG. 15 is a survival curve of mice administered with extracellular vesicles. Upon the intraperitoneal injection of the extracellular vesicles at a dose of 25 µg or higher, 95% of the mice.

An experiment was conducted to examine whether the extracellular vesicles induced sepsis. Sepsis-related indices were analyzed after the extracellular vesicles (5 µg) isolated from mouse gut flora by the method of Example 3 were intraperitoneally injected three times every 12 hours. Six, and 24 hours after the injection of the extracellular vesicles, blood was taken from the hearts of the mice and centrifuged at 4° C. and 3,500×g for 10 min to give serum as a supernatant.

Figure 16:
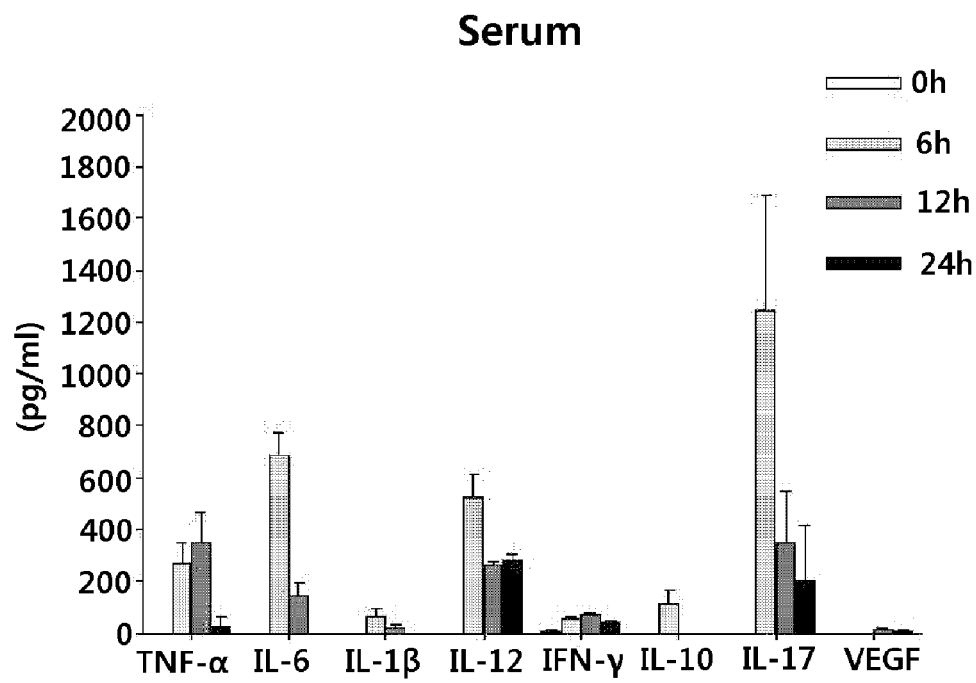
FIG. 16 shows the levels of the inflammatory cytokines TNF-$\alpha$, IL-6, IL-1$\beta$, IL-12, IFN-$\gamma$, IL-10 and IL-17 in the blood taken 6, 12 and 24 hours after $E.$ $coli$-derived extracellular vesicles are injected once times every 12 hours for 36 hours at a dose of 5 µg, as measured by ELISA.

FIG. 16 shows levels of the sepsis-related cytokines as measured by ELISA. As can be seen, the levels of TNF-α, IL-6, IL-1β, IL-12, IFN-γ, IL-10 and IL-17 were increased.

Systemic inflammatory response syndrome (SIRS), characteristic of sepsis, was evaluated in terms of the criteria breath rate, body temperature, body weight and white blood cell count.

Figure 17:
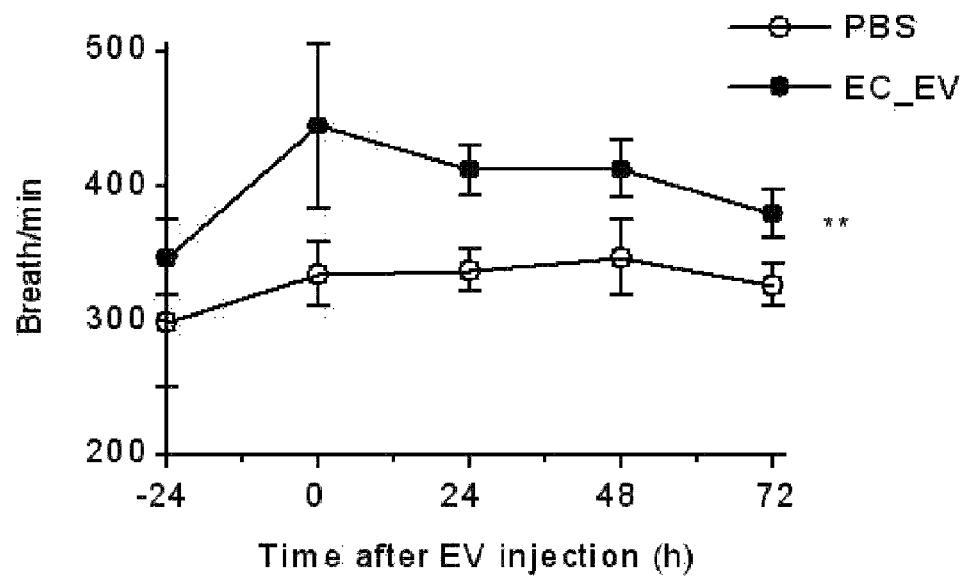
FIG. 17 shows breath rates measured every 24 hours after 5 µg of extracellular vesicles (EC_EV) is injected once per 12 hours for 36 hours.

FIG. 17 shows breath rates measured every 24 hours after the injection of extracellular vesicles (5 µg). Breath rates of the mice were determined by measuring the frequency of breathing for 3 min with a nebulizer in a chamber. The breath rate, an index for SIRS, was increased by the administration of extracellular vesicles.

Figure 18:
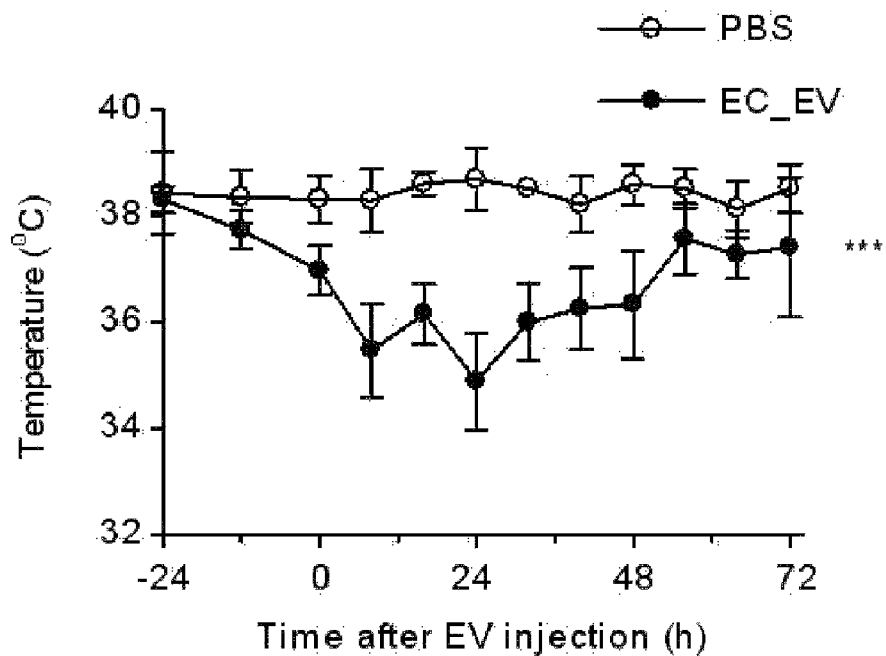
FIG. 18 shows a change in body temperature measured every 8 hours for 3 days after 5 µg of extracellular vesicles (EC_EV) is injected once per 12 hours for 36 hours.

FIG. 18 shows a change in body temperature for three days after the injection of extracellular vesicles (5 µg) as measured every 8 hours. Body temperatures were recorded on the digital display of a rectal thermometer applied to the mice. As can be seen, lowered body temperatures (hypothermia), an index for SIRS, were detected in the mice administered with extracellular vesicles.

Figure 19:
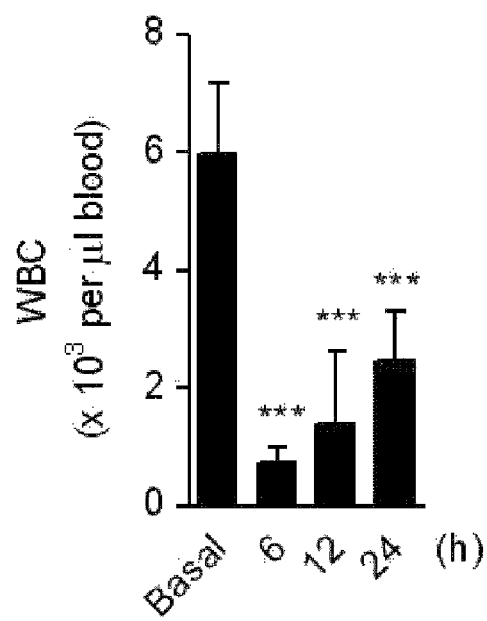
FIG. 19 shows white blood cell counts measured 6, 12 and 24 hours after $E.$ $coli$-derived extracellular vesicles (5 µg) are injected once per 12 hours for 36 hours.

FIG. 19 shows white blood cell counts measured 6, 12 and 24 hours after the injection of extracellular vesicles (5 µg). Blood taken from the heart was stored at 4° C. in an EDTA-containing tube and 10 µl of the blood sample was incubated with 90 µl of 1% HCl at 25° C. for 6 min. The white blood cells in the reaction were counted using a hemacytometer. The extracellular vesicles were observed to induce leucopenia, an index for SIRS.

Figure 20:
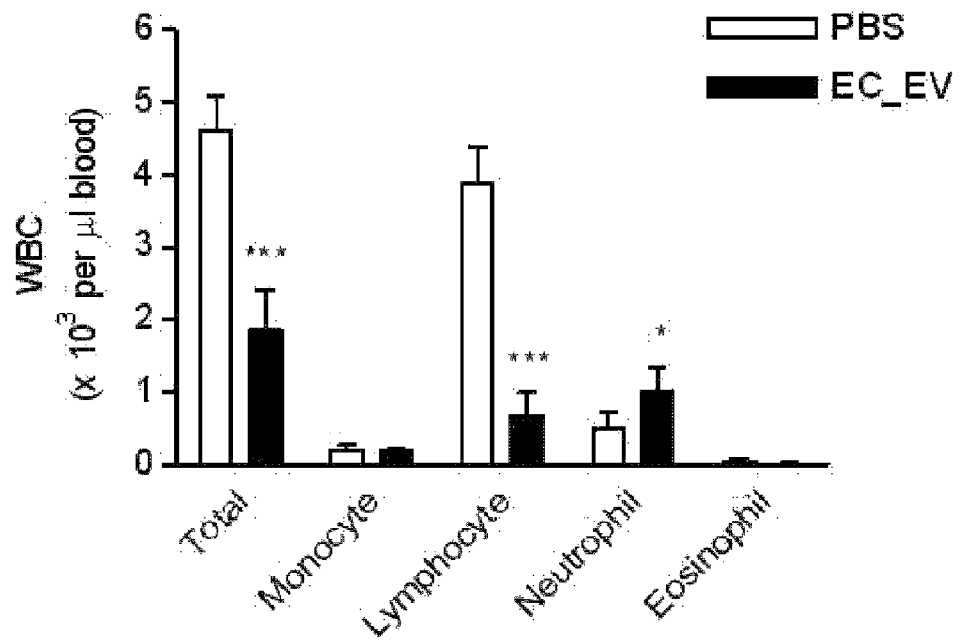
FIG. 20 shows counts of total leukocytes and each leukocyte type 12 hours after the three injections of 5 µg of $E.$ $coli$-derived extracellular vesicles at regular intervals of 12 hours.

FIG. 20 shows counts of total leukocytes and each leucocyte type 12 hours after the injection of extracellular vesicles (5 µg). Blood was taken 12 hours after the injection of extracellular vesicles and stored at 4° C. in an EDTA-containing tube. Of the blood sample, 10 µl was spread over a slide and stained with Diff Quick. Over 300 inflammatory cells were observed in a visual field magnified by 1,000 times under an optical microscope and classified as basophils, lymphocytes, neutrophils, and eosinophils. The count of total leucocytes, particularly, lymphocytes, was decreased whereas neutrophils became crowded.

To examine whether extracellular vesicles induced severe sepsis, blood pressure was measured.

Figure 21:
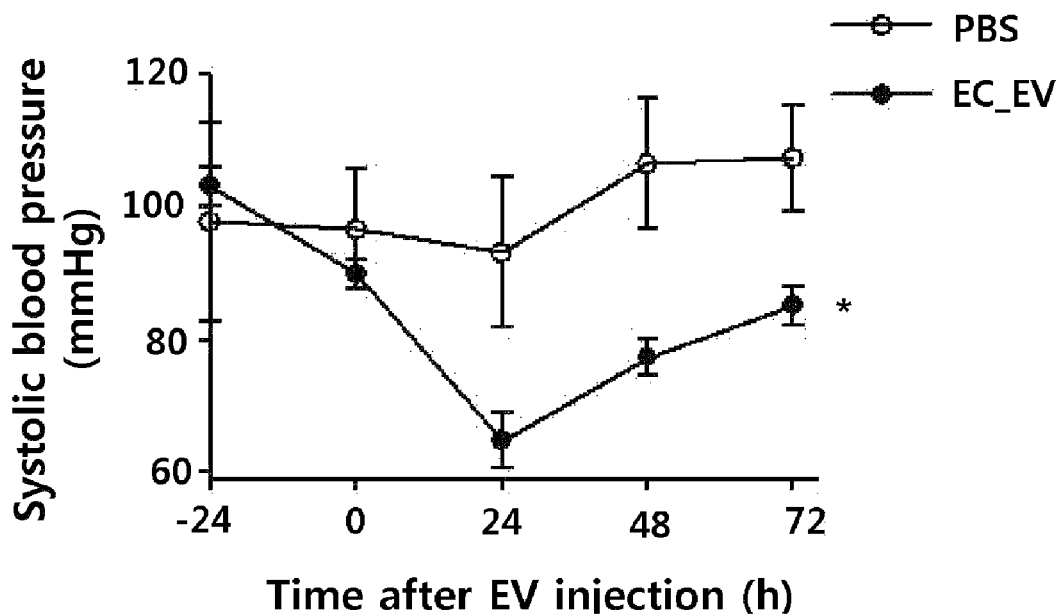
FIG. 21 shows blood pressures measured every 24 hours after the three injections of 5 µg of $E.$ $coli$-derived extracellular vesicles at regular intervals of 12 hours.

FIG. 21 shows blood pressures measured every 24 hours after the injection of extracellular vesicles (5 µg). After mice were placed on a platform, blood pressures in their tails were detected by the sensor and recorded on a computer display. As can be seen, the extracellular vesicles caused a significant decrease in blood pressure.

Taken together, these data obtained above demonstrate that the extracellular vesicles derived from gut flora, such as $E.$ $coli$, when intravascularly introduced, act as a causative factor of sepsis.

Example 7

Blood Coagulation by Intraperitoneal Injection of High-Dose of $E.$ $coli$-Derived Extracellular Vesicles An examination was made to see whether blood coagulation, observed in severe sepsis, is induced by extracellular vesicles. Given, disseminated intravascular coagulation leads to a decrease in platelet level and an increase in D-dimer level.

Figure 22:
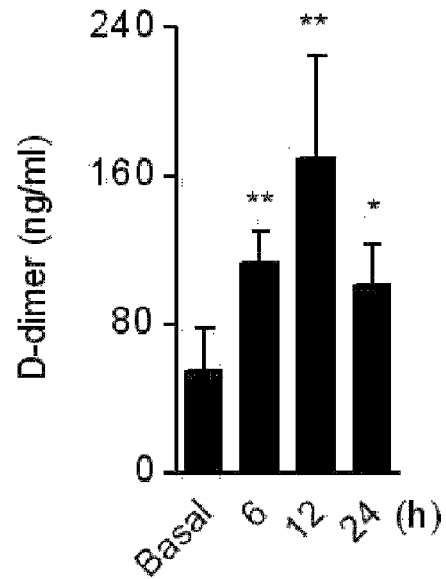
FIG. 22 shows D-dimer levels measured 6, 12 and 24 hours after the three injections of 5 µg of $E.$ $coli$-derived extracellular vesicles at regular intervals of 12 hours.

FIG. 22 shows D-dimer levels measured 6, 12 and 24 hours after the injection of extracellular vesicles (5 µg). Blood was taken from the heart 6, 12, and 24 hours after the intraperitoneal injection of the extracellular vesicles and stored at 4° C. in a sodium citrate-containing tube. D-dimer was quantitatively determined by ELISA. The level of D-dimer was observed to peak 12 hours post-injection.

Figure 23:
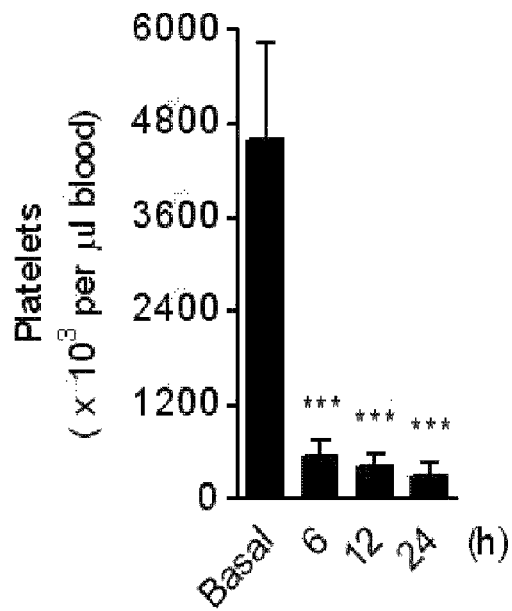
FIG. 23 shows platelet counts measured 6, 12 and 24 hours after the three injections of 5 µg of $E.$ $coli$-derived extracellular vesicles at regular intervals of 12 hours.

Also, platelet counts were examined. In this regard, 6, 12 and 24 hours after the intraperitoneal injection of extracellular vesicles, blood samples were taken from the heart and stored at 4° C. in the presence of EDTA in tubes. The blood samples were 200-fold diluted in 1% ammonium oxalate, reacted for 10 min, and counted in a hemacytometer FIG. 23 shows the occurrence of thrombocytopenia, indicative of disseminated intravascular coagulation, from 6 hours after the injection of extracellular vesicles.

These results imply that once introduced into blood vessels, gut flora-derived extracellular vesicles act as a causative factor of blood coagulation, causing disseminated intravascular coagulation.

Example 8

Activation of Vascular Endothelial Cells and Expression of Procoagulant Molecule by *E. coli*-Derived Extracellular Vesicles To examine the activation of vascular endothelial cells by *E. coli*-derived extracellular vesicles, HUVEC (Human Umbilical Vein Endothelial Cell) was seeded at a density of $5 \times 10^5$ cell/well into 6-well plates and maintained for 24 hours, after which the cells were incubated with extracellular vesicles (0.1, 1, 5, 10, 20 ng/ml) for 8 hours in a 37° C. incubator. After removal of the culture medium, the cells were washed once with PBS and lysed in cell lysis buffer for 10 min. Centrifugation at 4° C. and 13,000×rpm for 10 min gave total cell proteins. These were mixed in such an amount with 5× loading dye (250 mM Tris-HCl, 10% SDS, 0.5% bromophenol blue, 50% glycerol) that the loading dye was diluted to 1× before boiling at 100° C. for 10 min. The protein samples were loaded onto 10% polyacrylamide gel and run at 100 V for 2 hours by electrophoresis, followed by transfer onto a PVDF (polyvinylidene fluoride) membrane at 300 mA for 2 hours. The membrane was blocked for 2 hours with a 3% skimmed milk solution in PBS before incubation with anti-ICAM-1 and anti-beta-actin antibodies 4° C. for 12 hours. Then, the membrane was washed three times with 0.05% Tween 20/PBS and treated with perodixase-conjugated secondary antibody at room temperature for 1 hour. After washing with 0.05% Tween 20/PBS for 30 min, the protein was detected with ECL (enhanced chemiluminescence, Amersham Co. No. RPN2106) substrate. In the total proteins, the level of ICAM-1 was increased, compared to beta-actin. ICAM-1, an intercellular adhesion molecule, is activated in vascular endothelial cells upon the activation of vascular endothelial cells such as in various immune responses and coronary artery diseases and is known for its importance in facilitating the infiltration of immune cells into tissues.

Figure 24:
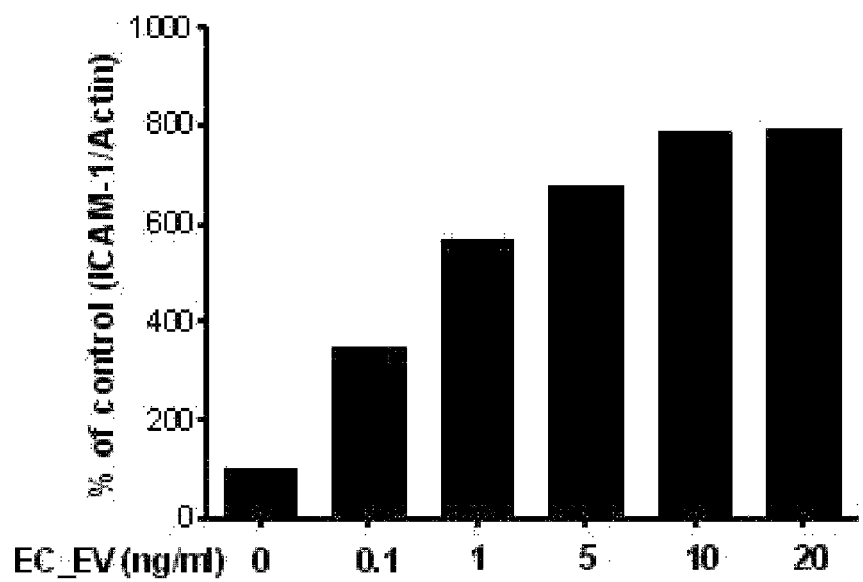
FIG. 24 shows the levels of ICAM-1 increased in a dose dependent manner when vascular endothelial cells are treated with 0.1, 1, 5, 10 and 20 ng/ml of $E.$ $coli$-derived extracellular vesicles (EC_EV).

As shown in FIG. 24, the extracellular vesicles activate vascular endothelial cells and increase the level of ICAM-1.

Figure 25:
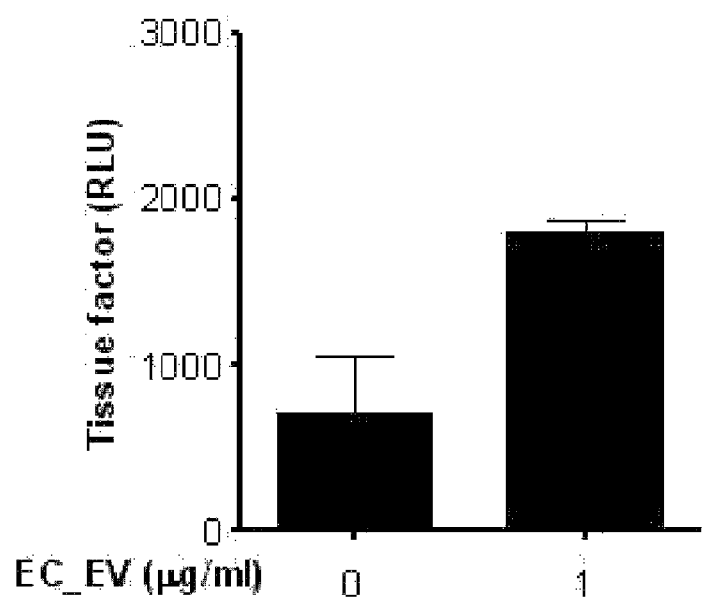
FIG. 25 shows the secretion of the procoagulant molecule tissue factor when vascular endothelial cells are treated with 1 ng/ml $E.$ $coli$-derived extracellular vesicles(EC_EV).

To examine whether *E. coli*-derived extracellular vesicles induce the expression of procoagulant molecules, HUVEC (Human Umbilical Vein Endothelial Cell) was seeded at a density of $5 \times 10^5$ cell/well into 6-well plates and maintained for 24 hours, after which the cells were incubated with extracellular vesicles (1 ng/ml) for 12 hours in a 37° C. incubator. After being harvested, the culture media were centrifuged at 4° C., 500×g for 10 min and then at 4° C., 3000×g for 20 min. A tissue factor, which is a procoagulant molecule, was quantitatively analyzed. To this end, the supernatant was aliquoted in an amount of 100 μl per well into ELISA plates and the tissue factor was allowed to adhere to the surface at 4° C. for 12 hours, followed by treatment with an anti-tissue factor antibody at room temperature for 2 hours. The plates were washed three times with 0.05% Tween 20/PBS and treated with perodixase-conjugated secondary antibody at room temperature for 1 hour. After washing with 0.05% Tween 20/PBS for 30 min, the protein was detected with ECL (enhanced chemiluminescence, Amersham Co. No. RPN2106) substrate. As can be seen in FIG. 25, treatment with extracellular vesicles induced the procoagulant molecule tissue factor to be significantly secreted.

Example 9

Induction of Pneumonia and Emphysema by High-Dose of *E. coli*-Derived Extracellular Vesicles

*E. coli*-derived extracellular vesicles (10 μg) were stained with cyanin-7 (cy7) before the intraperitoneal injection thereof into mice. Six hours post-injection, the locations of the *E. coli*-derived extracellular vesicles in the body were detected using the Kodak image station.

Figure 26:
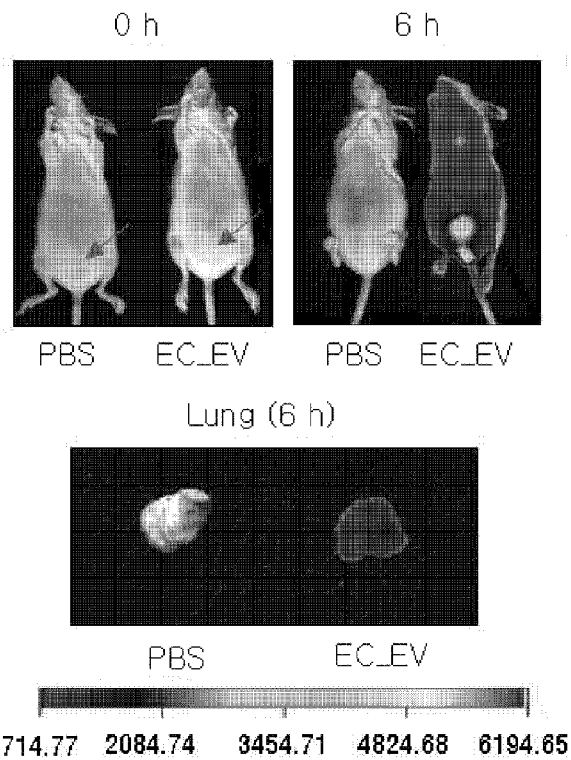
FIG. 26 shows fluorescence photographs of whole mouse body, taken by the Kodak image station 6 hours after $E.$ $coli$-derived extracellular vesicles (10 µg) stained with cyanin-7 (cy7) are intraperitoneally injected to the mice.

FIG. 26 shows fluorescence photographs revealing the distribution of the extracellular across the body and particularly in the lung.

*E. coli*-derived extracellular vesicles (10, 20 μg) were stained with DiO before the intraperitoneal injection thereof into mice. Six hours post-injection, blood and the lung was removed.

Figure 27:
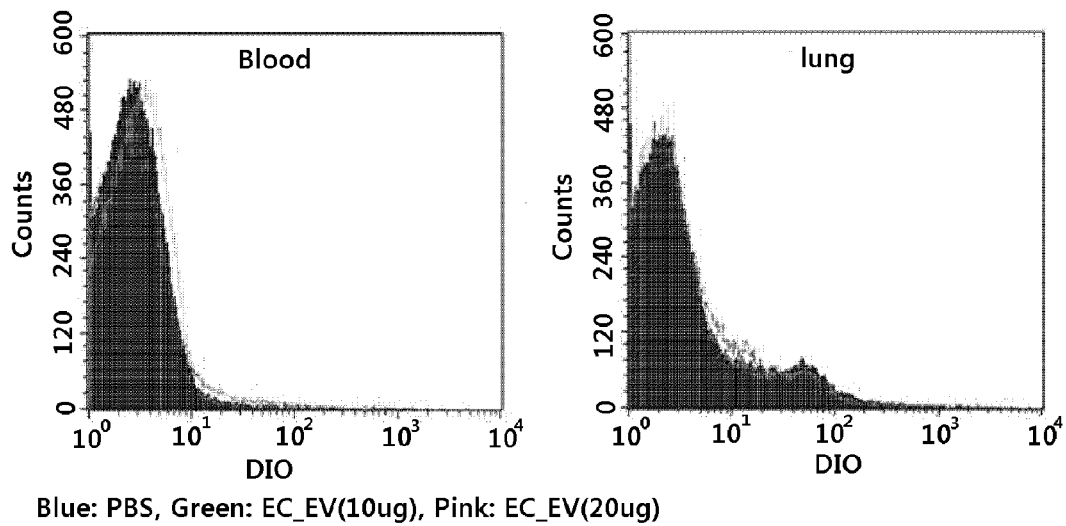
FIG. 27 shows ratios of extracellular vesicle-carrying blood cells to pulmonary cells as analyzed by flow cytometry (FACS) when RBC (red blood cells) were removed from the blood and the lung using RBC lysis buffer 6 hours after $E.$

FIG. 27 shows ratios of extracellular vesicle-carrying blood cells to pulmonary cells as analyzed by flow cytometry (FACS) after RBC (red blood cells) were removed from the blood and the lung using RBC lysis buffer. As can be seen, the ratio of fluorescent cells was increased, indicating that the extracellular vesicles are spread over the body including the lungs as they are carried by cells.

In order to analyze pulmonary inflammation, the lungs were excised 6, 12 and 24 hours after the injection of extracellular vesicles (5 μg), weighed, and left at 65° C. for hours in an incubator. Pulmonary inflammation was evaluated by a wet-to-dry ratio analysis.

FIG. 28 is a graph showing the wet-to-dry ratios of lung tissues. As is apparent from the data, pulmonary inflammation took place 6 hours after the intraperitoneal injection of the extracellular vesicles.

Six, 12 and 24 hours after the injection of extracellular vesicles (5 μg), BAL fluid was taken from the mice and its inflammatory cells were counted. Mice were anesthetized by the intraperitoneal injection of ketamine. A vertical midline incision was made through which the trachea was opened so that a catheter could be inserted into the airway, followed by ligation. The airway was washed twice with 1 mL of PBS. The bronchoalveolar lavage, (BAL) fluid thus obtained was centrifuged at 4° C. and 3,000 rpm for 10 min and the cell pellet was suspended in PBS. Total inflammatory cells were counted under an optical microscope. The cells were then spread over a slide by cytospin and stained with Diff Quick. Over 300 inflammatory cells were observed in a visual field magnified by 1000 times under an optical microscope and classified as basophils, lymphocytes, neutrophils, and eosinophils. Their counts were determined.

FIG. 29 is a graph showing inflammatory cell counts in BAL fluid. As is apparent from the data, extracellular vesicles increased the population of inflammatory cells, particularly macrophages.

The lungs were excised 6, 12 and 24 hours after the injection of extracellular vesicles (5 μg), fixed in 4% formaldehyde, sliced, stained with hematoxylin-eosin, and observed under an optical microscope. FIG. 30 provides the optical images. As seen in the images, the alveoli were completed by the extracellular vesicles, indicating that emphysema, together with pulmonary inflammation, is generated by gut flora-derived extracellular vesicles.

These diseases resulted from the assignment of the gut flora-derived extracellular vesicles to various organs through blood with the concomitant induction of the onset of inflammation and tissue injury. Therefore, it can be inferred that the gut flora-derived extracellular vesicles might act as a pathogenic agent of inflammatory diseases, the causative factors of which are unknown.

Example 10

Induction of Hypertension and Osteoporosis by Intraperitoneal Injection of Low-Dose of E. coli-Derived Extracellular Vesicles for Extended Period of Time To examine the induction of chronic diseases upon repeated exposure to a low dose of the E. coli-derived extracellular vesicles, the extracellular vesicles (0.1, 1 µg) were intraperitoneally injected twice a week for 18 weeks.

FIG. 31 is a graph showing changes in blood pressure upon repeated exposure to low doses of E. coli-derived extracellular vesicles. As can be seen, hypertension was caused by long-term administration of the extracellular vesicles.

Also, to examine whether repeated exposure to a low dose of the E. coli-derived extracellular vesicles induced the onset of osteoporosis, the intraperitoneal injection of the extracellular vesicles (1 µg) was carried out twice a week for 18 weeks. The long bones taken from the leg were fixed overnight in a fixing solution and washed twice with saline, after which dehydration was performed in a series of graded ethanol solutions (30, 50, 70, 90, and 100% ethanol, 1 hour each). The dehydration agent was then replaced by propylene oxide to gradually infiltrate the bone with a polymer. In this regard, the bone was immersed twice for 1 hour in a series of mixtures containing propylene oxide to polymer at a ratio of 3:1, 1:1 and 1:3. After the remaining propylene oxide was evaporated under a hood, the bone was immersed in a 100% polymer solution and incubated overnight in a 65° C. oven to allow polymerization. All X-ray tomography images of the bone sample were acquired by Synchroton radiation X-ray microscopy using the 7B2 beamline at Pohang Light Source (PLS). A total of 1200 photographs were taken with the 180° rotation of the polymer-embedded bone on the sample stage of the Synchroton radiation X-ray microscope. Images were obtained by the absorption contrast effect of Synchroton radiation X-ray microscopy with the distance between the sample stage and the scintillator set to 10 cm. Next, 3D reconstruction of the images was performed using Octopus and Amira programs. Out of the 1200 images, representative tomographic slice images were compared to each other.

FIG. 32 shows the onset of osteoporosis, characterized by the destruction of bone architecture upon repeated exposure to a low dose of the extracellular vesicles for a long period of time.

The results indicate that when the gut flora-derived extracellular vesicles are repetitively absorbed into the blood and systemically distributed, they can induce the onset of hypertension and osteoporosis.

Example 11

Role of IL-6 in E. coli-Derived Extracellular Vesicle-Induced Onset of Sepsis

The E. coli-derived extracellular vesicles (25 µg) separated by the method of Example 3 were intraperitoneally injected once into normal mice (C57BL/6, male, 6 weeks old) and IL-6-knockout mice (C57BL/6, male, 6 weeks old), after which dead mice were counted every 12 hours. Survival rates are depicted in FIG. 33. In contrast to normal mice, the IL-6-knockout mice did not die of 25 µg of the extracellular vesicles.

The lung was excised 6, 12 and 24 hours after three injections of extracellular vesicles (5 µg) for 12 hours and pathologically analyzed as in Example 9. FIG. 34 shows photographs of lung slices, revealing that in contrast to normal mice the IL-6-knockout mice did not undergo the extracellular vesicle-induced destruction of the lung tissues at all.

Based on these results, it can be inferred that IL-6 acts as an important mediator that is responsible for the gut flora-derived extracellular vesicles-induced onset of sepsis as well as inflammatory diseases on various organs.

Example 12

Establishment of In vitro Screening System for Drug Candidates for Prevention or Treatment of Gut Flora-Derived Extracellular Vesicle-Induced Disease The previous Examples demonstrate that the inflammatory cytokines induced by the mouse gut flora-derived extracellular vesicles are greatly involved in the generation of various diseases. Based on this fact, also, a substance inhibitory of the inflammatory cytokines, especially IL-6 may be used as a candidate drug for the prevention or treatment of gut flora-derived extracellular vesicles-caused diseases and therefore the selection of such substance is very important.

FIG. 35 is a schematic diagram showing the discovery of substances inhibitory of the gut flora-derived extracellular vesicles-induced release of IL-6. The mouse macrophages (RAW 264.7) were treated for 15 hours with the gut flora-derived extracellular vesicles (100 ng/ml) alone, separated by the method of Example 3, or in combination with a drug candidate (10 µM), in a 37° C. incubator. The culture media was collected and centrifuged at 4° C., 500×g for 10 min and then at 4° C., 3000×g for 20 min. IL-6 in the supernatant was quantitatively analyzed by ELISA. These processes account, at least in part, for a method for in vitro screening drug candidates inhibitory of the gut flora-derived extracellular vesicle-induced secretion of IL-6, by which drug candidates preventive or therapeutic of gut flora-derived extracellular vesicles-caused diseases can be provided.

Example 13

In Vitro Anti-Inflammatory Effect of the Kinase Ihhibtor Discovered by the In vitro Screening System According to the method established in Example 12, mouse macrophages (RAW 264.7) were treated with neither extracellular vesicles nor any drug candidate (negative control), with E. coli-derived extracellular vesicles (0.1 µg/ml) alone (positive control) or with the extracellular vesicles (0.1 µg/ml) in combination with 10 µM of one selected from among 80 different kinase inhibitors ((kinase inhibitor library, BIOMOL No. 2832: PD-98059, U-0126, SB-203580, H-7, H-9, AG-494, AG-825, Lavendustin A, RG-14620, Tytphostin 23, Tytphostin 25, Tytphostin46, Tytphostin47, Tytphostin 51, Tytphostin 1, Tytphostin 9, Tytphostin AG 1288, Tytphostin AG 1478, Tytphostin AG 1295, HNMPA, Damnacanthal, Piceatannol, AG-490, AG-126, AG-370, AG-879, LY 294002, Wortmannin, GF 109203×, Hypericin, Sphingosine, H-89, H-8, HA-1004, HA-1077, HDBA, KN-62, KN-93, ML-7, ML-9,2-Aminopurine, N9-Isopropyl-olomoucine, Olomoucine, iso-olomoucine, Roscovitine, LFM-A13, SB-202190, ZM 336372, SU 4312, AG-1296, Rottlerin, Genistein, Daiazein, Erbstatin analog, Quercetin dehydrate, SU 1498, ZM 449829, DRB (5,6-Dichloro-1-b-D-ribofuranosylbenzimidazole), HBDDE (2,2',3,3',4,4'-Hexahydroxy-1,1'-biphenyl-6,6'-dimethanol dimethyl ether), Indirubin, Indirubin-3'-monoxime, Y-27632, Kenpaullone, Terreic acid, BML-257, BML-259, Apigenin, BML-265 (Erlotinib analog), Rapamycin). After 15 hours of treatment, IL-6 was quantitatively analyzed by ELISA.

In FIG. 36, the levels of IL-6 upon treatment with each of the kinase inhibitors are expressed as percentages of that of the positive control.

Of the 80 different kinase inhibitors, as can be seen, 11 (4; H-7, 29; LY294002, 31; GF109203X, 42; ML-7, 43; ML-9, 64; ZM449829, 66; DRB (5,6-Dichloro-1-b-D-ribofuranosylbenzimidazole), 70; Indirubin-3' monoxime. 72; Kenpaullone, 77; BML-259, 78; Apigenin) were found to reduce the level of IL-6 to below 50% of that of the positive control.

FIG. 37 is a graph of IL-6 levels in cell cultures treated with one or more of the kinase inhibitors Damnacanthal, LY294002 and GF109203X (each maintained at 10 μM) in the presence of extracellular vesicles (100 ng/ml), showing that co-treatment with two or more of the kinase inhibitors exerts a synergistic effect on the inhibition of IL-6 secretion.

Example 14

In vitro Anti-Inflammatory Effect of Phosphatase Inhibitor Discovered by the In vitro Screening System FIG. 38 shows IL-6 levels of the cell cultures as percentages of those of the positive control when the cell cultures were treated with each of the 30 different phosphatase inhibitors (phosphatase inhibitor library, BIOMOL No. 2834: Cantharidic acid, Cantharidin. Endothall, Benzylphosphonic acid, L-p-Bromotetramisole oxalate, RK-682, RWJ-60475, RWJ-60475 (AM)3, Levamisole HCl, Tetramisole HCl, Cypermethrin, Deltamethrin, Fenvalerate, Tyrphostin 8, CinnGEL, CinnGEL 2 Me, BN-82002, Shikonin, NSC-663284, Cyclosporin A, Pentamidine, BVT-948, B4-Rhodanine, BML-268, Dioxophenanthrene, BML-260, PD-144795, BML-267, BML-267 Ester, OBA, OBA Ester, Gossypol, Alendronate) as in Example 13. PD-144795 was discovered as a drug candidate as it reduced the IL-6 level to below 50% of that of the positive control.

FIG. 39 is a graph of IL-6 levels in mouse macrophage cultures that were treated with 0.1, 1, 5, and 10 μM PD-144795 in the presence of 100 ng/ml E. coli-derived extracellular vesicles as in Example 13, showing that the drug candidate inhibits IL-6 secretion in a dose-dependent manner.

Example 15

In Vitro Anti-Inflammatory Effect of Prodrugs Discovered by the In Vitro Screening System FIG. 40 shows IL-6 levels of the cell cultures as percentages of those of the positive control when the cell cultures were treated with each of 100 different prodrugs (acetaminophen, acetylcysteine, allopurinol, alprenolol HCl, amitriptyline HCl, atropine, bretylium tosylate, bromopheniramine, budesonide, buspirone HCl, cefuroxime, chloral hydrate, chlorpromazine HCl, cimetidine, clomipramine HCl, clotrimazole, cyclobenzaprine, desipramine HCl, diclofenac, diflunisal, diltiazem, diphenhydramine HCl, disopyramine, disulfuram, D-mannitol, doxepin, doxycycline hydrate, doxylamine succinate, edrophonium chloride, enalapril maleate, famotidine, fenbufen, fenofibrate, fenoprofen calcium salt hydrate, flunarizine dihydrochloride, fluphenazine dichloride, flurbiprofen, furosemide, gemfibrozil, gliclazide, glipizide, haloperidol, hydrochlorothiazide, hydroflumethiazide, hydroxyzine HCl, ibuprofen, imipramine HCl, indapamide, indole-2-carboxylic acid, indomethacin, ipratropium, ketoprofen, ketorolac tris salt, maprotiline HCl, meclofenamic acid, melatonin, metformin, methapyrilene HCl, methimazole, methocarbamol, metoclopramide HCl, metronidazole, nabumetone, naproxen, neostigmine Br, niacin, nicardipine HCl, nifedipine, nitrofurantoin, nizatidine, norethindrone, nortriptyline, orphenadrine HCl, oxybutynin, phenformin HCl, phenylbutazone, phenyloin, piroxicam, prednisone, probenecid, propranolol HCl, pyridostigmine Br, ranitidine HCl, spironolactone, sulfameth, sulpiride, tenoxicam, terfenadine, theophylline, ticlopidine HCl, tolazamide, tolazoline, tolbutamide, tolfenamic acid, tramadol HCl, tranylcypromine, trazodone HCl, triamterene, trichlormethiazide, tripelennamine HCl, verapamil, warfarin) as in Example 13. Of them, 14 (10; Amitriptyline, 39; Cyclobenzaprine, 41; Desipramine, 54; Doxepin, 72; Fluphenazine dichloride, 82; Haloperidol, 89; Imipramine, 101; Maprotiline, 132; Orphenadrine, 165; Terfenadine, 173; Tolfenamic acid, 179; Trazodone, 187; Trichlormethiazide, 188; Verapamil) were discovered as drug candidates as they reduced the IL-6 level to below 80% of that of the positive control.

FIG. 41 is a graph showing IL-6 levels obtained by treating mouse peritoneal macrophages ex vivo with the 14 prodrugs discovered by the in vitro screening system, confirming the inhibitory effect of 11 (10; Amitriptyline, 39; Cyclobenzaprine, 41; Desipramine, 54; Doxepin, 72; Fluphenazine dichloride, 82; Haloperidol, 89; Imipramine, 101; Maprotiline, 132; Orphenadrine, 165; Terfenadine, 173; Tolfenamic acid, 179; Trazodone HCl) on IL-6 release.

Example 16

In Vivo Anti-Inflammatory Effect of Prodrugs Discovered by the In Vitro Screening System In vivo assay was performed to examine whether the prodrugs discovered in Example 15 exert anti-inflammatory effects in the body. To this end, the sepsis mouse models that were established by the intraperitoneal injection of 5 μg of E. coli-derived extracellular vesicles into C57BL/6 mice (male, 6 weeks old, 4 mice in each group) as in Example 6 was intraperitoneally injected with Haloperidol and Doxepein at a dose of 10 mg/kg, each. Sera were taken 6 hours later.

FIG. 42 is a graph showing serum IL-6 levels as quantitatively analyzed by ELISA, demonstrating that the E. coli-derived extracellular vesicle-induced secretion of the inflammatory cytokine IL-6 is effectively suppressed by Haloperidol and Doxepein, both discovered by the in vitro screening system.

From these results, it is apparent that the in vitro drug screening system using the gut flora-derived extracellular vesicles, established in Example 12, is a very useful method by which drugs can be effectively selected for the prevention or treatment of gut flora-derived extracellular vesicle-induced diseases.

Example 17

Immunological Properties of E. coli-Derived Extracellular Vesicle Vaccines

The E. coli-derived extracellular vesicles isolated according to the method of Example 3 were intraperitoneally injected at a dose of 1 μg to C57BL/6 (male, six weeks old, 10 in each group) once a week for three weeks. Blood samples were taken from the mice 6 hours, 24 hours and 7 days after each injection and assayed for their antibodies specific for extracellular vesicles if any. The mouse serum was 1:500 diluted in 1% BSA/PBS and placed in black 96-well plates coated with 200 ng of E. coli-derived vesicles per well. After incubation at room temperature for 2 hours, an observation was made of the immunological change with a peroxidase-conjugated anti-mouse antibody.

FIG. 43 is a graph in which levels of E. coli-derived extracellular vesicle-specific antibodies in the mouse blood are plotted against time. The extracellular vesicle-specific antibodies started to form 7 days after the first injection of extracellular vesicles and was amplified by the second and the third injection of the extracellular vesicles, with a peak at 7 days after the third injection.

Seven days after the three injections of E. coli-derived extracellular vesicles were completed, splenocytes were isolated from the mice. The splenocytes ($2 \times 10^4$) were incubated for 72 hours with 100 ng of E. coli-derived extracellular vesicles, followed by ELISA to quantitatively analyze IFN-γ, IL-17 and IL-4, all secreted from splenocytes.

FIG. 44 shows the levels of IFN-γ secreted from mouse splenocytes upon treatment with E. coli-derived extracellular vesicles. As can be seen, a higher level of IFN-γ was secreted from the splenocytes of the. E. coli-derived extracellular vesicle-immunized group, compared to the sham group.

FIG. 45 shows the levels of IL-17 secreted from mouse splenocytes upon treatment with E. coli-derived extracellular vesicles. As can be seen, a higher level of IL-17 was secreted from the splenocytes of the. E. coli-derived extracellular vesicle-immunized group, compared to the sham group.

FIG. 46 shows the levels of IL-4 secreted from mouse splenocytes upon treatment with E. coli-derived extracellular vesicles. As can be seen, immunization with E. coli-derived extracellular vesicles had no effect on the secretion of IL-4.

From these results, it is confirmed that immunization with E. coli-derived extracellular vesicles induces the defense system against bacterial infection, including the antibody production of B cells and the T cell immune response. Particularly, as for the T cell immune response, the Th1 immune response responsible for IFN-γ secretion and the Th17 immune response responsible for IL-17 secretion, both playing an important role in defense against bacterial infection, were effectively induced by immunization with E. coli-derived extracellular vesicles.

Example 18

Efficacy of E. coli-Derived Extracellular Vesicle Vaccine Against E. Coli Infection-Induced Sepsis For use in evaluating the efficacy of E. coli-derived extracellular vesicle vaccines, E. coli infection-induced animal models of sepsis were established. E. coli was intraperitoneally injected at a dose of $1 \times 10^6$, $1 \times 10^8$ and $1 \times 10^{10}$ CFU into C57BL/6 mice (male, 6 weeks old, 10 mice in each group) the survidal which were then monitored at regular intervals of 8 hours for 5 days.

FIG. 47 shows survival rates of the mice infected with E. coli. As shown in this graph, mice were dead with 24 hours after the injection of E. coli at a dose of $1 \times 10^{10}$ CFU, but did not die of $1 \times 10^6$ or $1 \times 10^8$ CFU of E. coli.

E. coli-derived extracellular vesicles were intraperitoneally injected once a week for three weeks at a dose of 0.5 and 1 μg to C57BL/6 mice (male, 6 weeks old, 10 mice in each group) according to the method of Example 17. Seven days after the three immunizations of the E. coli-derived extracellular vesicles, the mice were intraperitoneally challenged with $1 \times 10^{10}$ CFU of E. coli and their survival rates were monitored at regular intervals of 8 hours for 5 days.

FIG. 48 shows the efficacy of the E. coli-derived extracellular vesicle vaccines against the E. coli infection-induced sepsis of FIG. 47. Five days after the challenge, the mice were observed to survive at a rate of 20% when not immunized with the E. coli-derived extracellular vesicles, but the survival rate was increased to 80-100% in the mice immunized with the E. coli-derived extracellular vesicles.

As described in Example 17, E. coli-derived extracellular vesicles were intraperitoneally injected at a dose of 1 μg once a week for three weeks to mice which were then intraperitoneally challenged with $1 \times 10^{10}$ CFU of E. coli. Six hours later, E. coli in ascites and blood were counted and the results are depicted in FIG. 49. Also, blood IL-6 levels determined by ELISA are shown in FIG. 50 and lung tissue images are given in FIG. 51.

FIG. 49 shows E. coli CFU in mice challenged with and without E. coli-derived extracellular vesicles. After E. coli infection, a significantly small number of E. coli was detected in blood and ascites from the mice immunized with E. coli-derived extracellular vesicles, compared to those immunized without E. coli-derived extracellular vesicles.

FIG. 50 shows blood IL-6 levels of mice immunized with or without E. coli-derived extracellular vesicles as measured 6 hours after infection with $1 \times 10^8$ CFU of E. coli. As can be seen, the level of the inflammatory cytokine IL-6 was significantly increased in the serum of E. coli-infected mice, but a greatly decresed level was detected if the mice had been immunized with E. coli-derived extracellular vesicles.

FIG. 51 shows images of the lung tissues excised 6 hours after E. coli infection. When introduced into blood, E. coli was observed to destroy pulmonary cells whereas histopathologcial samples from the mice vaccinated with E. coli-derived extracellular vesicles were similar to those from normal mice.

These data demonstrate that extracellular vesicles derived from E. coli of gut flora can be used as a vaccine for effectively preventing E. coli infections.

Example 19

Efficacy of E. coli-Derived Extracellular Vesicle Vaccines Against E. Coli-Derived Extracellular Vesicle-Induced Sepsis E. coli-derived extracellular vesicles were intraperitoneally injected once a week for three weeks at a dose of 1 μg to C57BL/6 mice (male, 6 weeks old, 10 mice in each group) according to the method of Example 17. When sepsis was induced by E. coli-derived extracellular vesicels as described in Example 6, the efficacy of the E. coli-derived extracellular vesicle vaccine was evaluated. In this regard, days after the completion of vaccination with E. coli-derived extracellular vesicles, E. coli-derived extracellular vesicles were intraperitoneally injected at a dose of 5 μg once every 12 hours for 36 hours, with sepsis-related indices analyzed.

FIGS. 52 to 54 show efficacies of E. coli-derived extracellular vesicle vaccines against the same sepsis induced by E. coli-derived extracellular vesicles as in Example 6.

FIG. 52 shows the levels of IL-6 in the sera of mice as measured 6 hours after three injections of E. coli-derived extracellular vesicles (5 μg). As can be seen, blood IL-6 levels were significantly decreased in the mice immunized with *E. coli*-derived extracellular vesicles, as compared to non-immunized mice.

FIG. 53 shows a change in body temperature, which constitutes one criterion for sepsis. Three injections of 5 μg of *E. coli*-derived extracellular vesicles reduced body temperatures, but did not induce hypothermia in the mice that were immunized once a week for three weeks with 1 μg of *E. coli*-derived extracellular vesicles.

FIG. 54 shows thrombocytopenia observed in severe sepsis. Three injections of 5 μg of *E. coli*-derived extracellular vesicles reduced the population of platelets, but the thrombocytopenia was alleviated by immunization with 1 μg of *E. coli*-derived extracellular vesicles once a week for three weeks.

Taken together, the data obtained above indicate that *E. coli*-derived extracellular vesicles can be used as an effective vaccine against diseases caused by *E. coli*-derived extracellular vesicles.

Example 20

Immunological Properties of *Klebsiella*-Derived Extracellular Vesicle Vaccines

The *Klebsiella*-derived extracellular vesicles isolated according to the method of Example 3 were intraperitoneally injected at a dose of 100 ng or 1 μg to C57BL/6 (male, six weeks old, 5 in each group) once every five days for 15 days. Blood samples were taken from the mice three days after the final challenge and antibodies specific for *Klebsiella*-derived extracellular vesicels were quantitatively analyzed. The results are shown in FIG. 55. T cells were isolated from the spleen, followed by quantitative analysis of IFN-γ and IL-17 therein. The results are depicted in FIG. 56.

FIG. 55 is a graph showing the production of *Klebsiella*-derived extracellular vesicle-specific antibodies in the blood taken from mice immunized with *Klebsiella*-derived extracellular vesicles. *Klebsiella*-derived extracellular vesicle-specific antibodies were produced in a dose dependent manner.

FIG. 56 is a graph showing a change in the population of $CD3^+CD4^+IFN-\gamma^+$ T cells out of spleen T cells after treatment with *Klebsiella*-derived extracellular vesicles. A larger number of $CD3^+CD4^+IFN-\gamma^+$ T cells were detected in the mice immunized with *Klebsiella*-derived extracellular vesicles than in non-immunized mice.

FIG. 57 is a graph showing a change in the population of $CD3^+CD4^+IL17^+$ T cells out of spleen T cells after treatment with *Klebsiella*-derived extracellular vesicles. A larger number of $CD3^+CD4^+IL17^+$ T cells were detected in the mice immunized with *Klebsiella*-derived extracellular vesicles than in non-immunized mice.

As is understood from the data of FIGS. 55 to 57, immunization with *Klebsiella*-derived extracellular vesicles induces the defense system against bacterial infection, including the antibody production of B cells and the T cell immune response. Particularly, as for the T cell immune response, the Th1 immune response responsible for IFN-γ secretion and the Th17 immune response responsible for IL-17 secretion, both playing an important role in defense against bacterial infection, were effectively induced by immunization with extracellular vesicle vaccines.

Example 21

Efficacy of *Klebsiella*-Derived Extracellular Vesicle Vaccine against *Klebsiella* Infection-Induced Sepsis For use in evaluating the efficacy of *Klebsiella*-derived extracellular vesicle vaccines, *Klebsiella* infection-induced animal models of sepsis were established. *Klebsiella* was intraperitoneally injected at a dose of $1\times10^6$, $1\times10^8$ and $1\times10^8$ CFU into C57BL/6 mice (male, 6 weeks old, 5 mice in each group) the survidal which were then monitored at regular intervals of 8 hours for 5 days.

FIG. 58 shows survival rates of the mice infected with *Klebsiella*. As shown in this graph, mice were dead with 24 hours after the injection of *E. coli* at a dose of $1\times10^8$ CFU, but did not die of $1\times10^6$ or $1\times10^8$ CFU of *Klebsiella*.

To evaluate *Klebsiella*-derived extracellular vesicles as a vaccine against *Klebsiella* infection, *Klebsiella*-derived extracellular vesicles were intraperitoneally injected once every 5 days for 15 days at a dose of 1 μg to C57BL/6 mice (male, 6 weeks old, 5 mice in each group). Three days after the three immunizations of the *Klebsiella*-derived extracellular vesicles, the mice were intraperitoneally challenged with $1\times10^8$ CFU of *Klebsiella* and their survival rates were monitored at regular intervals of 8 hours for 5 days.

FIG. 59 shows the efficacy of the *Klebsiella*-derived extracellular vesicle vaccines against the *Klebsiella* infection-induced sepsis. Five days after the challenge, the mice were observed to survive at a rate of 20% when not immunized with the *Klebsiella*-derived extracellular vesicles, but the survival rate was increased to 100% in the mice immunized with the *Klebsiella*-derived extracellular vesicles.

These data demonstrate that extracellular vesicles derived from *Klebsiella* of gut flora can be used as a vaccine for effectively preventing the onset of diseases caused by *Klebsiella*-derived extracellular vesicles.

Example 22

Immunology Upon Combined Administration with *E. coli*- and *Klebsiella*-Derived Extracellular Vesicles

*E. coli*-derived extracellular vesicles, *Klebsiella*-derived extracellular vesicles, or *E. coli*- and *Klebsiella*-derived extracellular vesicles, all isolated according to the method of Example 3, were intraperitoneally injected at a dose of 1 μg to C57BL/6 (male, 6 weeks, 5 in each group) once every 5 days for 10 days. Three days after the immunization, blood was sampled, 1:500 diluted, and incubated at room temperature for two hours on black 96-well plates.

FIG. 60 shows the production of *E. coli*-derived extracellular vesicle-specific antibodies. The combined injection of *E. coli*- and *Klebsiella*-derived extracellular vesicles induced higher levels of *E. coli*-derived extracellular vesicle-specific antibodies, as compared to *E. coli*-derived extracellular vesicles alone.

FIG. 61 shows the production of *Klebsiella*-derived extracellular vesicle-specific antibodies. The combined injection of *E. coli*- and *Klebsiella*-derived extracellular vesicles induced higher levels of *Klebsiella*-derived extracellular vesicle-specific antibodies, as compared to *Klebsiella*-derived extracellular vesicles alone.

From these results, it can be understood that a mixture of extracellular vesicles derived from *E. coli* and *Klebsiella* can be used as a vaccine preventive of diseases caused by *E. coli*- and *Klebsiella*-derived extracellular vesicles as well as *E. coli* and *Klensiell* infections.

Example 23

Base Sequencing of Genetic Substance of Gut Flora-Derived Extracellular Vesicles Extracellular vesicles were isolated from feces of C57BL/6 (6 weeks old, male) and BALB/c (6 weeks old, male). Deionized water added to 10 μg of each of the extracellular vesicles in such an amount as to form a total volume of 8 μl. To each of the vesicles was added 2 μl of random decamer (Ambion, 5722G), followed by incubation at 95° C. for 10 min and at 75° C. for 10 and storage at 4° C. Each sample was treated with random decamer and incubated with AMV reverse transcriptase (Promega, M510F) 3 μl, AMV reverse transcriptase buffer (Promega, M515A) 4 μl, 10 mM dNTP 2 μl, and RNase inhibitor (Promega, N211B) 1 μl, for 10 min at 25° C. and then for 2 hours at 37° C. Of 20 μl of each sample treated with AMV reverse transcriptase, 1 μl was used to detect a 16S rRNA gene by PCR. For use in PCR, 1 μl of the sample was mixed with 0.5 μl of Taq enzyme (NEB, M0273S), 2 μl of Taq enzyme buffer (NEB, B9014S), 1 μl of 10 mM dNTP, 1 μl of 10 pM bacterial universal forward primer (5'aaggcgacgatc-cctagctg-3'; SEQ ID NO. 4), 1 μl of 10 pM bacterial universal reverse primer (5'ttgagcccggggatttcaca-3'; SEQ ID NO. 5), and 13.5 μl of deionized water. After initial incubation at 95° C. for 2 min, PCR was performed with 45 cycles of 95° C. for 30 sec, 55° C. for 30 sec, and 72° C. for 45 sec. Final extension was done at 72° C. for 5 min. SolGent (63-10, Whaam-dong, Yusung Ku, Taejeon) was asked to analyze the base sequence of the PCR products thus obtained. FIGS. 62 and 63 are base sequence analysis results of PCR products from C57BL/6 and BALB/c, respectively.

As can be seen in FIGS. 62 and 63, multiple peaks appeared at positions 100 ~120 and 150~190, which indicated the co-existence of various bacterial 16S rRNAs. That is, the extracellular vesicles separated from feces were originated from various kinds of intestinal bacteria. Comparison between the 16S rRNA base sequences of the NCBI database and the sequencing results in consideration of the multiple peaks suggested the presence of *Escherichia coli* and *Klebsiella pneumoniae* out of 10 representative bacteria that are found in feces.

To confirm the presence of 16S rRNA in the *E. coli*-derived extracellular vesicles, RT-PCR was performed with 10 μg of the extracellular vesicles as described above. Deionized water was used as a negative control. For a positive control, 1 μl of a culure of intestinal *E. coli* which was grown to an O.D. value of 1.0 was used. To 20 μl of the. RT-PCR product was added 5 μl of 5× Green GoTaq Flexi Buffer (Promega, M891A), and 5 μl of this mixture was loaded to 2% agarose gel. After gel running at 100 V for 30 min, the gel was immersed for 10 min in 0.005% EtBr solution and photographed under UV light.

As shown in FIG. 64, the same band as in the positive control was visualized, indicating that a 16S rRNA gene or its RNA transcript exists in the *E. coli*-derived extrcellular vesicles.

Example 24

Presence of Proteins of Gut Flora-Derived Extracellular Vesicles in Tissue and Body Fluid Six hours after the intraperitoneal injection of 25 μg of gut flora-derived extracellular vesicles into C57BL/6 (6 weeks old, male, 3 in each group), organs and body fluid were removed from the mice. To examine whether the organs and body fluid contained proteins of the extracellular vesicles therein, ELISA using an antibody to the extracellular vesicles was carried out. Mouse orans, afer being removed, were immersed in liquid nitrogen and ground in a mortar. After lysis in a RIPA buffer (50 mM Tris (pH 7.5), 1% NP-40, 0.25% Na-Deoxycholate, 100 mM NaCl, 1 mM EDTA, protease inhibitor), proteins were obtained by centrifugation at 4° C. and 13,000 rpm for 10 min. Body fluid was taken as described in Examples 5 and 6.

FIG. 65 shows the presence of intraperitoneally injected extracellular vesicles in various organs, peritoneal fluid (PF), urine and blood, suggesting that the body fluid that is readily sampled, such as urine and blood, can be used to diagnose inflammatory diseases caused by extracellular vesicles.

the preferred embodiments of the present invention have been disclosed for illustrative purposes, those skilled in the art will appreciate that various modifications, additions and substitutions are possible, without departing from the scope and spirit of the invention as disclosed in the accompanying claims.

INDUSTRIAL APPLICABILITY

The gut flora-derived extracellular vesicles of the present invention can be used to effectively discover drugs that are preventive or therapeutic of gut flora-derived extracellular vesicle-induced diseases. Also, gut flora-derived extracellular vesicles themselves or their modifications may be used to develop vaccines against gut flora infections or gut flora-derived extracellular vesicle-caused diseases. Further, the gut flora-derived extracellular vesicles can be applied to the development of a method for diagnosing a pathogenic factor responsible for the onset of gut flora-derived extracellular vesicle-caused diseases.

The invention claimed is:

1. A method of making a composition for reducing symptoms associated with sepsis that are induced by at least one strain of *E. coli* and *Klebsiella* spp., the method comprising:
   providing gut flora comprising at least one strain of *E. coli* and *Klebsiella* spp., wherein the gut flora is from a mammal that has been diagnosed as having sepsis induced by the at least one strain of *E.coli* and *Klebsiella* spp.;
   processing said gut flora to collect extracellular vesicles that originated from the at least one strain; and
   formulating a composition comprising the collected extracellular vesicles at a sublethal dose for administration to a mammal.

2. The method according to claim 1, wherein providing the gut flora comprises:
   obtaining a sample selected from the group consisting of feces, intestine, gastric fluid, intestinal fluid and oral fluid from a mammal, said mammal being either same or different to the mammal that is in need of the reduction.

3. The method of claim 1, wherein the composition further comprises a drug that has an effect of decreasing a side effect of the composition.

4. The method according to claim 1, wherein providing the gut flora comprises obtaining a sample from a mammal that is diagnosed as having sepsis induced by the at least one strain of *E.coli* and *Klebsiella* spp., wherein the sample is selected from the group consisting of feces, intestine, gastric fluid, intestinal fluid and oral fluid from the mammal.

5. A method of reducing symptoms associated with sepsis that are induced by at least one strain of *E. coli* and *Klebsiella* spp., the method comprising:
   administering the formulated composition of claim 1 to a patient in need of reduction of symptoms associated with sepsis that are induced by the at least one strain of *E. coli* and *Klebsiella* spp.

* * * * *